(12) United States Patent
Zhang et al.

(10) Patent No.: US 9,133,463 B2
(45) Date of Patent: Sep. 15, 2015

(54) ENGINEERING MICROORGANISMS

(75) Inventors: ShuoCheng Zhang, Charlottetown, CA (US); Roberto Armenta, Dartmouth, CA (US)

(73) Assignee: DSM NUTRITIONAL PRODUCTS AG, Kaiseraugst (CH)

( * ) Notice: Subject to any disclaimer, the term of this patent is extended or adjusted under 35 U.S.C. 154(b) by 287 days.

(21) Appl. No.: 13/414,353

(22) Filed: Mar. 7, 2012

(65) Prior Publication Data

US 2012/0244584 A1 Sep. 27, 2012

Related U.S. Application Data

(60) Provisional application No. 61/449,848, filed on Mar. 7, 2011.

(51) Int. Cl.
| | |
|---|---|
| C12N 15/79 | (2006.01) |
| C12P 7/64 | (2006.01) |
| C12N 1/12 | (2006.01) |
| C12N 15/01 | (2006.01) |

(52) U.S. Cl.
CPC ......... *C12N 15/79* (2013.01); *C12N 1/12* (2013.01); *C12N 15/01* (2013.01); *C12P 7/6427* (2013.01)

(58) Field of Classification Search
None
See application file for complete search history.

(56) References Cited

U.S. PATENT DOCUMENTS

| | | | |
|---|---|---|---|
| 5,340,742 A | 8/1994 | Barclay | |
| 6,027,900 A * | 2/2000 | Allnutt et al. | 435/6.15 |
| 6,410,288 B1 | 6/2002 | Knutzon et al. | |
| 6,451,567 B1 | 9/2002 | Barclay | |
| 6,607,900 B2 | 8/2003 | Bailey et al. | |
| 7,001,772 B2 * | 2/2006 | Roessler et al. | 435/471 |
| 7,214,491 B2 | 5/2007 | Yadav et al. | |
| 7,723,503 B2 | 5/2010 | Mukerji et al. | |
| 2004/0161831 A1 | 8/2004 | Komazawa et al. | |
| 2006/0286650 A1 | 12/2006 | Ono et al. | |
| 2007/0256146 A1 | 11/2007 | Metz et al. | |
| 2008/0076166 A1 | 3/2008 | Cirpus et al. | |
| 2009/0117194 A1 | 5/2009 | Burja et al. | |
| 2011/0223641 A1 | 9/2011 | Stephanopoulos et al. | |

FOREIGN PATENT DOCUMENTS

| | | |
|---|---|---|
| CN | 1556850 A | 12/2004 |
| WO | 02083869 A3 | 10/2002 |
| WO | 2007/069078 A2 | 6/2007 |
| WO | WO 2007/069078 * | 6/2007 |

(Continued)

OTHER PUBLICATIONS

First office a tion from related Chinese Application No. 20128008055.4 issued Aug. 7, 2014, 13 pages.

(Continued)

*Primary Examiner* — Alexander Kim
(74) *Attorney, Agent, or Firm* — Kilpatrick, Townsend & Stockton LLP

(57) ABSTRACT

The present disclosure provides, inter alia, *Thraustochytrium* and relevant methods and reagents, including engineered regulatory sequences from and/or operative in Thraustochytrid or *Thraustochytrium*, selectable markers useful for engineering microorganisms such as Thraustochytrids, methods for mutagenizing microorganisms, novel strains produced by mutagenesis and methods and compositions related to production of particular compounds in microorganisms.

40 Claims, 20 Drawing Sheets

(56) References Cited

FOREIGN PATENT DOCUMENTS

| WO | 2008/129358 A2 | 10/2008 |
|---|---|---|
| WO | 2009/010825 A2 | 1/2009 |
| WO | 2010/108114 A2 | 9/2010 |
| WO | 2011/037207 A1 | 3/2011 |
| WO | 2011/090731 A1 | 7/2011 |

OTHER PUBLICATIONS

Abstract of KR20110037588, Jo Young et al., Apr. 13, 2011, 1 page.

GenBank: EU074209.1, Sep. 2, 2007, "Thraustochytrium sp. FJN-10 delta-4 fatty acid desaturase (DELT-4) gene, promoter region and partial cds", Huang et al., retrieved from the internet, <URL http://www.ncbi.nlm.nih.gov/nuccore/eu074209>.

Huang et al., "Cloning and functional identification of Delta5 fatty acid desaturase gene and its 5'-upstream region from marine fungus thraustochytrium sp. FJN-10", Marine Biotechnology, 13(1):12-21 (2011).

International Search Report and the Written Opinion of the International Searching Authority, mailed Jul. 12, 2012.

Burja et al., "Isolation and characterization of polyunsaturated fatty acid producing Thraustochttrium species: screening of strains and optimization of omega-3 production", Appl. Microbiol. Biotechnol., 72:1161-1169 (2006).

Matsuda et al., "The analysis of delta12-fatty acid desaturase function revealed that two distinct pathways are active for the synthesis of polyunsaturated fatty acids in Thraustochytrium aureum ATTC 34304", J. Lipid Res., 53(6):1210-1222 (2012).

Qiu et al., "Identification of a delta4 fatty acid desaturase from Thraustochytrium sp. involved in the biosynthesis of docosahexanoic acid by heterologous expression in *Saccharomyces cerevisiae* and *Brassica juncea*", J. Biol. Chem., 276(34):31561-31566 (2001).

Raghukumar, Seshagiri, "Traustochytrid marine protists: production of PUFAs and other emerging technologies", Mar. Biotechnol., 10:631-640 (2008).

Sakaguchi et al., "A versatile transformation system for thraustochytrids applicable to both multiple transgene expression and gene targeting", Appl. Environ. Microbial., published online ahead of print on Feb. 17, 2012, 39 pages.

Examination Report No. 1 from related Australian Application No. 2012226528, Jul. 25, 2014, 4 pages.

European Application No. 12755051.5, Partial Supplementary Search Report, Nov. 24, 2014, 8 pages.

Database Geneseq, Delta-4 desaturase 5' end containing clone 5'-217, SEQ ID 16., XP002732307, EBI database accession No. GSN: AVA91531, Mar. 19, 2009.

Database Geneseq, Delta-5 elongase 3' end containing clone 5' D2-1, SEQ ID 11., XP002732308, EBI database accession No. GSN: AVA91520, Mar. 19, 2009.

Huang et al., Cloning and Functional Identification of Delta5 Fatty Acid Desaturase Gene and Its 5' -Upstream Region from Marine Fungus Thraustochytrium sp. FJN-10, Marine Biotechnology, Springer-Verlag, NE, vol. 13, No. 1, 12-21, Apr. 1, 2010.

European Application No. 12755051.5, Extended European Search Report, Apr. 9, 2015, 11 pages.

China Application No. 201280018055.4, Office Action issued Apr. 15, 2015, 15 pages.

* cited by examiner

SEQUENCE LISTING

```
<160> NUMBER OF SEQ ID NOS: 69

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 1
cgcggcttcc cgtctccaag c                                                   21

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 2
ccgagtccat ggtgcccggc                                                  20

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 3
gaccatgatt acgccaagct ct                                               22

<210> SEQ ID NO 4
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 4
gttttcccag tcacgacgt                                                   19

<210> SEQ ID NO 5
<211> LENGTH: 724
<212> TYPE: DNA
<213> ORGANISM: Thraustochytrium sp.

<400> SEQUENCE: 5
cgcggcttcc cgtctccaag cttcgtctcg gtagagattc tatcttcgcc cggcagcccg      60
ccgccgtccg gcaagtgtag aacggcagaa agcccacttg cacggaacgc ccgacaagtt     120
gacgaaagcg gcccgcaagt gcggcagccc ggctggtttt tcctcgcggc gaggccaaac     180
cgccaacgcc accaagccag acaccaggta tgtgccgcac gcgccgccgc acgcgagccc     240
cgaggatgcc ccgtacgcgc tgacgccttt ctccgccccg cccgcgagaa gacgcgctcc     300
ggcaacggcg ggagccgagc gaacgggcga ggattgatcg agtagctgca ggttgagaaa     360
aaaggaaaac cgccgagatg gacaacggct ggatggacga aagacgcac gaggacgcga      420 ggactgacga tgatcacgtg cgcaggaaga cttgaaaaga agcaaggaag gtagaaaaaa     480
aagaagaaat caagcaagat gcgcgagatc gttcacattc agggcggcca gtgcggcaac     540
caggtcggcg ccaagttctg ggaggtcatc tccgatgagc acggtgtgga tcccaccggc     600
tcgtaccatg gcgactcgga cctccagctc gagcgcatca acgtctactt caacgaggcc     660
accggcggtc gctacgtgcc ccgcgccatc ctcatggacc tcgagcccgg gcaccatggac    720 tcgg                                                                  724

<210> SEQ ID NO 6
<211> LENGTH: 490
<212> TYPE: DNA
<213> ORGANISM: Thraustochytrium sp.

<400> SEQUENCE: 6
cgcggcttcc cgtctccaag cttcgtctcg gtagagattc tatcttcgcc cggcagcccg      60
ccgccgtccg gcaagtgtag aacggcagaa agcccacttg cacggaacgc ccgacaagtt     120
gacgaaagcg gcccgcaagt gcggcagccc ggctggtttt tcctcgcggc gaggccaaac     180
cgccaacgcc accaagccag acaccaggta tgtgccgcac gcgccgccgc acgcgagccc     240
cgaggatgcc ccgtacgcgc tgacgccttt ctccgccccg cccgcgagaa gacgcgctcc     300
```

```
ggcaacggcg ggagccgagc gaacgggcga ggattgatcg agtagctgca ggttgagaaa    360
aaaggaaaac cgccgagatg gacaacggct ggatggacga gaagacgcac gaggacgcga    420
ggactgacga tgatcacgtg cgcaggaaga cttgaaaaga agcaaggaag gtagaaaaaa    480
aagaagaaat                                                           490
```

```
<210> SEQ ID NO 7
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 7
ggcctgtctc ccttggccat cc                                              22

<210> SEQ ID NO 8
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 8
gggcatctgg ccgtccggc                                                  19

<210> SEQ ID NO 9
<211> LENGTH: 1115
<212> TYPE: DNA
<213> ORGANISM: Thraustochytrium sp.

<400> SEQUENCE: 9
ggcctgtctc ccttggccat ccattgcgct gcggaagcat tggattgcga actgcgtcgg     60
ccagatcgct tggtttccca acatgagacg cgctctgtcg gcaagaccat ttccgccccc    120
ggctttgctc acaaccaact cgtagtagat tttgtaaaga acactgcacg tctgactgct    180
cccagcccgc acgcattgcg cttggcagcc tcggtcccaa accgtcacgg tcgctgcccg    240
gtccacggga aaaataact tttgtccgcg agcggccgtt caaggcgcag ccgcgagcgt     300
gccaaccgtc cgtcccgcat tcttttccca atgttggatt cattcattct tgccaggcca    360
gatcatctgt gcctccctcg cgtgcccttc cttagcgtgc gcagatctct tcttcccaga    420
gcccgcgcgg cgcttcgtgg agtcggcgtc catgtcatgc gcgcgcggcg tcttgacccc    480
ctcggcccct ttggttcgcg gctgcgcaac gagccgtttc acgccattgc gaccaaccgc    540
gcgctaaaat cggattggcc gttgcacgcc gattttgcag cacctctggg ctgtgaggga    600
cgaccgtcca cttttacccg cacagagtgg actttcaccc cctcactcca ctgaagccaa    660
cttttcgccg tcttcccaac ccaaagttta tgctagccct catgccgcaa cggacgtcac    720
ccccatttcc actggcgacg tggggacctg ggcgcaataa ggcgcgagaa ggaaattacg    780
acggcacact ggggccagaa gagggcacta ggagcggcaa cccactggcg cggcacagcg    840
gtttggcgcg gggatcaaag caaaacccgg ctcatccaga gcaaaccgga atcagccttc    900
agacggtcgt gcctaacaac acgccgttct accccgcctt ccttgcgtcc ctcgcctccc    960
ccgagcccaa gtcttccgcc cgctcctaac gccaaccaag caagatgcgt gaggtcatct   1020
ccatccacat cggccaggcc ggtgtccagg tcggtaacgc ctgctgggag ctctactgcc   1080
tcgagcatgg catccagccg gacggccaga tgccc                              1115
```

<210> SEQ ID NO 10
<211> LENGTH: 1004
<212> TYPE: DNA
<213> ORGANISM: Thraustochytrium sp.

<400> SEQUENCE: 10

| | | | | | |
|---|---|---|---|---|---|
| ggcctgtctc | ccttggccat | ccattgcgct | gcggaagcat | tggattgcga | actgcgtcgg | 60 |
| ccagatcgct | tggtttccca | acatgagacg | cgctctgtcg | gcaagaccat | ttccgccccc | 120 |
| ggctttgctc | acaaccaact | cgtagtagat | tttgtaaaga | acactgcacg | tctgactgct | 180 |
| cccagcccgc | acgcattgcg | cttggcagcc | tcggtcccaa | accgtcacgg | tcgctgcccg | 240 |
| gtccacggga | aaaaataact | tttgtccgcg | agcggccgtt | caaggcgcag | ccgcgagcgt | 300 |
| gccaaccgtc | cgtcccgcat | tcttttccca | atgttggatt | cattcattct | tgccaggcca | 360 |
| gatcatctgt | gcctccctcg | cgtgcccttc | cttagcgtgc | gcagatctct | tcttcccaga | 420 |
| gcccgcgcgg | cgcttcgtgg | agtcggcgtc | catgtcatgc | gcgcgcggcg | tcttgacccc | 480 |
| ctcggcccct | ttggttcgcg | gctgcgcaac | gagccgtttc | acgccattgc | gaccaaccgc | 540 |
| gcgctaaaat | cggattggcc | gttgcacgcc | gattttgcag | cacctctggg | ctgtgaggga | 600 |
| cgaccgtcca | cttttacccg | cacagagtgg | actttcaccc | cctcactcca | ctgaagccaa | 660 |
| cttttcgccg | tcttcccaac | ccaaagttta | tgctagccct | catgccgcaa | cggacgtcac | 720 |
| ccccatttcc | actggcgacg | tggggacctg | ggcgcaataa | ggcgcgagaa | ggaaattacg | 780 |
| acggcacact | ggggccagaa | gagggcacta | ggagcggcaa | cccactggcg | cggcacagcg | 840 |
| gtttggcgcg | gggatcaaag | caaaacccgg | ctcatccaga | gcaaacccga | atcagccttc | 900 |
| agacggtcgt | gcctaacaac | acgccgttct | accccgcctt | ccttgcgtcc | ctcgcctccc | 960 |
| ccgagcccaa | gtcttccgcc | cgctcctaac | gccaaccaag | caag | | 1004 |

<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 11
ggtacgtcgg tgagggtatg gag                                              23

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
gccgctaaac cgcagactgg                                                  20

<210> SEQ ID NO 13
<211> LENGTH: 727
<212> TYPE: DNA
<213> ORGANISM: Thraustochytrium sp.

<400> SEQUENCE: 13

| | | | | | |
|---|---|---|---|---|---|
| ggtacgtcgg | tgagggtatg | gagagggtga | gttctccgag | gccccgtgag | gatctcgccg | 60 |
| cccctcgagaa | ggattacgag | gaggtcggcg | ccgagaccgc | cgaggcgag | gacgaggagg | 120 |
| agggcgagga | gttctaaatg | cattcgcatg | gctccgcacc | accacacacc | accgcccctc | 180 |

```
ttctttcctt gctcactcga tccatagcca cttacctgcc ccttccctct accactgcca    240
cgtgcggcgt atgagcgcgc ttgcacccgc aaccttctct ctagttgttc acaattacac    300
ccgctatcaa tactcacgca ttcatcttcc ccttttttc tactttacgt accggtgctc    360
acttacttac acctgcccgc cttgttcatt cattcttctc gatgacaacg gcaggctctg    420
cttgcggcgc gcgcacgcat cccttactcc gccgcgcacc gacaagcctg cgcaaaaaac    480
aaaaaaaact tatcttcgct cgcggctccg atgtcgcggc ggcgtacgag accgcgccga    540
gttccgcccg ccatgcgatc gagagtctct ctcgtaggag cgggaccgcg agcgacctcg    600
gtgcctccga tagccagctg ggcttctaga ccggctgggg gaccgcccgc ggcgtacctc    660
tgcgcttcgg tggcccttaa aaggctgatc gtggaaaagg tcgctctcca gtctgcggtt    720
tagcggc                                                              727

<210> SEQ ID NO 14
<211> LENGTH: 590
<212> TYPE: DNA
<213> ORGANISM: Thraustochytrium sp.

<400> SEQUENCE: 14
atgcattcgc atggctccgc accaccacac accaccgccc ctcttctttc cttgctcact     60
cgatccatag ccacttacct gccccttccc tctaccactg ccacgtgcgg cgtatgagcg    120
cgcttgcacc cgcaaccttc tctctagttg ttcacaatta cacccgctat caatactcac    180
gcattcatct tccccttttt ttctacttta cgtaccggtg ctcacttact tacacctgcc    240
cgccttgttc attcattctt ctcgatgaca acgcaggct ctgcttgcgg cgcgcgcacg    300
catcccttac tccgccgcgc accgacaagc tgcgcaaaa acaaaaaaaa acttatcttc    360
gctcgcggct ccgatgtcgc ggcggcgtac gagaccgcgc cgagttccgc cgccatgcg    420 atcgagagtc tctctcgtag gagcgggacc gcgagcgacc tcggtgcctc cgatagccag    480
ctgggcttct agaccggctg ggggaccgcc cgcggcgtac ctctgcgctt cggtggccct    540
taaaaggctg atcgtggaaa aggtcgctct ccagtctgcg gtttagcggc               590

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
cggcaacacc accgccgtcc                                                 20

<210> SEQ ID NO 16
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 16
cggagaccaa gccgcccatc acc                                             23

<210> SEQ ID NO 17
<211> LENGTH: 869
<212> TYPE: DNA
<213> ORGANISM: Thraustochytrium sp.
```

<400> SEQUENCE: 17

```
cggcaacacc accgccgtcc aggagatgtt caagcgcgtc tcggagcagt tcaccagcat        60
gttccgccgc aaggccttcc ttcactggta caccggcgag ggcatggacg agatggagtt       120
caccgaggcc gagtcgaaca tgaacgacct tgtctccgag taccagcagt accaggacgc       180
caccgccgag gaggaaggcg agttcgacga ggacgaggag gagtactaag cgccttcagg       240
caggctgatc cctactgtgg gggctctgac ggacggccgg tctttgtacg taaacaggcg       300
cttcttcgcg gcccgccgag gggggcggca acgagccggg tggcgtggca cggacaaggc       360
aagagccttt ccatcccgca taaagtgatg caccattttg accttgttga tcgttttgt        420
gtgtttagag cggccccgtg cgggtaggcg aagtgcgctt ctgagcaagg aagagagagg       480
tgcagcttct tcttgatcag tgtggtaatc ttcaacggcc acgctcgctt attcgatacc       540
tgtaaagcta ccggtgcacc cgtgcaagtt gggcaccacg tagttgtact ggtgaatcca       600
aatgttagcc gctagcttgg tgccctttc gacaggaagg cttggtgaa aagccatgct         660
gtcgatctcc cttgggtcct cgttcgtgac gctaggccag agaatagctg tgtgccgcgc       720
agtcgaagcc agcgcgcgcg cgtcggggcc gagcatagag ttagcaattc agttgtttcg       780
ggctcttgat gaggccgcca gagagcgaag aaggatgaac ttaccagatc cgcgctccgg       840
tgtattggtg atgggcggct tggtctccg                                         869
```

<210> SEQ ID NO 18
<211> LENGTH: 640
<212> TYPE: DNA
<213> ORGANISM: Thraustochytrium sp.

<400> SEQUENCE: 18

```
gcgccttcag gcaggctgat ccctactgtg ggggctctga cggacggccg gtctttgtac        60
gtaaacaggc gcttcttcgc ggcccgccga gggggcggc aacgagccgg tggcgtggc        120
acggacaagg caagagcctt ccatcccgc ataaagtgat gcaccatttt gaccttgttg       180
atcgttttg tgtgtttaga gcggccccgt gcgggtaggc gaagtgcgct tctgagcaag       240
gaagagagag gtgcagcttc ttcttgatca gtgtggtaat cttcaacggc acgctcgct        300
tattcgatac ctgtaaagct accggtgcac ccgtgcaagt gggcaccac gtagttgtac       360
tggtgaatcc aaatgttagc cgctagcttg gtgccctttt cgacaggaag gcttggtga        420
aaagccatgc tgtcgatctc ccttgggtcc tcgttcgtga cgctaggcca gagaatagct       480
gtgtgccgcg cagtcgaagc cagcgcgcgc gcgtcggggc cgagcataga gttagcaatt       540
cagttgtttc gggctcttga tgaggccgcc agagagcgaa gaaggatgaa cttaccagat       600
ccgcgctccg gtgtattggt gatgggcggc ttggtctccg                             640
```

<210> SEQ ID NO 19
<211> LENGTH: 950
<212> TYPE: DNA
<213> ORGANISM: Thraustochytrium sp.

<400> SEQUENCE: 19

```
caacgccatc ctcgaccaca gcaaggacac gcaccgcttc ggctacggta tccagatcgg        60
ataaatatta taccgcccct tccgctctcc tttttctttt tgctcgtctg gatgccagac       120
taaggagtcc ttgctcctct gcgcaaggct gctcacccag agtctctgcc tgtggttgag       180
cgcccaccaa caggttaaag cgaaccaggg ccgccccgtt gccgctgcga tgtcgctgct       240
cttgcgagac tcttcattag atcggcggaa tgctgccgca ggactgaccg cctcttcgtt       300
```

-continued

```
cgttcgtttg tacgcgagcg gtgcgagcgg cttcgttgtt ggcagatagg cagaacgcga    360
gcagttcacg tttctttgca gctttatcta tccgcaaatt cgcctcagcg tctgcaactt    420
tccggtgagg acagcagagc tgcagttctg atcgtctcca tcttttggag cgcatgtcga    480
cgtcccccag ctcgtctccg tctccctgg agtggacggt ctctttcaca gtgcctgggt    540
gcggccattt ccctaaatag gttgcgcagc cgagtttcct taaacgtgcc tggtccgcgt    600
gcttccgcct tactacctga acgcgcagta gctcggcgcg tgccgcttta aggcgggcgg    660
ggtggctgct cttgcttacg ccaggcgcgt acgtcagcag cgccggcgcc atgctgccca    720
tagcggccac agaatcgtag gcgctgcaat cgggaactgc caagatggca atcgagacga    780
tcccccaaaa gtggacaagc accgtcaaag taacctggct gatgatggcc gggaccgcct    840
ggtgacggcc agccggcaaa accggaatct atcacgagga ctgggcagat caagggccta    900
gtgctagcga gcagctcgag cgaaagaagc gcgccagcag cgcaggcacg              950
```

<210> SEQ ID NO 20
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 20

```
tatatatcta gacaacgcca tcctcgacca cag                                 33
```

<210> SEQ ID NO 21
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 21

```
tatataccat ggcgtgcctg cgctgctggc                                     30
```

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22

```
gatgctcgtc aggggggcgg                                                20
```

<210> SEQ ID NO 23
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 23

```
cccggaccac accggcg                                                   17
```

<210> SEQ ID NO 24
<211> LENGTH: 1216
<212> TYPE: DNA
<213> ORGANISM: Thraustochytrium sp.

<400> SEQUENCE: 24

```
gtgaccaaaa gccgtgaacg ggcgtggccg aggctacagc acgcagcggt gttctctgcg        60
tattatattt ttcgcaaggt ttcccgacgg ctggtccgcg tgcccgcgcc gcgcgcacgc       120
tctcactaga cgttggtcat gagtgtttcg agtcaagacc tcggagaaga attggggcgc       180
acaccttccg tgcgcgcacc cctgccactg tataccgtgc gtaccccacc agacagaagg       240
tcaccacccg tgctctcttc gtcagctata ccgtgtgctg tagatcgtcg caggattcgg       300
gttgtgcaca ccgcgctccg tgggctgggg gccctggcgc ggcggcttcc taggatatag       360
tctataaaac ccagcgaatt ttacacacag agcggttcat ttgcgctggg tccggtgcgc       420
aatttcgggg cacagcctgc acgtttacat cgacgtaaca gccacagtca tcgtcgccag       480
cctcttcggc cttccaccg acccggctgc tgcccgcctt cctggctggc tgatgaacta       540
tcgcggcctg cctggcacgt acgtgcccct cccatttctc cccggtcctc cagaaatgcg       600
cctccggccc caatgaaagc aggcgttggc catgcggcgc ccgacatctg ggtcctcgcg       660
ccttctttga tgacatcgtc ctcatcgtcg tcggcgacct ggtcttcgtg atcgcttgtt       720
gatcacgcgc ttggcatctt gcgaggagaa ccgtctgcac tcttttggcg cggccgaggt       780
gccttccggg gtgcaggcca gtcgccagac cagacctgct gcaaagcccg aacatcgccg       840
tcgaggtaga ccattaggta cgtacgtacg cacgtcttca tgatcgacgc caacgtcatg       900
cggtcgatgc cccgccacgc gatggcgcta gcagccagga gcgcgtgtgt acgggcgcgg       960
agcttcgctc gcaagcaaag ctgggcgctt gggccgggga tcgggccact acttggacga      1020
acgaacgaaa cgcatgacgt catccttggc agtaaatctt gccggagcgc gcaaaaccca      1080
ggctggacgc gctgggtgcg attgagaacc gcaagctttg gagcctttca ctgagcaggg      1140
ggaactgacg ctggagcgcg cgaccgtagg cgaaggaatt tgatcgaagt aggcaggact      1200
gcccgcaggg gtcagg                                                     1216
```

<210> SEQ ID NO 25
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 25

```
tatatactcg aggtgaccaa aagccgtgaa cgg                                     33
```

<210> SEQ ID NO 26
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 26

```
tataccat ggcctgaccc ctgcgggcag                                           30
```

<210> SEQ ID NO 27
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 27

```
caacctggtt gatcctgcca gta                                                23
```

```
<210> SEQ ID NO 28
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 28
caacctggtt gatcctgcca gtagccc                                            27

<210> SEQ ID NO 29
<211> LENGTH: 1764
<212> TYPE: DNA
<213> ORGANISM: Thraustochytrium sp.

<400> SEQUENCE: 29
tcactacgga aaccttgtta cgacttcacc ttcctctaaa caataagatt cacccgagtt        60 ctgaccccc tcgcgaacaa acgctcaaaa ggtcatccca tggtttcatc ggaccgttca       120
atcggtaggt gcgacgggcg gtgtgtacaa agggcaggga cgtattcaat gcaagctgat      180
gacttgcgtt tactaggaat tcctcgttgg agattaataa ttgcaaaaat ctagccccag      240
cacgatgggc gttgaaagga tttgccatgc cttccggcaa agcacctcgc tgcgaacaac      300
gatgaccacc cgttgaaccc atcagtgtag cgcgcgtgcg gcccagaaca tctaagggca      360
tcacagacct gttattgcct cgaacttcct gctcgtatac cgaacatgtc cctctaagaa      420
gcgtacgcaa gtatgtcgcc ataccaccg ctatttagta ggccgaggtc tcgttcgtta       480
acggaattaa ccagacaaat cactccacca actaagaacg gccatgcacc accacccata      540
gaatcaagaa agagctctca atctgtcaat cctacctatg tctggacctg gtaagttttc      600
ccgtgttgag tcaaattaag ccgcaggctc cactcctggt ggtgcccttc cgtcaattcc      660
tttaagtttc agccttgcga ccatactccc cccggaaccc aaagactttg atttctcatg      720
tgctgctgcg agggtccaat acaaacaccc cgcaatcgca agtcggcatc gtttacggtc      780
tagactacga tggtatctaa tcatcttcga tccccagact ttcgttcttg attaatgaaa      840
acatgcttgg taaatgcctt cgctgtagtt cgtctttcgg aaatccaaga atttcacctc      900
tagctcctaa atacgaatac ccccaactgt tcctattcat cattactcag atgtgcaaac      960
caacaaaata gcacccgagc cctatctgat catcccataa taaacatcca ggtcatacga     1020
cctgcttgga acactctgct ttaattacag tgaacgacgc cactaaaaaa agaggcgagg     1080
atggcagagg agccgctcgg caaacagagc gcagtcgcgc aaagaccggg gctcccgccc     1140
cagaaattca actacgagct ttttaactgc aacaacttta gcatacgctt ctggagctgg     1200
aattaccgcg gctgctggca ccagacttgc cctccagttg atcctcgatg agggttttac     1260
attgctctca ttccaatagc aagacgcgaa gcgccccgca ttgatatttc tcgtcactac     1320
ctcgtggagt ccacattggg taatttacgc gcctgctgcc ttccttggat gtggtagccg     1380
tctctcaggc tccctctccg gagtcgagcc ctaactcccc gtcacccgtt atagtcaccg     1440
tagtccaata cactaccgtc gacaactgat ggggcagaaa ctcaaacgat tcatcgctcc     1500
aaacaagcga tctgctcaat tatcatgact caccatctta cttggcttca actctaataa     1560
gtgcggccct cccgaacagt cgggccctct cagcatgtat taattccaga attactgcag     1620
gtatccatat aaagaaaata ccgaagaaat cataactgat ataatgagcc gttcgcagtc     1680
tcacagtata atcgcttata cttacacatg catggcttaa tctttgagac gagcgtaggg     1740
ctactggcag gatcaaccag gttg                                            1764
```

<210> SEQ ID NO 30
<211> LENGTH: 4235
<212> TYPE: DNA
<213> ORGANISM: Thraustochytrium sp.

<400> SEQUENCE: 30

| | | | | | |
|---|---|---|---|---|---|
| gacgaaaggg | cctcgtgata | cgcctatttt | tataggttaa | tgtcatgata | ataatggttt | 60 |
| cttagacgtc | aggtggcact | tttcggggaa | atgtgcgcgg | aaccccctatt | tgtttatttt | 120 |
| tctaaataca | ttcaaatatg | tatccgctca | tgagacaata | ccctgataa | atgcttcaat | 180 |
| aatattgaaa | aggaagagt | atgagtattc | aacatttccg | tgtcgcccctt | attcccttt | 240 |
| ttgcggcatt | ttgccttcct | gttttttgctc | acccagaaac | gctggtgaaa | gtaaaagatg | 300 |
| ctgaagatca | gttgggtgca | cgagtgggtt | acatcgaact | ggatctcaac | agcggtaaga | 360 |
| tccttgagag | ttttcgcccc | gaagaacgtt | ttccaatgat | gagcactttt | aaagttctgc | 420 |
| tatgtggcgc | ggtattatcc | cgtattgacg | ccgggcaaga | gcaactcggt | cgccgcatac | 480 |
| actattctca | gaatgacttg | gttgagtact | caccagtcac | agaaaagcat | cttacggatg | 540 |
| gcatgacagt | aagagaatta | tgcagtgctg | ccataaccat | gagtgataac | actgcggcca | 600 |
| acttacttct | gacaacgatc | ggaggaccga | aggagctaac | cgcttttttg | cacaacatgg | 660 |
| gggatcatgt | aactcgcctt | gatcgttggg | aaccggagct | gaatgaagcc | ataccaaacg | 720 |
| acgagcgtga | caccacgatg | cctgtagcaa | tggcaacaac | gttgcgcaaa | ctattaactg | 780 |
| gcgaactact | tactctagct | tcccggcaac | aattaataga | ctggatggag | gcggataaag | 840 |
| ttgcaggacc | acttctgcgc | tcggcccttc | cggctggctg | gtttattgct | gataaatctg | 900 |
| gagccggtga | gcgtgggtct | cgcggtatca | ttgcagcact | ggggccagat | ggtaagccct | 960 |
| cccgtatcgt | agttatctac | acgacgggga | gtcaggcaac | tatggatgaa | cgaaatagac | 1020 |
| agatcgctga | gataggtgcc | tcactgatta | agcattggta | actgtcagac | caagtttact | 1080 |
| catatatact | ttagattgat | ttaaaacttc | attttttaatt | taaaaggatc | taggtgaaga | 1140 |
| tcctttttga | taatctcatg | accaaaatcc | cttaacgtga | gttttcgttc | cactgagcgt | 1200 |
| cagaccccgt | agaaaagatc | aaaggatctt | cttgagatcc | ttttttttctg | cgcgtaatct | 1260 |
| gctgcttgca | aacaaaaaaa | ccaccgctac | cagcggtggt | ttgtttgccg | gatcaagagc | 1320 |
| taccaactct | ttttccgaag | gtaactggct | tcagcagagc | gcagatacca | aatactgtcc | 1380 |
| ttctagtgta | gccgtagtta | ggccaccact | tcaagaactc | tgtagcaccg | cctacatacc | 1440 |
| tcgctctgct | aatcctgtta | ccagtggctg | ctgccagtgg | cgataagtcg | tgtcttaccg | 1500 |
| ggttggactc | aagacgatag | ttaccggata | aggcgcagcg | gtcgggctga | acggggggtt | 1560 |
| cgtgcacaca | gcccagcttg | gagcgaacga | cctacaccga | actgagatac | ctacagcgtg | 1620 |
| agcattgaga | aagcgccacg | cttcccgaag | ggagaaaggc | ggacaggtat | ccggtaagcg | 1680 |
| gcagggtcgg | aacaggagag | cgcacgaggg | agcttccagg | gggaaacgcc | tggtatcttt | 1740 |
| atagtcctgt | cgggtttcgc | cacctctgac | ttgagcgtcg | atttttgtga | tgctcgtcag | 1800 |
| gggggcggag | cctatggaaa | aacgccagca | acgcggcctt | tttacggttc | ctggccttt | 1860 |
| gctggccttt | tgctcacatg | tgtgctgggc | ccagccggcc | agatctgagc | tcgcggccgc | 1920 |
| gatatcgcta | gctcgaggtg | accaaaagcc | gtgaacgggc | gtggccgagg | ctacagcacg | 1980 |
| cagcggtgtt | ctctgcgtat | tatattttc | gcaaggtttc | ccgacggctg | gtccgcgtgc | 2040 |
| ccgcgccgcg | cgcacgctct | cactagacgt | tggtcatgag | tgtttcgagt | caagacctcg | 2100 |
| gagaagaatt | ggggcgcaca | ccttccgtgc | gcgcacccct | gccactgtat | accgtgcgta | 2160 |

```
cccaccaga cagaaggtca ccacccgtgc tctcttcgtc agctataccg tgtgctgtag    2220
atcgtcgcag gattcgggtt gtgcacaccg cgctccgtgg gctggggcc  ctggcgcggc   2280
ggcttcctag gatatagtct ataaaaccca gcgaatttta cacacagagc ggttcatttg   2340
cgctgggtcc ggtgcgcaat tcgggggcac agcctgcacg tttacatcga cgtaacagcc   2400
acagtcatcg tcgccagcct cttcggcctt cccaccgacc cggctgctgc ccgccttcct   2460
ggctggctga tgaactatcg cggcctgcct ggcacgtacg tgcccctccc atttctcccc   2520
ggtcctccag aaatgcgcct ccggccccaa tgaaagcagg cgttggccat gcggcgcccg   2580
acatctgggt cctcgcgcct ctttgatga  catcgtcctc atcgtcgtcg gcgacctggt   2640
cttcgtgatc gcttgttgat cacgcgcttg gcatcttgcg aggagaaccg tctgcactct   2700
tttggcgcgg ccgaggtgcc ttccggggtg caggccagtc gccagaccag acctgctgca   2760
aagcccgaac atcgccgtcg aggtagacca ttaggtacgt acgtacgcac gtcttcatga   2820
tcgacgccaa cgtcatgcgg tcgatgcccc gccacgcgat ggcgctagca gccaggagcg   2880
cgtgtgtacg ggcgcggagc ttcgctcgca agcaaagctg ggcgcttggg ccggggatcg   2940
ggccactact tggacgaacg aacgaaacgc atgacgtcat ccttggcagt aaatcttgcc   3000
ggagcgcgca aaacccaggc tggacgcgct gggtgcgatt gagaaccgca agctttggag   3060
cctttcactg agcaggggga actgacgctg gagcgcgcga ccgtaggcga aggaatttga   3120
tcgaagtagg caggactgcc cgcaggggtc aggccatggc caagttgacc agtgccgttc   3180
cggtgctcac cgcgcgcgac gtcgccggag cggtcgagtt ctggaccgac cggctcgggt   3240
tctcccggga cttcgtggag gacgacttcg ccggtgtggt ccgggacgac gtgaccctgt   3300
tcatcagcgc ggtccaggac caggtggtgc cggacaacac cctggcctgg gtgtgggtgc   3360
gcggcctgga cgagctgtac gccgagtggt cggaggtcgt gtccacgaac ttccgggacg   3420
cctccgggcc ggccatgacc gagatcggcg agcagccgtg ggggcgggag ttcgccctgc   3480
gcgacccggc cggcaactgc gtgcacttcg tggccgagga gcaggactga cacgtgctac   3540
gagatttcga ttccaccgcc gccttctatg aaaggttggg cttcggaatc gttttccggg   3600
acgccggctg gatgatcctc cagcgcgggg atctcatgct ggagttcttc gcccacccca   3660
acttgtttat tgcagcttat aatggttaca aataaagcaa tagcatcaca aatttcacaa   3720
ataaagcatt tttttcactg cattctagtt gtggtttgtc caaactcatc aatgtatctt   3780
atcatgtctg aattcccggg gatcctctag agtcgacctg caggcatgca agcttggcac   3840
tggccgtcgt tttacaacgt cgtgactggg aaaaccctgg cgttacccaa cttaatcgcc   3900
ttgcagcaca tccccctttc gccagctggc gtaatagcga agaggcccgc accgatcgcc   3960
cttcccaaca gttgcgcagc ctgaatggcg aatggcgcct gatgcggtat tttctcctta   4020
cgcatctgtg cggtatttca caccgcatat atggtgcact ctcagtacaa tctgctctga   4080
tgccgcatag ttaagccagc ccgacaccc  gccaacaccc gctgacgcgc cctgacgggc   4140
ttgtctgctc ccggcatccg cttacagaca agctgtgacc gtctccggga gctgcatgtg   4200
tcagaggttt tcaccgtcat caccgaaacg cgcga                              4235

<210> SEQ ID NO 31
<211> LENGTH: 3964
<212> TYPE: DNA
<213> ORGANISM: Thraustochytrium sp.

<400> SEQUENCE: 31
gacgaaaggg cctcgtgata cgcctatttt tataggttaa tgtcatgata ataatggttt     60
```

-continued

```
cttagacgtc aggtggcact tttcggggaa atgtgcgcgg aaccccctatt tgtttatttt      120 tctaaataca ttcaaatatg tatccgctca tgagacaata accctgataa atgcttcaat      180
aatattgaaa aaggaagagt atgagtattc aacatttccg tgtcgccctt attccctttt      240
ttgcggcatt ttgccttcct gttttttgctc acccagaaac gctggtgaaa gtaaaagatg     300
ctgaagatca gttgggtgca cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacgatg      540 gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc attttttaatt taaaaggatc taggtgaaga    1140 tccttttttga taatctcatg accaaaatcc cttaacgtga gttttcgttc cactgagcgt    1200
cagaccccgt agaaaagatc aaaggatctt cttgagatcc ttttttttctg cgcgtaatct    1260 gctgcttgca acaaaaaaa ccaccgctac cagcggtggt ttgtttgccg gatcaagagc      1320
taccaactct ttttccgaag gtaactggct tcagcagagc gcagatacca atactgtcc     1380 ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg tcgggctga acggggggtt     1560 cgtgcacaca gcccagcttg gagcgaacga cctacaccga actgagatac ctacagcgtg    1620
agcattgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttttgtga tgctcgtcag    1800 ggggcggag cctatggaaa aacgccagca acgcggcctt tttacggttc ctggccttttt   1860 gctggccttt tgctcacatg tgtgctgggc ccagccggcc agatctgagc tcgcggccgc    1920
gatatcgcta gacaacgcca tcctcgacca cagcaaggac acgcaccgct tcggctacgg    1980
tatccagatc ggataaatat tataccgccc cttccgctct cctttttcttt tttgctcgtc    2040 tggatgccag actaaggagt ccttgctcct ctgcgcaagg ctgctcaccc agagtctctg    2100
cctgtggttg agcgcccacc aacaggttaa agcgaaccag ggccgccccg ttgccgctgc    2160
gatgtcgctc ctcttgcgag actcttcatt agatcggcgg aatgctgccg caggactgac    2220
cgcctcttcg ttcgttcgtt tgtacgcgag cggtgcgagc ggcttcgttg ttggcagata    2280
ggcagaacgc gagcagttca cgtttctttg cagctttatc tatccgcaaa ttcgcctcag    2340
cgtctgcaac tttccggtga ggacagcaga gctgcagttc tgatcgtctc catcttttgg    2400
```

| | |
|---|---:|
| agcgcatgtc gacgtccccc agctcgtctc cgtctcccct ggagtggacg gtctctttca | 2460 |
| cagtgcctgg gtgcggccat ttccctaaat aggttgcgca gccgagtttc cttaaacgtg | 2520 |
| cctggtccgc gtgcttccgc cttactacct gaacgcgcag tagctcggcg cgtgccgctt | 2580 |
| taaggcgggc ggggtggctg ctcttgctta cgccaggcgc gtacgtcagc agcgccggcg | 2640 |
| ccatgctgcc catagcggcc acagaatcgt aggcgctgca atcgggaact gccaagatgg | 2700 |
| caatcgagac gatcccccaa aagtggacaa gcaccgtcaa agtaacctgg ctgatgatgg | 2760 |
| ccgggaccgc ctggtgacgg ccagccggca aaaccggaat ctatcacgag gactgggcag | 2820 |
| atcaagggcc tagtgctagc gagcagctcg agcgaaagaa gcgcgccagc agcgcaggca | 2880 |
| cgccatggcc aagttgacca gtgccgttcc ggtgctcacc gcgcgcgacg tcgccggagc | 2940 |
| ggtcgagttc tggaccgacc ggctcgggtt ctcccgggac ttcgtggagg acgacttcgc | 3000 |
| cggtgtggtc cgggacgacg tgaccctgtt catcagcgcg gtccaggacc aggtggtgcc | 3060 |
| ggacaacacc ctggcctggg tgtgggtgcg cggcctggac gagctgtacg ccgagtggtc | 3120 |
| ggaggtcgtg tccacgaact tccgggacgc ctccgggccg ccatgaccg agatcggcga | 3180 |
| gcagccgtgg gggcgggagt tcgccctgcg cgacccggcc ggcaactgcg tgcacttcgt | 3240 |
| ggccgaggag caggactgac acgtgctacg agatttcgat tccaccgccg ccttctatga | 3300 |
| aaggttgggc ttcggaatcg ttttccggga cgccggctgg atgatcctcc agcgcgggga | 3360 |
| tctcatgctg gagttcttcg cccaccccaa cttgttatt gcagcttata atggttacaa | 3420 |
| ataaagcaat agcatcacaa atttcacaaa taaagcattt ttttcactgc attctagttg | 3480 |
| tggtttgtcc aaactcatca atgtatctta tcatgtctga attcccgggg atcctctaga | 3540 |
| gtcgacctgc aggcatgcaa gcttggcact ggccgtcgtt ttacaacgtc gtgactggga | 3600 |
| aaaccctggc gttacccaac ttaatcgcct tgcagcacat ccccctttcg ccagctggcg | 3660 |
| taatagcgaa gaggcccgca ccgatcgccc ttcccaacag ttgcgcagcc tgaatggcga | 3720 |
| atggcgcctg atgcggtatt ttctccttac gcatctgtgc ggtatttcac accgcatata | 3780 |
| tggtgcactc tcagtacaat ctgctctgat gccgcatagt taagccagcc ccgacacccg | 3840 |
| ccaacacccg ctgacgcgcc ctgacgggct tgtctgctcc cggcatccgc ttacagacaa | 3900 |
| gctgtgaccg tctccgggag ctgcatgtgt cagaggtttt caccgtcatc accgaaacgc | 3960 |
| gcga | 3964 |

<210> SEQ ID NO 32
<211> LENGTH: 4319
<212> TYPE: DNA
<213> ORGANISM: Thraustochytrium sp.

<400> SEQUENCE: 32

| | |
|---|---:|
| gacgaaaggg cctcgtgata cgcctatttt tataggttaa tgtcatgata ataatggttt | 60 |
| cttagacgtc aggtggcact tttcggggaa atgtgcgcgg aaccccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attcccttt | 240 |
| ttgcggcatt ttgccttcct gttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |

```
gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc attttttaatt taaaaggatc taggtgaaga    1140
tcctttttga taatctcatg accaaaatcc cttaacgtga gttttcgttc cactgagcgt    1200 cagacccgt agaaaagatc aaaggatctt cttgagatcc ttttttttctg cgcgtaatct    1260 gctgcttgca aacaaaaaaa ccaccgctac cagcggtggt ttgtttgccg gatcaagagc    1320
taccaactct ttttccgaag gtaactggct tcagcagagc gcagatacca atactgtcc     1380 ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga cgggggggtt    1560
cgtgcacaca gcccagcttg gagcgaacga cctacaccga actgagatac ctacagcgtg    1620
agcattgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttttgtga tgctcgtcag    1800 gggggcggag cctatggaaa aacgccagca acgcggcctt tttacggttc ctggccttt     1860 gctggccttt tgctcacatg tgtgctgggc ccagccggcc agatctgagc tcgcggccgc    1920
gatatcgcta gacaacgcca tcctcgacca cagcaaggac acgcaccgct tcggctacgg    1980
tatccagatc ggataaatat tataccgccc cttccgctct cctttttctttt tttgctcgtc    2040 tggatgccag actaaggagt ccttgctcct ctgcgcaagg ctgctcaccc agagtctctg    2100
cctgtggttg agcgcccacc aacaggttaa agcgaaccag ggccgccccg ttgccgctgc    2160
gatgtcgctg ctcttgcgag actcttcatt agatcggcgg aatgctgccg caggactgac    2220
cgcctcttcg ttcgttcgtt tgtacgcgag cggtgcgagc ggcttcgttg ttggcagata    2280
ggcagaacgc gagcagttca cgtttctttg cagctttatc tatccgcaaa ttcgcctcag    2340
cgtctgcaac tttccggtga ggacagcaga gctgcagttc tgatcgtctc catcttttgg    2400
agcgcatgtc gacgtccccc agctcgtctc cgtctcccct ggagtggacg gtctctttca    2460
cagtgcctgg gtgcggccat ttccctaaat aggttgcgca gccagagttc cttaaacgtg    2520
cctggtccgc gtgcttccgc cttactacct gaacgcgcag tagctcggcg cgtgccgctt    2580
taaggcgggc ggggtggctg ctcttgctta cgccaggcgc gtacgtcagc agcgccggcg    2640
ccatgctgcc catagcggcc acagaatcgt aggcgctgca atcgggaact gccaagatgg    2700
caatcgagac gatccccccaa aagtggacaa gcaccgtcaa agtaacctgg ctgatgatgg    2760
ccgggaccgc ctggtgacgg ccagccggca aaaccggaat ctatcacgag gactgggcag    2820
atcaagggcc tagtgctagc gagcagctcg agcgaaagaa gcgcgccagc agcgcaggca    2880
```

```
cgatgagtaa aggagaagaa cttttcactg gagttgtccc aattcttgtt gaattagatg    2940
gtgatgttaa tgggcacaaa ttttctgtca gtggagaggg tgaaggtgat gcaacatacg    3000
gaaaacttac ccttaaattt atttgcacta ctggaaaact acctgttcca tggccaacac    3060
ttgtcactac tttcacttat ggtgttcaat gcttttcaag atacccagat catatgaagc    3120
ggcacgactt cttcaagagc gccatgcctg agggatacgt gcaggagagg accatctctt    3180
tcaaggacga cgggaactac aagacacgtg ctgaagtcaa gtttgaggga cacaccctcg    3240
tcaacaggat cgagcttaag ggaatcgatt tcaaggagga cggaaacatc ctcggccaca    3300
agttggaata caactacaac tcccacaacg tatacatcac ggcagacaaa caaaagaatg    3360
gaatcaaagc taacttcaaa attagacaca acattgaaga tggaagcgtt caactagcag    3420
accattatca acaaaatact ccaattggcg atggccctgt ccttttacca gacaaccatt    3480
acctgtccac acaatctgcc ctttcgaaag atcccaacga aaagagagac cacatggtcc    3540
ttcttgagtt tgtaacagct gctgggatta cacatggcat ggatgaacta tacaaataag    3600
gtacctctac gcgtcacgtg ctacgagatt tcgattccac cgccgccttc tatgaaaggt    3660
tgggcttcgg aatcgttttc cgggacgccg gctggatgat cctccagcgc ggggatctca    3720
tgctggagtt cttcgcccac cccaacttgt ttattgcagc ttataatggt tacaaataaa    3780
gcaatagcat cacaaatttc acaaataaag cattttttc actgcattct agttgtggtt    3840
tgtccaaact catcaatgta tcttatcatg tctgaattcc cggggatcct ctagagtcga    3900
cctgcaggca tgcaagcttg gcactggccg tcgttttaca acgtcgtgac tgggaaaacc    3960
ctggcgttac ccaacttaat cgccttgcag cacatcccccc tttcgccagc tggcgtaata    4020
gcgaagaggc ccgcaccgat cgcccttccc aacagttgcg cagcctgaat ggcgaatggc    4080
gcctgatgcg gtattttctc cttacgcatc tgtgcggtat ttcacaccgc atatatggtg    4140
cactctcagt acaatctgct ctgatgccgc atagttaagc cagccccgac acccgccaac    4200
acccgctgac gcgccctgac gggcttgtct gctcccggca tccgcttaca gacaagctgt    4260
gaccgtctcc gggagctgca tgtgtcagag gttttcaccg tcatcaccga aacgcgcga    4319
```

<210> SEQ ID NO 33
<211> LENGTH: 78
<212> TYPE: DNA
<213> ORGANISM: Artificial sequence
<220> FEATURE:
<223> OTHER INFORMATION: Synthetic oligonucleotide

<400> SEQUENCE: 33

```
gagcagctcg agcgaaagaa gcgcgccagc agcgcaggca cgatgagtaa aggagaagaa    60
cttttcactg gagttgtc                                                 78
```

<210> SEQ ID NO 34
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 34

```
gtgacgcgta gaggtacctt atttgtatag ttcatccatg ccatgtgtaa tccc          54
```

<210> SEQ ID NO 35
<211> LENGTH: 7032
<212> TYPE: DNA
<213> ORGANISM: Thraustochytrium sp. ONC-T18

<400> SEQUENCE: 35

```
agctgtttcc tgtgtgaaat tgttatccgc tcacaattcc acacaacata cgagccggaa    60
gcataaagtg taaagcctgg ggtgcctaat gagtgagcta actcacatta attgcgttgc   120
gctcactgcc cgctttccag tcgggaaacc tgtcgtgcca gctgcattaa tgaatcggcc   180
aacgcgcggg gagaggcggt ttgcgtattg ggcgctcttc cgcttcctcg ctcactgact   240
cgctgcgctc ggtcgttcgg ctgcggcgag cggtatcagc tcactcaaag gcggtaatac   300
ggttatccac agaatcaggg gataacgcag gaaagaacat gtgagcaaaa ggccagcaaa   360
aggccaggaa ccgtaaaaag gccgcgttgc tggcgttttt ccataggctc cgccccctg   420
acgagcatca caaaaatcga cgctcaagtc agaggtggcg aaacccgaca ggactataaa   480
gataccaggc gtttccccct ggaagctccc tcgtgcgctc tcctgttccg accctgccgc   540
ttaccggata cctgtccgcc tttctccctt cgggaagcgt ggcgctttct catagctcac   600
gctgtaggta tctcagttcg gtgtaggtcg ttcgctccaa gctgggctgt gtgcacgaac   660
cccccgttca gcccgaccgc tgcgccttat ccggtaacta tcgtcttgag tccaacccgg   720
taagacacga cttatcgcca ctggcagcag ccactggtaa caggattagc agagcgaggt   780
atgtaggcgg tgctacagag ttcttgaagt ggtggcctaa ctacggctac actagaagga   840
cagtatttgg tatctgcgct ctgctgaagc cagttacctt cggaaaaaga gttggtagct   900
cttgatccgg caaacaaacc accgctggta gcggtggttt ttttgtttgc aagcagcaga   960
ttacgcgcag aaaaaaagga tctcaagaag atcctttgat cttttctacg ggtctgacg  1020
ctcagtggaa cgaaaactca cgttaaggga ttttggtcat gaattaattc ttagaaaaac  1080
tcatcgagca tcaaatgaaa ctgcaattta ttcatatcag gattatcaat accatatttt  1140
tgaaaagcc gtttctgtaa tgaaggagaa aactcaccga gcagttcca taggatgga  1200
agatcctggt atcggtctgc gattccgact cgtccaacat caatacaacc tattaatttc  1260
ccctcgtcaa aaataaggtt atcaagtgag aaatcaccat gagtgacgac tgaatccggt  1320
gagaatggca aaagtttatg catttctttc cagacttgtt caacaggcca gccattacgc  1380
tcgtcatcaa aatcactcgc atcaaccaaa ccgttattca ttcgtgattg cgcctgagcg  1440
agacgaaata cgcgatcgct gttaaaagga cattacaaa caggaatcga atgcaaccgg  1500
cgcaggaaca ctgccagcgc atcaacaata ttttcacctg aatcaggata ttcttctaat  1560
acctggaatg ctgttttccc ggggatcgca gtggtgagta accatgcatc atcaggagta  1620
cggataaaat gcttgatggt cggaagaggc ataaattccg tcagccagtt tagtctgacc  1680
atctcatctg taacatcatt ggcaacgcta cctttgccat gtttcagaaa caactctggc  1740
gcatcgggct tcccatacaa tcgatagatt gtcgcacctg attgcccgac attatcgcga  1800
gcccatttat acccatataa atcagcatcc atgttggaat ttaatcgcgg cctagagcaa  1860
gacgtttccc gttgaatatg gctcataaca ccccttgtat tactgtttat gtaagcagac  1920
agttttattg ttcatgagat tatcaaaaag gatcttcacc tagatccttt taaattaaaa  1980
atgaagtttt aaatcaatct aaagtatata tgagtaaact tggtctgaca gttaccaatg  2040
cttaatcagt gaggcaccta tctcagcgat ctgtctattt cgttcatcca tagttgcctg  2100
actccccgtc gtgtagataa ctacgatacg ggagggctta ccatctggcc ccagtgctgc  2160
aatgataccg cgagacccac gctcaccggc tccagattta tcagcaataa accagccagc  2220
cggaagggcc gagcgcagaa gtggtcctgc aactttatcc gcctccatcc agtctattaa  2280
```

```
ttgttgccgg gaagctagag taagtagttc gccagttaat agtttgcgca acgttgttgc    2340
cattgctaca ggcatcgtgg tgtcacgctc gtcgtttggt atggcttcat tcagctccgg    2400
ttcccaacga tcaaggcgag ttacatgatc ccccatgttg tgcaaaaaag cggttagctc    2460
cttcggtcct ccgatcgttg tcagaagtaa gttggccgca gtgttatcac tcatggttat    2520
ggcagcactg cataattctc ttactgtcat gccatccgta agatgctttt ctgtgactgg    2580
tgagtactca accaagtcat tctgagaata gtgtatgcgg cgaccgagtt gctcttgccc    2640
ggcgtcaata cgggataata ccgcgccaca tagcagaact ttaaaagtgc tcatcattgg    2700
aaaacgttct cgggggcgaa aactctcaag gatcttaccg ctgttgagat ccagttcgat    2760
gtaacccact cgtgcaccca actgatcttc agcatctttt actttcacca gcgtttctgg    2820
gtgagcaaaa acaggaaggc aaaatgccgc aaaaaaggga ataagggcga cacggaaatg    2880
ttgaatactc atactcttcc tttttcaata ttattgaagc atttatcagg gttattgtct    2940
catgagcgga tacatatttg aatgtattta gaaaaataaa caataggggg ttccgcgcac    3000
atttccccga aaagtgccac ctgacgcgcc ctgtagcggc gcattaagcg cggcgggtgt    3060
ggtggttacg cgcagcgtga ccgctacact tgccagcgcc ctagcgcccg ctcctttcgc    3120
tttcttccct tcctttctcg ccacgttcgc cggctttccc cgtcaagctc taaatcgggg    3180
gctcccttta gggttccgat ttagtgcttt acggcacctc gaccccaaaa aacttgatta    3240
gggtgatggt tcacgtagtg gccatcgccc tgatagacg gttttcgcc ctttgacgtt    3300 ggagtccacg ttctttaata gtggactctt gttccaaact ggaacaacac tcaaccctat    3360
ctcggtctat tcttttgatt tataagggat tttgccgatt tcggcctatt ggttaaaaaa    3420
tgagctgatt taacaaaaat ttaacgcgaa ttttaacaaa atattaacgc ttacaatttc    3480
cattcgccat tcaggctgcg caactgttgg gaagggcgat cggtgcgggc ctcttcgcta    3540
ttacgccagc tggcgaaagg gggatgtgct gcaaggcgat taagttgggt aacgccaggg    3600
ttttcccagt cacgacgttg taaaacgacg gccagtgaat tgtgcggccg cgagctcggg    3660
cccccacacg tgtggtctag agctagccta ggctcgagaa gcttggcctg tctcccttgg    3720
ccatccattg cgctgcggaa gcattggatt gcgaactgcg tcggccagat cgcttggttt    3780
cccaacatga gacgcgctct gtcggcaaga ccatttccgc ccccggcttt gctcacaacc    3840
aactcgtagt agatttttgta aagaacactg cacgtctgac tgctcccagc ccgcacgcat    3900
tgcgcttggc agcctcggtc ccaaaccgtc acggtcgctg cccggtccac gggaaaaaat    3960
aacttttgtc cgcgagcggc cgttcaaggc gcagccgcga gcgtgccaac cgtccgtccc    4020
gcattctttt cccaatgttg gattcattca ttcttgccag gccagatcat ctgtgcctcc    4080
ctcgcgtgcc cttccttagc gtgcgcagat ctcttcttcc cagagcccgc gcggcgcttc    4140
gtggagtcgg cgtccatgtc atgcgcgcgc ggcgtcttga ccccctcggc cccttttggtt    4200 cgcggctgcg caacgagccg tttcacgcca ttgcgaccaa ccgcgcgcta aaatcggatt    4260
ggccgttgca cgccgatttt gcagcacctc tgggctgtga gggacgaccg tccactttta    4320
cccgcacaga gtggactttc accccctcac tccactgaag ccaactttc gccgtcttcc    4380 caacccaaag tttatgctag ccctcatgcc gcaacgacg tcaccccat ttccactggc    4440 gacgtgggga cctgggcgca ataaggcgcg agaaggaaat tacgacggca cactggggcc    4500
agaagagggc actaggagcg gcaacccact ggcgcggcac agcggtttgg cgcggggatc    4560
aaagcaaaac ccggctcatc cagagcaaac ccgaatcagc cttcagacgg tcgtgcctaa    4620
caacacgccg ttctaccccg ccttccttgc gtccctcgcc tccccgagc ccaagtcttc    4680
```

```
cgcccgctcc taacgccaac caagcaagat ggccaagttg accagtgccg ttccggtgct   4740
caccgcgcgc gacgtcgccg gagcggtcga gttctggacc gaccggctcg ggttctcccg   4800
ggacttcgtg gaggacgact cgccggtgt ggtccgggac gacgtgaccc tgttcatcag    4860
cgcggtccag gaccaggtgg tgccggacaa caccctggcc tgggtgtggg tgcgcggcct   4920
ggacgagctg tacgccgagt ggtcggaggt cgtgtccacg aacttccggg acgcctccgg   4980
gccggccatg accgagatcg gcgagcagcc gtggggcgg gagttcgccc tgcgcgaccc    5040
ggccggcaac tgcgtgcact tcgtggccga ggagcaggac taacacgtgc tacgagattt   5100
cgattccacc gccgccttct atgaaaggtt gggcttcgga atcgttttcc gggacgccgg   5160
ctggatgatc ctccagcgcg gggatctcat gctggagttc ttcgcccacc ccaacttgtt   5220
tattgcagct tataatggtt acaaataaag caatagcatc acaaatttca caataaagc    5280 atttttttca ctgcattcta gttgtggttt gtccaaactc atcaatgtat cttatcatgt   5340
ctgagggccc gactgttcgg gagggccgca cttattagag ttgaagccaa gtaagatggt   5400
gagtcatgat aattgagcag atcgcttgtt tggagcgatg aatcgtttga gtttctgccc   5460
catcagttgt cgacggtagt gtattggact acggtgacta taacgggtga cggggagtta   5520
gggctcgact ccggagaggg agcctgagag acggctacca catccaagga aggcagcagg   5580
cgcgtaaatt acccaatgtg gactccacga ggtagtgacg agaaatatca atgcggggcg   5640
cttcgcgtct tgctattgga atgagagcaa tgtaaaaccc tcatcgagga tcaactggag   5700
ggcaagtctg gtgccagcag ccgcggtaat tccagctcca gaagcgtatg ctaaagttgt   5760
tgcagttaaa aagctcgtag ttgaatttct ggggcgggag ccccggtctt tgcgcgactg   5820
cgctctgttt gccgagcggc tcctctgcca tcctcgcctc tttttttagt ggcgtcgttc   5880
actgtaatta aagcagagtg ttccaagcag gtcgtatgac ctggatgttt attatgggat   5940
gatcagatag ggctcgggtg ctattttgtt ggtttgcaca tctgagtaat gatgaatagg   6000
aacagttggg ggtattcgta tttaggagct agaggtgaaa ttcttggatt tccgaaagac   6060
gaactacagc gaaggcattt accaagcatg ttttcattaa tcaagaacga agtctgggg   6120 atcgaagatg attagatacc atcgtagtct agaccgtaaa cgatgccgac ttgcgattgc   6180
ggggtgtttg tattggaccc tcgcagcagc acatgagaaa tcaaagtctt tgggttccgg   6240
ggggagtatg gtcgcaaggc tgaaacttaa aggaattgac ggaagggcac caccaggagt   6300
ggagcctgcg gcttaatttg actcaacacg ggaaaactta ccaggtccag acataggtag   6360
gattgacaga ttgagagctc tttcttgatt ctatgggtgg tggtgcatgg ccgttcttag   6420
ttggtggagt gatttgtctg gttaattccg ttaacgaacg agacctcggc ctactaaata   6480
gcggtgggta tggcgacata cttgcgtacg cttcttagag ggacatgttc ggtatacgag   6540
caggaagttc gaggcaataa caggtctgtg atgcccttag atgttctggg ccgcacgcgc   6600
gctacactga tgggttcaac gggtggtcat cgttgttcgc agcgaggtgc tttgccggaa   6660
ggcatggcaa atcctttcaa cgcccatcgt gctgggcta gattttttgca attattaatc    6720 tccaacgagg aattcctagt aaacgcaagt catcagcttg cattgaatac gtccctgccc   6780
tttgtacaca ccgcccgtcg cacctaccga ttgaacggtc cgatgaaacc atgggatgac   6840
cttttgagcg tttgttcgcg aggggggtca gaactcgggt gaatcttatt gtttagagga   6900
aggtgaagtc gtaacaaggt ttccgtagtg aatcacgaat tctggatccg atacgtaacg   6960
cgtctgcagc atgcgtggta ccgagctttc cctatagtga gtcgtattag agcttggcgt   7020
```
aatcatggtc at       7032

<210> SEQ ID NO 36
<211> LENGTH: 53
<212> TYPE: DNA
<213> ORGANISM: Artificial sequence
<220> FEATURE:
<223> OTHER INFORMATION: Synthetic oligonucleotide

<400> SEQUENCE: 36
ggtctagagc tagcctaggc tcgagaagct tggcctgtct cccttggcca tcc       53

<210> SEQ ID NO 37
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 37
ggaacggcac tggtcaactt ggccatcttg cttggttggc gttaggagcg g       51

<210> SEQ ID NO 38
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 38
ccgctcctaa cgccaaccaa gcaagatggc caagttgacc agtgccgttc c       51

<210> SEQ ID NO 39
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 39
ggccctcccg aacagtcggg ccctcagaca tgataagata cattgatgag tttgg       55

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
ggccaagttg accagtgccg       20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
cagtcctgct cctcggccac       20

<210> SEQ ID NO 42
<211> LENGTH: 19
<212> TYPE: DNA
<213> ORGANISM: Artificial sequence

```
<220> FEATURE:
<223> OTHER INFORMATION: Synthetic oligonucleotide

<400> SEQUENCE: 42
catgaccgag atcggcgag                                                19

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ccgtcgacaa ctgatggggc                                               20

<210> SEQ ID NO 44
<211> LENGTH: 7360
<212> TYPE: DNA
<213> ORGANISM: Thraustochytrium sp. ONC-T18

<400> SEQUENCE: 44
agctgtttcc tgtgtgaaat tgttatccgc tcacaattcc acacaacata cgagccggaa      60
gcataaagtg taaagcctgg ggtgcctaat gagtgagcta actcacatta attgcgttgc     120
gctcactgcc cgctttccag tcgggaaacc tgtcgtgcca gctgcattaa tgaatcggcc     180
aacgcgcggg gagaggcggt ttgcgtattg ggcgctcttc cgcttcctcg ctcactgact     240
cgctgcgctc ggtcgttcgg ctgcggcgag cggtatcagc tcactcaaag gcggtaatac     300
ggttatccac agaatcaggg gataacgcag gaaagaacat gtgagcaaaa ggccagcaaa     360
aggccaggaa ccgtaaaaag gccgcgttgc tggcgttttt ccataggctc cgcccccctg     420
acgagcatca caaaaatcga cgctcaagtc agaggtggcg aaacccgaca ggactataaa     480
gataccaggc gtttccccct ggaagctccc tcgtgcgctc tcctgttccg accctgccgc     540
ttaccggata cctgtccgcc tttctccctt cgggaagcgt ggcgctttct catagctcac     600
gctgtaggta tctcagttcg gtgtaggtcg ttcgctccaa gctgggctgt gtgcacgaac     660 ccccgttca gcccgaccgc tgcgccttat ccggtaacta tcgtcttgag tccaacccgg     720
taagacacga cttatcgcca ctggcagcag ccactggtaa caggattagc agagcgaggt     780
atgtaggcgg tgctacagag ttcttgaagt ggtggcctaa ctacggctac actagaagga     840
cagtatttgg tatctgcgct ctgctgaagc cagttacctt cggaaaaaga gttggtagct     900
cttgatccgg caaacaaacc accgctggta gcggtggttt ttttgtttgc aagcagcaga     960
ttacgcgcag aaaaaaagga tctcaagaag atcctttgat cttttctacg ggtctgacg     1020 ctcagtggaa cgaaaactca cgttaaggga ttttggtcat gaattaattc ttagaaaaac    1080
tcatcgagca tcaaatgaaa ctgcaattta ttcatatcag gattatcaat accatatttt    1140
tgaaaaagcc gtttctgtaa tgaaggagaa aactcaccga gcagttccat aggatggca     1200 agatcctggt atcggtctgc gattccgact cgtccaacat caatacaacc tattaatttc    1260
ccctcgtcaa aaataaggtt atcaagtgag aaatcaccat gagtgacgac tgaatccggt    1320
gagaatggca aaagtttatg catttctttc cagacttgtt caacaggcca gccattacgc    1380
tcgtcatcaa aatcactcgc atcaaccaaa ccgttattca ttcgtgattg cgcctgagcg    1440
agacgaaata cgcgatcgct gttaaaagga caattacaaa caggaatcga atgcaaccgg    1500
cgcaggaaca ctgccagcgc atcaacaata ttttcacctg aatcaggata ttcttctaat    1560
```

```
acctggaatg ctgttttccc ggggatcgca gtggtgagta accatgcatc atcaggagta    1620
cggataaaat gcttgatggt cggaagaggc ataaattccg tcagccagtt tagtctgacc    1680
atctcatctg taacatcatt ggcaacgcta cctttgccat gtttcagaaa caactctggc    1740
gcatcgggct tcccatacaa tcgatagatt gtcgcacctg attgcccgac attatcgcga    1800
gcccatttat acccatataa atcagcatcc atgttggaat taatcgcgg cctagagcaa     1860
gacgtttccc gttgaatatg gctcataaca cccttgtat tactgtttat gtaagcagac     1920
agttttattg ttcatgagat tatcaaaaag gatcttcacc tagatccttt taaattaaaa    1980
atgaagtttt aaatcaatct aaagtatata tgagtaaact tggtctgaca gttaccaatg    2040
cttaatcagt gaggcaccta tctcagcgat ctgtctattt cgttcatcca tagttgcctg    2100
actccccgtc gtgtagataa ctacgatacg ggagggctta ccatctggcc ccagtgctgc    2160
aatgataccg cgagacccac gctcaccggc tccagattta tcagcaataa accagccagc    2220
cggaagggcc gagcgcagaa gtggtcctgc aactttatcc gcctccatcc agtctattaa    2280
ttgttgccgg gaagctagag taagtagttc gccagttaat agtttgcgca acgttgttgc    2340
cattgctaca ggcatcgtgg tgtcacgctc gtcgtttggt atggcttcat tcagctccgg    2400
ttcccaacga tcaaggcgag ttacatgatc ccccatgttg tgcaaaaaag cggttagctc    2460
cttcggtcct ccgatcgttg tcagaagtaa gttggccgca gtgttatcac tcatggttat    2520
ggcagcactg cataattctc ttactgtcat gccatccgta agatgctttt ctgtgactgg    2580
tgagtactca accaagtcat tctgagaata gtgtatgcgg cgaccgagtt gctcttgccc    2640
ggcgtcaata cgggataata ccgcgccaca tagcagaact ttaaaagtgc tcatcattgg    2700
aaaacgttct cggggcgaaa actctcaag gatcttaccg ctgttgagat ccagttcgat    2760
gtaacccact cgtgcaccca actgatcttc agcatctttt actttcacca gcgtttctgg    2820
gtgagcaaaa acaggaaggc aaaatgccgc aaaaaaggga ataagggcga cacggaaatg    2880
ttgaatactc atactcttcc tttttcaata ttattgaagc atttatcagg gttattgtct    2940
catgagcgga tacatatttg aatgtattta gaaaaataaa caaatagggg ttccgcgcac    3000
atttccccga aaagtgccac ctgacgcgcc ctgtagcggc gcattaagcg cggcgggtgt    3060
ggtggttacg cgcagcgtga ccgctacact tgccagcgcc ctagcgcccg ctcctttcgc    3120
tttcttccct tcctttctcg ccacgttcgc cggctttccc cgtcaagctc taaatcgggg    3180
gctcccttta gggttccgat ttagtgcttt acggcacctc gaccccaaaa aacttgatta    3240
gggtgatggt tcacgtagtg ggccatcgcc ctgatagacg gttttcgcc ctttgacgtt     3300
ggagtccacg ttctttaata gtggactctt gttccaaact ggaacaacac tcaaccctat    3360
ctcggtctat tcttttgatt tataagggat tttgccgatt tcggcctatt ggttaaaaaa    3420
tgagctgatt taacaaaaat ttaacgcgaa ttttaacaaa atattaacgc ttacaatttc    3480
cattcgccat tcaggctgcg caactgttgg gaagggcgat cggtgcgggc ctcttcgcta    3540
ttacgccagc tggcgaaagg gggatgtgct gcaaggcgat taagttgggt aacgccaggg    3600
ttttcccagt cacgacgttg taaaacgacg gccagtgaat tgtgcggccg cgagctcggg    3660
cccccacacg tgtggtctag agctagccta ggctcgagaa gcttggcctg tctcccttgg    3720
ccatccattg cgctgcggaa gcattggatt gcgaactgcg tcggccagat cgcttggttt    3780
cccaacatga acgcgctct gtcggcaaga ccatttccgc cccggctttt gctcacaacc     3840
aactcgtagt agatttgta aagaacactg cacgtctgac tgctcccagc ccgcacgcat     3900
tgcgcttggc agcctcggtc ccaaaccgtc acggtcgctg cccggtccac gggaaaaaat    3960
```

```
aacttttgtc cgcgagcggc cgttcaaggc gcagccgcga gcgtgccaac cgtccgtccc   4020
gcattctttt cccaatgttg gattcattca ttcttgccag gccagatcat ctgtgcctcc   4080
ctcgcgtgcc cttccttagc gtgcgcagat ctcttcttcc cagagcccgc gcggcgcttc   4140
gtggagtcgg cgtccatgtc atgcgcgcgc ggcgtcttga cccctcggc ccctttggtt    4200 cgcggctgcg caacgagccg tttcacgcca ttgcgaccaa ccgcgcgcta aaatcggatt   4260
ggccgttgca cgccgatttt gcagcacctc tgggctgtga gggacgaccg tccacttta    4320 cccgcacaga gtggactttc accccctcac tccactgaag ccaactttc gccgtcttcc    4380 caacccaaag tttatgctag ccctcatgcc gcaacgacg tcaccccat ttccactggc     4440 gacgtgggga cctgggcgca ataaggcgcg agaaggaaat tacgacggca cactggggcc   4500
agaagagggc actaggagcg gcaacccact ggcgcggcac agcggtttgg cgcggggatc   4560
aaagcaaaac ccggctcatc cagagcaaac ccgaatcagc cttcagacgg tcgtgcctaa   4620
caacacgccg ttctacccg ccttccttgc gtccctcgcc tcccccgagc caagtcttc    4680 cgcccgctcc taacgccaac caagcaagat ggccaagttg accagtgccg ttccggtgct   4740
caccgcgcgc gacgtcgccg gagcggtcga gttctggacc gaccggctcg ggttctcccg   4800
ggacttcgtg gaggacgact cgccggtgt ggtccgggac gacgtgaccc tgttcatcag    4860
cgcggtccag gaccaggtgg tgccggacaa caccctggcc tgggtgtggg tgcgcggcct   4920
ggacgagctg tacgccgagt ggtcggaggt cgtgtccacg aacttccggg acgcctccgg   4980
gccggccatg accgagatcg gcgagcagcc gtggggcgg gagttcgccc tgcgcgaccc    5040
ggccggcaac tgcgtgcact tcgtggccga ggagcaggac taaatgcatt cgcatggctc   5100
cgcaccacca cacaccaccg cccctcttct ttccttgctc actcgatcca tagccactta   5160 cctgccccctt ccctctacca ctgccacgtg cggcgtatga gcgcgcttgc acccgcaacc   5220
ttctctctag ttgttcacaa ttacacccgc tatcaatact cacgcattca tcttcccctt   5280
tttttctact ttacgtaccg gtgctcactt acttacacct gcccgccttg ttcattcatt   5340
cttctcgatg acaacggcag gctctgcttg cggcgcgcgc acgcatccct tactccgccg   5400
cgcaccgaca agcctgcgca aaaaacaaaa aaaacttatc ttcgctcgcg gctccgatgt   5460
cgcggcggcg tgcgagaccg cgccgagttc cgcccgccat gcgatcgaga gtctctctcg   5520
taggagcggg accgcgagcg acttcggtgc ctccgatagc cagctgggct tctagaccgg   5580
ctgggggacc gcccgcggcg tacctctgcg cttcggtggc ccttaaaagg ctgatcgtgg   5640
aaaaggtcgc tctccagtct gcggtttagc ggagggcccg actgttcggg agggccgcac   5700
ttattagagt tgaagccaag taagatggtg agtcatgata attgagcaga tcgcttgttt   5760
ggagcgatga atcgtttgag tttctgcccc atcagttgtc gacggtagtg tattggacta   5820
cggtgactat aacgggtgac ggggagttag ggctcgactc cggagaggga gcctgagaga   5880
cggctaccac atccaaggaa ggcagcaggc gcgtaaatta cccaatgtgg actccacgag   5940
gtagtgacga gaaatatcaa tgcggggcgc ttcgcgtctt gctattggaa tgagagcaat   6000
gtaaaaccct catcgaggat caactggagg gcaagtctgg tgccagcagc cgcggtaatt   6060
ccagctccaa aagcgtatgc taaagttgtt gcagttaaaa agctcgtagt tgaatttctg   6120
gggcgggagc cccggtcttt gcgcgactgc gctctgtttg ccgagcggct cctctgccat   6180
cctcgcctct ttttttagtg gcgtcgttca ctgtaattaa agcagagtgt tccaagcagg   6240
tcgtatgacc tggatgttta ttatgggatg atcagatagg gctcgggtgc tattttgttg   6300
```

```
gtttgcacat ctgagtaatg atgaatagga acagttgggg gtattcgtat ttaggagcta    6360
gaggtgaaat tcttggattt ccgaaagacg aactacagcg aaggcattta ccaagcatgt    6420
tttcattaat caagaacgaa agtctgggga tcgaagatga ttagatacca tcgtagtcta    6480
gaccgtaaac gatgccgact tgcgattgcg gggtgtttgt attggaccct cgcagcagca    6540
catgagaaat caaagtcttt gggttccggg gggagtatgg tcgcaaggct gaaacttaaa    6600
ggaattgacg gaagggcacc accaggagtg gagcctgcgg cttaatttga ctcaacacgg    6660
gaaaacttac caggtccaga cataggtagg attgacagat tgagagctct tcttgattc     6720 tatgggtggt ggtgcatggc cgttcttagt tggtggagtg atttgtctgg ttaattccgt    6780
taacgaacga gacctcggcc tactaaatag cggtgggtat ggcgacatac ttgcgtacgc    6840
ttcttagagg gacatgttcg gtatacgagc aggaagttcg aggcaataac aggtctgtga    6900
tgcccttaga tgttctgggc cgcacgcgcg ctacactgat gggttcaacg ggtggtcatc    6960
gttgttcgca gcgaggtgct tgccggaag gcatggcaaa tcctttcaac gcccatcgtg     7020
ctggggctag attttttgcaa ttattaatct ccaacgagga attcctagta aacgcaagtc   7080
atcagcttgc attgaatacg tccctgccct ttgtacacac cgcccgtcgc acctaccgat    7140
tgaacggtcc gatgaaacca tgggatgacc ttttgagcgt tgttcgcga gggggggtcag    7200 aactcgggtg aatcttattg tttagaggaa ggtgaagtcg taacaaggtt ccgtagtga    7260 atcacgaatt ctggatccga tacgtaacgc gtctgcagca tgcgtggtac cgagctttcc    7320
ctatagtgag tcgtattaga gcttggcgta atcatggtca                         7360

<210> SEQ ID NO 45
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 45
ggtgcggagc catgcgaatg catttagtcc tgctcctcgg ccacgaag                  48

<210> SEQ ID NO 46
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 46
cttcgtggcc gaggagcagg actaaatgca ttcgcatggc tccgcacc                  48

<210> SEQ ID NO 47
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 47
ggccctcccg aacagtcggg ccctccgcta aaccgcagac tggagagcg                 49

<210> SEQ ID NO 48
<211> LENGTH: 7199
<212> TYPE: DNA
<213> ORGANISM: Thraustochytrium sp. ONC-T18

<400> SEQUENCE: 48
```

-continued

```
agctgtttcc tgtgtgaaat tgttatccgc tcacaattcc acacaacata cgagccggaa      60
gcataaagtg taaagcctgg ggtgcctaat gagtgagcta actcacatta attgcgttgc     120
gctcactgcc cgcttccag tcgggaaacc tgtcgtgcca gctgcattaa tgaatcggcc      180
aacgcgcggg gagaggcggt ttgcgtattg ggcgctcttc cgcttcctcg ctcactgact     240
cgctgcgctc ggtcgttcgg ctgcggcgag cggtatcagc tcactcaaag gcggtaatac     300
ggttatccac agaatcaggg gataacgcag gaaagaacat gtgagcaaaa ggccagcaaa     360
aggccaggaa ccgtaaaaag gccgcgttgc tggcgttttt ccataggctc cgcccccctg     420
acgagcatca caaaaatcga cgctcaagtc agaggtggcg aaacccgaca ggactataaa     480
gataccaggc gtttccccct ggaagctccc tcgtgcgctc tcctgttccg accctgccgc     540
ttaccggata cctgtccgcc tttctccctt cgggaagcgt ggcgctttct catagctcac     600
gctgtaggta tctcagttcg gtgtaggtcg ttcgctccaa gctgggctgt gtgcacgaac     660
cccccgttca gcccgaccgc tgcgccttat ccggtaacta tcgtcttgag tccaacccgg     720
taagacacga cttatcgcca ctggcagcag ccactggtaa caggattagc agagcgaggt     780
atgtaggcgg tgctacagag ttcttgaagt ggtggcctaa ctacggctac actagaagga     840
cagtatttgg tatctgcgct ctgctgaagc cagttacctt cggaaaaaga gttggtagct     900
cttgatccgg caaacaaacc accgctggta gcggtggttt ttttgtttgc aagcagcaga     960
ttacgcgcag aaaaaaagga tctcaagaag atcctttgat cttttctacg gggtctgacg    1020
ctcagtggaa cgaaaactca cgttaaggga ttttggtcat gaattaattc ttagaaaaac    1080
tcatcgagca tcaaatgaaa ctgcaattta ttcatatcag gattatcaat accatatttt    1140
tgaaaaagcc gtttctgtaa tgaaggagaa aactcaccga gcagttcca taggatggca    1200 agatcctggt atcggtctgc gattccgact cgtccaacat caatacaacc tattaatttc    1260
ccctcgtcaa aaataaggtt atcaagtgag aaatcaccat gagtgacgac tgaatccggt    1320
gagaatggca aaagtttatg catttctttc cagacttgtt caacaggcca gccattacgc    1380
tcgtcatcaa atcactcgc atcaaccaaa ccgttattca ttcgtgattg cgcctgagcg    1440
agacgaaata cgcgatcgct gttaaaagga caattacaaa caggaatcga atgcaaccgg    1500
cgcaggaaca ctgccagcgc atcaacaata ttttcacctg aatcaggata ttcttctaat    1560
acctggaatg ctgttttccc ggggatcgca gtggtgagta accatgcatc atcaggagta    1620
cggataaaat gcttgatggt cggaagaggc ataaattccg tcagccagtt tagtctgacc    1680
atctcatctg taacatcatt ggcaacgcta ccttttgccat gtttcagaaa caactctggc    1740
gcatcgggct tcccatacaa tcgatagatt gtcgcacctg attgcccgac attatcgcga    1800
gcccatttat acccatataa atcagcatcc atgttgaat ttaatcgcgg cctagagcaa    1860
gacgtttccc gttgaatatg gctcataaca ccccttgtat tactgtttat gtaagcagac    1920
agttttattg ttcatgagat tatcaaaaag gatcttcacc tagatccttt taaattaaaa    1980
atgaagtttt aaatcaatct aaagtatata tgagtaaact tggtctgaca gttaccaatg    2040
cttaatcagt gaggcaccta tctcagcgat ctgtctattt cgttcatcca tagttgcctg    2100
actccccgtc gtgtagataa ctacgatacg ggagggctta ccatctggcc ccagtgctgc    2160
aatgataccg cgagacccac gctcaccggc tccagattta tcagcaataa accagccagc    2220
cggaagggcc gagcgcagaa gtggtcctgc aactttatcc gcctccatcc agtctattaa    2280
ttgttgccgg gaagctagag taagtagttc gccagttaat agtttgcgca acgttgttgc    2340
```

```
cattgctaca ggcatcgtgg tgtcacgctc gtcgtttggt atggcttcat tcagctccgg   2400
ttcccaacga tcaaggcgag ttacatgatc ccccatgttg tgcaaaaaag cggttagctc   2460
cttcggtcct ccgatcgttg tcagaagtaa gttggccgca gtgttatcac tcatggttat   2520
ggcagcactg cataattctc ttactgtcat gccatccgta agatgctttt ctgtgactgg   2580
tgagtactca accaagtcat tctgagaata gtgtatgcgg cgaccgagtt gctcttgccc   2640
ggcgtcaata cggataata ccgcgccaca tagcagaact ttaaaagtgc tcatcattgg   2700
aaaacgttct cgggggcgaa aactctcaag gatcttaccg ctgttgagat ccagttcgat   2760
gtaacccact cgtgcaccca actgatcttc agcatctttt actttcacca gcgtttctgg   2820
gtgagcaaaa acaggaaggc aaaatgccgc aaaaaaggga ataagggcga cacggaaatg   2880
ttgaatactc atactcttcc ttttcaata ttattgaagc atttatcagg gttattgtct   2940
catgagcgga tacatatttg aatgtattta gaaaaataaa caaatagggg ttccgcgcac   3000
atttccccga aaagtgccac ctgacgcgcc ctgtagcggc gcattaagcg cggcgggtgt   3060
ggtggttacg cgcagcgtga ccgctacact tgccagcgcc ctagcgcccg ctcctttcgc   3120
tttcttccct tcctttctcg ccacgttcgc cggctttccc cgtcaagctc taaatcgggg   3180
gctcccttta gggttccgat ttagtgcttt acggcacctc gaccccaaaa aacttgatta   3240
gggtgatggt tcacgtagtg ggccatcgcc ctgatagacg ttttcgcc ctttgacgtt   3300
ggagtccacg ttctttaata gtggactctt gttccaaact ggaacaacac tcaaccctat   3360
ctcggtctat tcttttgatt tataagggat tttgccgatt tcggcctatt ggttaaaaaa   3420
tgagctgatt taacaaaaat ttaacgcgaa ttttaacaaa atattaacgc ttacaatttc   3480
cattcgccat tcaggctgcg caactgttgg gaagggcgat cggtgcgggc ctcttcgcta   3540
ttacgccagc tggcgaaagg gggatgtgct gcaaggcgat taagttgggt aacgccaggg   3600
ttttcccagt cacgacgttg taaaacgacg gccagtgaat tgtgcggccg cgagctcggg   3660
cccccacacg tgtggtctag agctagccta ggctcgagaa gcttggcctg tctcccttgg   3720
ccatccattg cgctgcggaa gcattggatt gcgaactgcg tcggccagat cgcttggttt   3780
cccaacatga gacgcgctct gtcggcaaga ccatttccgc cccggctttt gctcacaacc   3840
aactcgtagt agatttttgta aagaacactg cacgtctgac tgctcccagc ccgcacgcat   3900
tgcgcttggc agcctcggtc ccaaaccgtc acgtcgctg cccggtccac gggaaaaaat   3960
aacttttgtc cgcgagcggc cgttcaaggc gcagccgcga gcgtgccaac cgtccgtccc   4020
gcattctttt cccaatgttg gattcattca ttcttgccag gccagatcat ctgtgcctcc   4080
ctcgcgtgcc cttccttagc gtgcgcagat ctcttcttcc cagagcccgc gcggcgcttc   4140
gtggagtcgg cgtccatgtc atgcgcgcgc ggcgtcttga cccctcggc cccttttggtt   4200
cgcggctgcg caacgagccg tttcacgcca ttgcgaccaa ccgcgcgcta aaatcggatt   4260
ggccgttgca cgccgatttt gcagcacctc tgggctgtga gggacgaccg tccacttta   4320
cccgcacaga gtggactttc accccctcac tccactgaag ccaactttc gccgtcttcc   4380
caacccaaag tttatgctag ccctcatgcc gcaacggacg tcaccccat ttccactggc   4440
gacgtgggga cctgggcgca ataaggcgcg agaaggaaat tacgacggca cactgggcc   4500
agaagagggc actaggagcg gcaacccact ggcgcggcac agcggtttgg cgcggggatc   4560
aaagcaaaac ccggctcatc cagagcaaac ccgaatcagc cttcagacgg tcgtgcctaa   4620
caacacgccg ttctacccg ccttccttgc gtccctcgcc tccccgagc caagtcttc   4680
cgcccgctcc taacgccaac caagcaagat ggccaagttg accagtgccg ttccggtgct   4740
```

```
caccgcgcgc gacgtcgccg gagcggtcga gttctggacc gaccggctcg ggttctcccg   4800
ggacttcgtg gaggacgact tcgccggtgt ggtccgggac gacgtgaccc tgttcatcag   4860
cgcggtccag gaccaggtgg tgccggacaa caccctggcc tgggtgtggg tgcgcggcct   4920
ggacgagctg tacgccgagt ggtcggaggt cgtgtccacg aacttccggg acgcctccgg   4980
gccggccatg accgagatcg gcgagcagcc gtggggcgg gagttcgccc tgcgcgaccc   5040
ggccggcaac tgcgtgcact tcgtggccga ggagcaggac taagcgcctt caggcaggct   5100
gatccctact gtgggggctc tgacggacgg ccggtctttg tacgtaaaca ggcgcttctt   5160
cgcggccccgc cgagggggc ggcaacgagc cgggtggcgt ggcacggaca aggcaagagc   5220
ctttccatcc cgcataaagt gatgcaccat tttgaccttg ttgatcgttt ttgtgtgttt   5280
agagcggccc cgtgcgggta ggcgaagtgc gcttctgagc aaggaagaga gaggtgcagc   5340
ttcttcttga tcagtgtggt aatcttcaac ggccacgctc gcttattcga tacctgtaaa   5400
gctaccggtg cacccgtgca agttgggcac cacgtagttg tactggtgaa tccaaatgtt   5460
agccgctagc ttggtgccct tttcgacagg aagggcttgg tgaaaagccg agggcccgac   5520
tgttcgggag ggccgcactt attagagttg aagccaagta agatggtgag tcatgataat   5580
tgagcagatc gcttgtttgg agcgatgaat cgtttgagtt tctgccccat cagttgtcga   5640
cggtagtgta ttggactacg gtgactataa cgggtgacgg ggagttaggg ctcgactccg   5700
gagagggagc ctgagagacg gctaccacat ccaaggaagg cagcaggcgc gtaaattacc   5760
caatgtggac tccacgaggt agtgacgaga aatatcaatg cggggcgctt cgcgtcttgc   5820
tattggaatg agagcaatgt aaaaccctca tcgaggatca actggagggc aagtctggtg   5880
ccagcagccg cggtaattcc agctccagaa gcgtatgcta aagttgttgc agttaaaaag   5940
ctcgtagttg aatttctggg gcgggagccc cggtctttgc gcgactgcgc tctgtttgcc   6000
gagcggctcc tctgccatcc tcgcctcttt ttttagtggc gtcgttcact gtaattaaag   6060
cagagtgttc caagcaggtc gtatgacctg gatgtttatt atgggatgat cagataggc   6120
tcgggtgcta ttttgttggt ttgcacatct gagtaatgat gaataggaac agttggggt   6180
attcgtattt aggagctaga ggtgaaattc ttggatttcc gaaagacgaa ctacagcgaa   6240
ggcatttacc aagcatgttt tcattaatca agaacgaaag tctggggatc gaagatgatt   6300
agataccatc gtagtctaga ccgtaaacga tgccgacttg cgattgcggg gtgtttgtat   6360
tggaccctcg cagcagcaca tgagaaatca aagtctttgg gttccggggg gagtatggtc   6420
gcaaggctga aacttaaagg aattgacgga agggcaccac caggagtgga gcctgcggct   6480
taatttgact caacacggga aaacttacca ggtccagaca taggtaggat tgacagattg   6540
agagctcttt cttgattcta tgggtggtgg tgcatggccg ttcttagttg gtggagtgat   6600
ttgtctggtt aattccgtta acgaacgaga cctcggccta ctaaatagcg gtgggtatgg   6660
cgacatactt gcgtacgctt cttagaggga catgttcggt atacgagcag gaagttcgag   6720
gcaataacag gtctgtgatg cccttagatg ttctgggccg cacgcgcgct acactgatgg   6780
gttcaacggg tggtcatcgt tgttcgcagc gaggtgcttt gccggaaggc atggcaaatc   6840
ctttcaacgc ccatcgtgct ggggctagat ttttgcaatt attaatctcc aacgaggaat   6900
tcctagtaaa cgcaagtcat cagcttgcat tgaatacgtc cctgcccttt gtacacaccg   6960
cccgtcgcac ctaccgattg aacggtccga tgaaaccatg gatgacctt ttgagcgttt   7020
gttcgcgagg ggggtcagaa ctcgggtgaa tcttattgtt tagaggaagg tgaagtcgta   7080
```

```
acaaggtttc cgtagtgaat cacgaattct ggatccgata cgtaacgcgt ctgcagcatg    7140
cgtggtaccg agctttccct atagtgagtc gtattagagc ttggcgtaat catggtcat    7199

<210> SEQ ID NO 49
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 49
gggatcagcc tgcctgaagg cgcttagtcc tgctcctcgg ccacgaag                   48

<210> SEQ ID NO 50
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 50
cttcgtggcc gaggagcagg actaagcgcc ttcaggcagg ctgatccc                   48

<210> SEQ ID NO 51
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 51
ggccctcccg aacagtcggg ccctcggctt ttcaccaagc ccttcctg                   48

<210> SEQ ID NO 52
<211> LENGTH: 6526
<212> TYPE: DNA
<213> ORGANISM: Thraustochytrium sp. ONC-T18

<400> SEQUENCE: 52
agctgtttcc tgtgtgaaat tgttatccgc tcacaattcc acacaacata cgagccggaa      60
gcataaagtg taaagcctgg ggtgcctaat gagtgagcta actcacatta attgcgttgc     120
gctcactgcc cgctttccag tcgggaaacc tgtcgtgcca gctgcattaa tgaatcggcc     180
aacgcgcggg gagaggcggt ttgcgtattg ggcgctcttc cgcttcctcg ctcactgact     240
cgctgcgctc ggtcgttcgg ctgcggcgag cggtatcagc tcactcaaag gcggtaatac     300
ggttatccac agaatcaggg gataacgcag gaaagaacat gtgagcaaaa ggccagcaaa     360
aggccaggaa ccgtaaaaag gccgcgttgc tggcgttttt ccataggctc cgcccccctg     420
acgagcatca caaaaatcga cgctcaagtc agaggtggcg aaacccgaca ggactataaa     480
gataccaggc gtttccccct ggaagctccc tcgtgcgctc tcctgttccg accctgccgc     540
ttaccggata cctgtccgcc tttctccctt cgggaagcgt ggcgctttct catagctcac     600
gctgtaggta tctcagttcg gtgtaggtcg ttcgctccaa gctgggctgt gtgcacgaac     660
cccccgttca gcccgaccgc tgcgccttat ccggtaacta tcgtcttgag tccaacccgg     720
taagacacga cttatcgcca ctggcagcag ccactggtaa caggattagc agagcgaggt     780
atgtaggcgg tgctacagag ttcttgaagt ggtggcctaa ctacggctac actagaagga     840
cagtatttgg tatctgcgct ctgctgaagc cagttacctt cggaaaaaga gttggtagct     900
cttgatccgg caaacaaacc accgctggta gcggtggttt ttttgtttgc aagcagcaga     960
```

```
ttacgcgcag aaaaaaagga tctcaagaag atcctttgat cttttctacg gggtctgacg    1020
ctcagtggaa cgaaaactca cgttaaggga ttttggtcat gaattaattc ttagaaaaac    1080
tcatcgagca tcaaatgaaa ctgcaattta ttcatatcag gattatcaat accatatttt    1140
tgaaaaagcc gtttctgtaa tgaaggagaa aactcaccga ggcagttcca taggatggca    1200
agatcctggt atcggtctgc gattccgact cgtccaacat caatacaacc tattaatttc    1260
ccctcgtcaa aaataaggtt atcaagtgag aaatcaccat gagtgacgac tgaatccggt    1320
gagaatggca aaagtttatg catttctttc cagacttgtt caacaggcca gccattacgc    1380
tcgtcatcaa aatcactcgc atcaaccaaa ccgttattca ttcgtgattg cgcctgagcg    1440
agacgaaata cgcgatcgct gttaaaagga caattacaaa caggaatcga atgcaaccgg    1500
cgcaggaaca ctgccagcgc atcaacaata ttttcacctg aatcaggata ttcttctaat    1560
acctggaatg ctgttttccc ggggatcgca gtggtgagta accatgcatc atcaggagta    1620
cggataaaat gcttgatggt cggaagaggc ataaattccg tcagccagtt tagtctgacc    1680
atctcatctg taacatcatt ggcaacgcta cctttgccat gtttcagaaa caactctggc    1740
gcatcgggct tcccatacaa tcgatagatt gtcgcacctg attgcccgac attatcgcga    1800
gcccatttat acccatataa atcagcatcc atgttggaat taatcgcgg cctagagcaa    1860 gacgtttccc gttgaatatg gctcataaca ccccttgtat tactgtttat gtaagcagac    1920
agttttattg ttcatgagat tatcaaaaag gatcttcacc tagatccttt taaattaaaa    1980
atgaagtttt aaatcaatct aaagtatata tgagtaaact tggtctgaca gttaccaatg    2040
cttaatcagt gaggcaccta tctcagcgat ctgtctattt cgttcatcca tagttgcctg    2100
actccccgtc gtgtagataa ctacgatacg ggagggctta ccatctggcc ccagtgctgc    2160
aatgataccg cgagacccac gctcaccggc tccagattta tcagcaataa accagccagc    2220
cggaagggcc gagcgcagaa gtggtcctgc aactttatcc gcctccatcc agtctattaa    2280
ttgttgccgg gaagctagag taagtagttc gccagttaat agtttgcgca acgttgttgc    2340
cattgctaca ggcatcgtgg tgtcacgctc gtcgtttggt atggcttcat tcagctccgg    2400
ttcccaacga tcaaggcgag ttacatgatc ccccatgttg tgcaaaaaag cggttagctc    2460
cttcggtcct ccgatcgttg tcagaagtaa gttggccgca gtgttatcac tcatggttat    2520
ggcagcactg cataattctc ttactgtcat gccatccgta agatgctttt ctgtgactgg    2580
tgagtactca accaagtcat tctgagaata gtgtatgcgg cgaccgagtt gctcttgccc    2640
ggcgtcaata cgggataata ccgcgccaca tagcagaact ttaaaagtgc tcatcattgg    2700
aaaacgttct cggggcgaaa actctcaag gatcttaccg ctgttgagat ccagttcgat    2760
gtaacccact cgtgcaccca actgatcttc agcatctttt actttcacca gcgtttctgg    2820
gtgagcaaaa acaggaaggc aaaatgccgc aaaaaaggga ataagggcga cacggaaatg    2880
ttgaatactc atactcttcc ttttcaata ttattgaagc atttatcagg gttattgtct    2940
catgagcgga tacatatttg aatgtattta gaaaaataaa caatagggg ttccgcgcac    3000 atttccccga aaagtgccac ctgacgcgcc ctgtagcggc gcattaagcg cggcgggtgt    3060
ggtggttacg cgcagcgtga ccgctacact tgccagcgcc ctagcgcccg ctcctttcgc    3120
tttcttccct tcctttctcg ccacgttcgc cggctttccc cgtcaagctc taaatcgggg    3180
gctcccttta gggttccgat ttagtgcttt acggcacctc gaccccaaaa aacttgatta    3240
gggtgatggt tcacgtagtg gccatcgccc tgatagacg gttttcgcc ctttgacgtt    3300
```

```
ggagtccacg ttctttaata gtggactctt gttccaaact ggaacaacac tcaaccctat    3360
ctcggtctat tcttttgatt tataagggat tttgccgatt tcggcctatt ggttaaaaaa    3420
tgagctgatt taacaaaaat ttaacgcgaa ttttaacaaa atattaacgc ttacaatttc    3480
cattcgccat tcaggctgcg caactgttgg gaagggcgat cggtgcgggc ctcttcgcta    3540
ttacgccagc tggcgaaagg gggatgtgct gcaaggcgat taagttgggt aacgccaggg    3600
ttttcccagt cacgacgttg taaaacgacg gccagtgaat tgtgcggccg cgagctcggg    3660
cccccacacg tgtggtctag agctagccta ggctcgagaa gcttcgcggc ttcccgtctc    3720
caagcttcgt ctcggtagag attctatctt cgcccggcag cccgccgccg tccggcaagt    3780
gtagaacggc agaaagccca cttgcacgga acgcccgaca agttgacgaa agcggcccgc    3840
aagtgcggca gcccggctgg ttttttcctcg cggcgaggcc aaaccgccaa cgccaccaag    3900
ccagacacca ggtatgtgcc gcacgcgccg ccgcacgcga gccccgagga tgccccgtac    3960
gcgctgacgc ctttctccgc cccgcccgcg agaagacgcg ctccggcaac ggcgggagcc    4020
gagcgaacgg gcgaggattg atcgagtagc tgcaggttga gaaaaaagga aaaccgccga    4080
gatggacaac ggctggatgg acgagaagac gcacgaggac gcgaggactg acgatgatca    4140
cgtgcgcagg aagacttgaa aagaagcaag gaaggtagaa aaaaagaag aaatcaagca    4200 agatggccaa gttgaccagt gccgttccgg tgctcaccgc gcgcgacgtc gccggagcgg    4260
tcgagttctg gaccgaccgg ctcgggttct cccgggactt cgtggaggac gacttcgccg    4320
gtgtggtccg ggacgacgtg accctgttca tcagcgcggt ccaggaccag gtggtgccgg    4380
acaacaccct ggcctgggtg tgggtgcgcg gcctggacga gctgtacgcc gagtggtcgg    4440
aggtcgtgtc cacgaacttc cgggacgcct ccgggccggc catgaccgag atcggcgagc    4500
agccgtgggg gcgggagttc gccctgcgcg accggccgg caactgcgtg cacttcgtgg    4560
ccgaggagca ggactaacac gtgctacgag atttcgattc caccgccgcc ttctatgaaa    4620
ggttgggctt cggaatcgtt ttccgggacg ccggctggat gatcctccag cgcgggatc    4680 tcatgctgga gttcttcgcc cacccccaact tgtttattgc agcttataat ggttacaaat    4740
aaagcaatag catcacaaat ttcacaaata aagcattttt ttcactgcat tctagttgtg    4800
gtttgtccaa actcatcaat gtatcttatc atgtctgagg gcccgactgt tcgggagggc    4860
cgcacttatt agagttgaag ccaagtaaga tggtgagtca tgataattga gcagatcgct    4920
tgtttggagc gatgaatcgt ttgagtttct gccccatcag ttgtcgacgg tagtgtattg    4980
gactacggtg actataacgg gtgacgggga gttaggggctc gactccggag agggagcctg    5040
agagacggct accacatcca aggaaggcag caggcgcgta aattacccaa tgtggactcc    5100
acgaggtagt gacgagaaat atcaatgcgg ggcgcttcgc gtcttgctat tggaatgaga    5160
gcaatgtaaa accctcatcg aggatcaact ggagggcaag tctggtgcca gcagccgcgg    5220
taattccagc tccagaagcg tatgctaaag ttgttcagt taaaaagctc gtagttgaat    5280
ttctggggcg ggagccccgg tctttgcgcg actgcgctct gtttgccgag cggctcctct    5340
gccatcctcg cctctttttt tagtggcgtc gttcactgta attaaagcag agtgttccaa    5400
gcaggtcgta tgacctggat gtttattatg ggatgatcag ataggctcg ggtgctattt    5460 tgttggtttg cacatctgag taatgatgaa taggaacagt tgggggtatt cgtatttagg    5520
agctagaggt gaaattcttg gatttccgaa agacgaacta cagcgaaggc atttaccaag    5580
catgttttca ttaatcaaga acgaaagtct ggggatcgaa gatgattaga taccatcgta    5640
gtctagaccg taaacgatgc cgacttgcga ttgcggggtg tttgtattgg accctcgcag    5700
```

```
cagcacatga gaaatcaaag tctttgggtt ccggggggag tatggtcgca aggctgaaac    5760
ttaaaggaat tgacggaagg gcaccaccag gagtggagcc tgcggcttaa tttgactcaa    5820
cacgggaaaa cttaccaggt ccagacatag gtaggattga cagattgaga gctctttctt    5880
gattctatgg gtggtggtgc atggccgttc ttagttggtg gagtgatttg tctggttaat    5940
tccgttaacg aacgagacct cggcctacta aatagcggtg gtatggcga catacttgcg     6000 tacgcttctt agagggacat gttcggtata cgagcaggaa gttcgaggca ataacaggtc    6060
tgtgatgccc ttagatgttc tgggccgcac gcgcgctaca ctgatgggtt caacgggtgg    6120
tcatcgttgt tcgcagcgag gtgctttgcc ggaaggcatg gcaaatcctt tcaacgccca    6180
tcgtgctggg gctagatttt tgcaattatt aatctccaac gaggaattcc tagtaaacgc    6240
aagtcatcag cttgcattga atacgtccct gcccttttgta cacaccgccc gtcgcaccta   6300
ccgattgaac ggtccgatga aaccatggga tgaccttttg agcgtttgtt cgcgaggggg    6360
gtcagaactc gggtgaatct tattgtttag aggaaggtga agtcgtaaca aggttttccgt   6420 agtgaatcac gaattctgga tccgatacgt aacgcgtctg cagcatgcgt ggtaccgagc    6480
tttccctata gtgagtcgta ttagagcttg gcgtaatcat ggtcat                    6526

<210> SEQ ID NO 53
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 53
ggtctagagc tagcctaggc tcgagaagct tcgcggcttc ccgtctc                  47

<210> SEQ ID NO 54
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 54
ggaacggcac tggtcaactt ggccatcttg cttgatttct tcttttttt ctaccttcc      59

<210> SEQ ID NO 55
<211> LENGTH: 7374
<212> TYPE: DNA
<213> ORGANISM: Thraustochytrium sp.

<400> SEQUENCE: 55
agctgtttcc tgtgtgaaat tgttatccgc tcacaattcc acacaacata cgagccggaa     60
gcataaagtg taaagcctgg ggtgcctaat gagtgagcta actcacatta attgcgttgc    120
gctcactgcc cgctttccag tcgggaaacc tgtcgtgcca gctgcattaa tgaatcggcc    180
aacgcgcggg gagaggcggt ttgcgtattg ggcgctcttc cgcttcctcg ctcactgact    240
cgctgcgctc ggtcgttcgg ctgcggcgag cggtatcagc tcactcaaag gcggtaatac    300
ggttatccac agaatcaggg gataacgcag gaaagaacat gtgagcaaaa ggccagcaaa    360
aggccaggaa ccgtaaaaag gccgcgttgc tggcgttttt ccataggctc cgcccccctg    420
acgagcatca caaaaatcga cgctcaagtc agaggtggcg aaacccgaca ggactataaa    480
gataccaggc gtttccccct ggaagctccc tcgtgcgctc tcctgttccg accctgccgc    540
```

```
ttaccggata cctgtccgcc tttctcccct cgggaagcgt ggcgctttct catagctcac    600
gctgtaggta tctcagttcg gtgtaggtcg ttcgctccaa gctgggctgt gtgcacgaac    660
cccccgttca gcccgaccgc tgcgccttat ccggtaacta tcgtcttgag tccaacccgg    720
taagacacga cttatcgcca ctggcagcag ccactggtaa caggattagc agagcgaggt    780
atgtaggcgg tgctacagag ttcttgaagt ggtggcctaa ctacggctac actagaagga    840
cagtatttgg tatctgcgct ctgctgaagc cagttacctt cggaaaaaga gttggtagct    900
cttgatccgg caaacaaacc accgctggta gcggtggttt ttttgtttgc aagcagcaga    960
ttacgcgcag aaaaaaagga tctcaagaag atcctttgat cttttctacg ggtctgacg    1020
ctcagtggaa cgaaaactca cgttaaggga ttttggtcat gaattaattc ttagaaaaac    1080
tcatcgagca tcaaatgaaa ctgcaattta ttcatatcag gattatcaat accatatttt    1140
tgaaaaagcc gtttctgtaa tgaaggagaa aactcaccga ggcagttcca taggatggca    1200
agatcctggt atcggtctgc gattccgact cgtccaacat caatacaacc tattaatttc    1260
ccctcgtcaa aaataaggtt atcaagtgag aaatcaccat gagtgacgac tgaatccggt    1320
gagaatggca aaagtttatg catttctttc cagacttgtt caacaggcca gccattacgc    1380
tcgtcatcaa aatcactcgc atcaaccaaa ccgttattca ttcgtgattg cgcctgagcg    1440
agacgaaata cgcgatcgct gttaaaagga caattacaaa caggaatcga atgcaaccgg    1500
cgcaggaaca ctgccagcgc atcaacaata ttttcacctg aatcaggata ttcttctaat    1560
acctggaatg ctgttttccc ggggatcgca gtggtgagta accatgcatc atcaggagta    1620
cggataaaat gcttgatggt cggaagaggc ataaattccg tcagccagtt tagtctgacc    1680
atctcatctg taacatcatt ggcaacgcta cctttgccat gtttcagaaa caactctggc    1740
gcatcgggct tcccatacaa tcgatagatt gtcgcacctg attgcccgac attatcgcga    1800
gcccatttat acccatataa atcagcatcc atgttggaat ttaatcgcgg cctagagcaa    1860
gacgtttccc gttgaatatg gctcataaca ccccttgtat tactgtttat gtaagcagac    1920
agttttattg ttcatgagat tatcaaaaag gatcttcacc tagatccttt taaattaaaa    1980
atgaagtttt aaatcaatct aaagtatata tgagtaaact tggtctgaca gttaccaatg    2040
cttaatcagt gaggcaccta tctcagcgat ctgtctattt cgttcatcca tagttgcctg    2100
actccccgtc gtgtagataa ctacgatacg ggagggctta ccatctggcc ccagtgctgc    2160
aatgataccg cgagacccac gctcaccggc tccagattta tcagcaataa accagccagc    2220
cggaagggcc gagcgcagaa gtggtcctgc aactttatcc gcctccatcc agtctattaa    2280
ttgttgccgg gaagctagag taagtagttc gccagttaat agtttgcgca acgttgttgc    2340
cattgctaca ggcatcgtgg tgtcacgctc gtcgtttggt atggcttcat tcagctccgg    2400
ttcccaacga tcaaggcgag ttacatgatc ccccatgttg tgcaaaaaag cggttagctc    2460
cttcggtcct ccgatcgttg tcagaagtaa gttggccgca gtgttatcac tcatggttat    2520
ggcagcactg cataattctc ttactgtcat gccatccgta agatgctttt ctgtgactgg    2580
tgagtactca accaagtcat tctgagaata gtgtatgcgg cgaccgagtt gctcttgccc    2640
ggcgtcaata cggataata ccgcgccaca tagcagaact ttaaaagtgc tcatcattgg    2700
aaaacgttct tcggggcgaa aactctcaag gatcttaccg ctgttgagat ccagttcgat    2760
gtaacccact cgtgcaccca actgatcttc agcatctttt actttcacca gcgtttctgg    2820
gtgagcaaaa acaggaaggc aaaatgccgc aaaaaaggga ataagggcga cacggaaatg    2880
ttgaatactc atactcttcc ttttcaata ttattgaagc atttatcagg gttattgtct    2940
```

```
catgagcgga tacatatttg aatgtattta gaaaaataaa caaataggggg ttccgcgcac   3000 atttccccga aaagtgccac ctgacgcgcc ctgtagcggc gcattaagcg cggcgggtgt   3060
ggtggttacg cgcagcgtga ccgctacact tgccagcgcc ctagcgcccg ctcctttcgc   3120
tttcttccct tcctttctcg ccacgttcgc cggctttccc cgtcaagctc taaatcgggg   3180
gctcccttta gggttccgat ttagtgcttt acggcacctc gaccccaaaa aacttgatta   3240
gggtgatggt tcacgtagtg gccatcgcc ctgatagacg ttttttcgcc ctttgacgtt   3300
ggagtccacg ttctttaata gtggactctt gttccaaact ggaacaacac tcaaccctat   3360
ctcggtctat tcttttgatt tataagggat tttgccgatt tcggcctatt ggttaaaaaa   3420
tgagctgatt taacaaaaat ttaacgcgaa ttttaacaaa atattaacgc ttacaatttc   3480
cattcgccat tcaggctgcg caactgttgg gaagggcgat cggtgcgggc ctcttcgcta   3540
ttacgccagc tggcgaaagg gggatgtgct gcaaggcgat taagttgggt aacgccaggg   3600
ttttcccagt cacgacgttg taaaacgacg gccagtgaat tgtgcggccg cgagctcggg   3660
cccccacacg tgtggtctag agctagccta ggctcgagaa gcttggcctg tctcccttgg   3720
ccatccattg cgctgcggaa gcattggatt gcgaactgcg tcggccagat cgcttggttt   3780
cccaacatga gacgcgctct gtcggcaaga ccatttccgc ccccggcttt gctcacaacc   3840
aactcgtagt agattttgta agaacactgt cacgtctgac tgctcccagc ccgcacgcat   3900
tgcgcttggc agcctcggtc ccaaaccgtc acggtcgctg cccggtccac gggaaaaaat   3960 aactttgtc cgcgagcggc cgttcaaggc gcagccgcga gcgtgccaac cgtccgtccc   4020
gcattctttt cccaatgttg gattcattca ttcttgccag gccagatcat ctgtgcctcc   4080
ctcgcgtgcc cttccttagc gtgcgcagat ctcttcttcc cagagcccgc gcggcgcttc   4140
gtggagtcgg cgtccatgtc atgcgcgcgc ggcgtcttga ccccctcggc ccctttggtt   4200
cgcggctgcg caacgagccg tttcacgcca ttgcgaccaa ccgcgcgcta aaatcggatt   4260
ggccgttgca cgccgatttt gcagcacctc tgggctgtga gggacgaccg tccactttta   4320
cccgcacaga gtggactttc accccctcac tccactgaag ccaacttttc gccgtcttcc   4380
caacccaaag tttatgctag ccctcatgcc gcaacggacg tcaccccat ttccactggc   4440 gacgtgggga cctgggcgca ataaggcgcg agaaggaaat tacgacggca cactggggcc   4500
agaagagggc actaggagcg gcaacccact ggcgcggcac agcggtttgg cgcggggatc   4560
aaagcaaaac ccggctcatc cagagcaaac ccgaatcagc cttcagacgg tcgtgcctaa   4620
caacacgccg ttctaccccg ccttccttgc gtccctcgcc tcccccgagc caagtcttc   4680 cgcccgctcc taacgccaac caagcaagat gagtaaagga gaagaacttt tcactggagt   4740
tgtcccaatt cttgttgaat tagatggtga tgttaatggg cacaaatttt ctgtcagtgg   4800
agagggtgaa ggtgatgcaa catacggaaa acttaccctt aaatttattt gcactactgg   4860
aaaactacct gttccatggc caacacttgt cactactttc acttatggtg ttcaatgctt   4920
ttcaagatac ccagatcata tgaagcggca cgacttcttc aagagcgcca tgcctgaggg   4980
atacgtgcag gagaggacca tctctttcaa ggacgacggg aactacaaga cacgtgctga   5040
agtcaagttt gagggagaca ccctcgtcaa caggatcgag cttaagggaa tcgatttcaa   5100
ggaggacgga aacatcctcg gccacaagtt ggaatacaac tacaactccc acaacgtata   5160
catcacggca gacaaacaaa agaatggaat caaagctaac ttcaaaatta gacacaacat   5220
tgaagatgga agcgttcaac tagcagacca ttatcaacaa aatactccaa ttggcgatgg   5280
```

```
ccctgtcctt ttaccagaca accattacct gtccacacaa tctgcccttt cgaaagatcc    5340
caacgaaaag agagaccaca tggtccttct tgagtttgta acagctgctg ggattacaca    5400
tggcatggat gaactataca ataacacgt gctacgagat ttcgattcca ccgccgcctt     5460
ctatgaaagg ttgggcttcg gaatcgtttt ccgggacgcc ggctggatga tcctccagcg    5520
cggggatctc atgctggagt tcttcgccca ccccaacttg tttattgcag cttataatgg    5580
ttacaaataa agcaatagca tcacaaattt cacaaataaa gcattttttt cactgcattc    5640
tagttgtggt ttgtccaaac tcatcaatgt atcttatcat gtctgagggc ccgactgttc    5700
gggagggccg cacttattag agttgaagcc aagtaagatg gtgagtcatg ataattgagc    5760
agatcgcttg tttggagcga tgaatcgttt gagtttctgc cccatcagtt gtcgacggta    5820
gtgtattgga ctacggtgac tataacgggt gacggggagt tagggctcga ctccggagag    5880
ggagcctgag agacggctac cacatccaag gaaggcagca ggcgcgtaaa ttacccaatg    5940
tggactccac gaggtagtga cgagaaatat caatgcgggg cgcttcgcgt cttgctattg    6000
gaatgagagc aatgtaaaac cctcatcgag gatcaactgg agggcaagtc tggtgccagc    6060
agccgcggta attccagctc cagaagcgta tgctaaagtt gttgcagtta aaaagctcgt    6120
agttgaattt ctggggcggg agccccggtc tttgcgcgac tgcgctctgt ttgccgagcg    6180
gctcctctgc catcctcgcc tcttttttta gtggcgtcgt tcactgtaat taaagcagag    6240
tgttccaagc aggtcgtatg acctggatgt ttattatggg atgatcagat agggctcggg    6300
tgctattttg ttggtttgca catctgagta atgatgaata ggaacagttg ggggtattcg    6360
tatttaggag ctagaggtga aattcttgga tttccgaaag acgaactaca gcgaaggcat    6420
ttaccaagca tgttttcatt aatcaagaac gaaagtctgg ggatcgaaga tgattagata    6480
ccatcgtagt ctagaccgta aacgatgccg acttgcgatt gcggggtgtt tgtattggac    6540
cctcgcagca gcacatgaga atcaaagtc tttgggttcc gggggagta tggtcgcaag     6600 gctgaaactt aaaggaattg acggaagggc accaccagga gtggagcctg cggcttaatt    6660
tgactcaaca cggaaaaact taccaggtcc agacataggt aggattgaca gattgagagc    6720
tctttcttga ttctatgggt ggtggtgcat ggccgttctt agttggtgga gtgatttgtc    6780
tggttaattc cgttaacgaa cgagacctcg gcctactaaa tagcggtggg tatggcgaca    6840
tacttgcgta cgcttcttag agggacatgt tcggtatacg agcaggaagt tcgaggcaat    6900
aacaggtctg tgatgccctt agatgttctg ggccgcacgc gcgctacact gatgggttca    6960
acgggtggtc atcgttgttc gcagcgaggt gctttgccgg aaggcatggc aaatcctttc    7020
aacgcccatc gtgctggggc tagatttttg caattattaa tctccaacga ggaattccta    7080
gtaaacgcaa gtcatcagct tgcattgaat acgtccctgc cctttgtaca caccgcccgt    7140
cgcacctacc gattgaacgg tccgatgaaa ccatgggatg accttttgag cgtttgttcg    7200
cgaggggggt cagaactcgg gtgaatctta ttgtttagag gaaggtgaag tcgtaacaag    7260
gtttccgtag tgaatcacga attctggatc cgatacgtaa cgcgtctgca gcatgcgtgg    7320
taccgagctt tccctatagt gagtcgtatt agagcttggc gtaatcatgg tcat          7374
```

<210> SEQ ID NO 56
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 56

```
ccagtgaaaa gttcttctcc tttactcatc ttgcttggtt ggcgttagga gcgg      54
```

<210> SEQ ID NO 57
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 57

```
ccgctcctaa cgccaaccaa gcaagatgag taaaggagaa gaacttttca ctgg      54
```

<210> SEQ ID NO 58
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 58

```
ggtggaatcg aaatctcgta gcacgtgtta tttgtatagt tcatccatgc catg      54
```

<210> SEQ ID NO 59
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 59

```
catggcatgg atgaactata caaataacac gtgctacgag atttcgattc cacc      54
```

<210> SEQ ID NO 60
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 60

```
cgtcctcctt gaaatcgatt ccc                                        23
```

<210> SEQ ID NO 61
<211> LENGTH: 6011
<212> TYPE: DNA
<213> ORGANISM: Thraustochytrium sp.

<400> SEQUENCE: 61

```
gacgaaaggg cctcgtgata cgcctatttt tataggttaa tgtcatgata ataatggttt      60
cttagacgtc aggtggcact tttcggggaa atgtgcgcgg aacccctatt tgtttatttt     120
tctaaataca ttcaaatatg tatccgctca tgagacaata accctgataa atgcttcaat     180
aatattgaaa aaggaagagt atgagtattc aacatttccg tgtcgccctt attccctttt     240
ttgcggcatt tgccttcct gttttgctc acccagaaac gctggtgaaa gtaaaagatg      300
ctgaagatca gttgggtgca cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca     600
```

```
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag cggataaag     840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc ttttttttctg cgcgtaatct   1260
gctgcttgca acaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg tcgggctga acgggggtt     1560
cgtgcacaca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggccttt    1860
gctggccttt tgctcacatg tgtgctgggc ccagccggcc agatctgagc tcgcggccgc   1920
gatatcgcta gctcgaggtg accaaaaagcc gtgaacgggc gtggccgagg ctacagcacg   1980
cagcggtgtt ctctgcgtat tatatttttc gcaaggtttc ccgacggctg gtccgcgtgc   2040
ccgcgccgcg cgcacgctct cactagacgt tggtcatgag tgtttcgagt caagacctcg   2100
gagaagaatt ggggcgcaca ccttccgtgc gcgcaccct gccactgtat accgtgcgta   2160
ccccaccaga cagaaggtca ccacccgtgc tctcttcgtc agctataccg tgtgctgtag   2220
atcgtcgcag gattcgggtt gtgcacaccg cgctccgtgg gctggggcc ctggcgcggc    2280
ggcttcctag gatatagtct ataaaaccca gcgaatttta cacacagagc ggttcatttg   2340
cgctgggtcc ggtgcgcaat tcggggcac agcctgcacg tttacatcga cgtaacagcc    2400
acagtcatcg tcgccagcct cttcggcctt cccaccgacc cggctgctgc ccgccttcct   2460
ggctggctga tgaactatcg cggcctgcct ggcacgtacg tgcccctccc atttctcccc   2520
ggtcctccag aaatgcgcct ccggcccaa tgaaagcagg cgttggccat gcggcgcccg    2580
acatctgggt cctcgcgcct tctttgatga catcgtcctc atcgtcgtcg gcgacctggt   2640
cttcgtgatc gcttgttgat cacgcgcttg gcatcttgcg aggagaaccg tctgcactct   2700
tttgcgcgg ccgaggtgcc ttccggggtg caggccagtc gccagaccag acctgctgca    2760
aagcccgaac atcgccgtcg aggtagacca ttaggtacgt acgtacgcac gtcttcatga   2820
tcgacgccaa cgtcatgcgg tcgatgcccc gccacgcgat ggcgctagca gccaggagcg   2880
cgtgtgtacg ggcgcggagc ttcgctcgca agcaaagctg ggcgcttggg ccggggatcg   2940
ggccactact tggacgaacg aacgaaacgc atgacgtcat ccttggcagt aaatcttgcc   3000
```

```
ggagcgcgca aaacccaggc tggacgcgct gggtgcgatt gagaaccgca agctttggag    3060
cctttcactg agcaggggga actgacgctg gagcgcgcga ccgtaggcga aggaatttga    3120
tcgaagtagg caggactgcc cgcagggtc aggccatggc caagttgacc agtgccgttc     3180
cggtgctcac cgcgcgcgac gtcgccgag cggtcgagtt ctggaccgac cggctcgggt     3240
tctcccggga cttcgtggag gacgacttcg ccggtgtggt ccgggacgac gtgaccctgt    3300
tcatcagcgc ggtccaggac caggtggtgc cggacaacac cctggcctgg gtgtgggtgc    3360
gcggcctgga cgagctgtac gccgagtggt cggaggtcgt gtccacgaac ttccgggacg    3420
cctccgggcc ggccatgacc gagatcggcg agcagccgtg ggggcgggag ttcgccctgc    3480
gcgacccggc cggcaactgc gtgcacttcg tggccgagga gcaggactga cacgtgctac    3540
gagatttcga ttccaccgcc gccttctatg aaaggttggg cttcggaatc gttttccggg    3600
acgccggctg gatgatcctc cagcgcgggg atctcatgct ggagttcttc gcccacccca    3660
acttgtttat tgcagcttat aatggttaca aataaagcaa tagcatcaca aatttcacaa    3720
ataaagcatt tttttcactg cattctagtt gtggtttgtc caaactcatc aatgtatctt    3780
atcatgtctg aattcccggg gatcctctag agtcgagaag cttgtcgacg aattcagatg    3840
tagtcatacg ctcgtctcaa agattaagcc atgcatgtgt aagtataagc gattatactg    3900
tgagactgcg aacggctcat tatatcagtt atgatttctt cggtattttc tttatatgga    3960
tacctgcagt aattctggaa ttaatacatg ctgagagggc ccgactgttc gggagggccg    4020
cacttattag agttgaagcc aagtaagatg gtgagtcatg ataattgagc agatcgcttg    4080
tttggagcga tgaatcgttt gagtttctgc cccatcagtt gtcgacggta gtgtattgga    4140
ctacggtgac tataacgggt gacggggagt tagggctcga ctccggagag ggagcctgag    4200
agacggctac cacatccaag gaaggcagca ggcgcgtaaa ttacccaatg tggactccac    4260
gaggtagtga cgagaaatat caatgcgggg cgcttcgcgt cttgctattg gaatgagagc    4320
aatgtaaaac cctcatcgag gatcaactgg agggcaagtc tggtgccagc agccgcggta    4380
attccagctc cagaagcgta tgctaaagtt gttgcagtta aaaagctcgt agttgaattt    4440
ctggggcggg agcccggtc tttgcgcgac tgcgctctgt ttgccgagcg gctcctctgc     4500
catcctcgcc tcttttttta gtggcgtcgt tcactgtaat taaagcagag tgttccaagc    4560
aggtcgtatg acctggatgt ttattatggg atgatcagat agggctcggg tgctattttg    4620
ttggtttgca catctgagta atgatgaata ggaacagttg ggggtattcg tatttaggag    4680
ctagaggtga aattcttgga tttccgaaag acgaactaca gcgaaggcat ttaccaagca    4740
tgttttcatt aatcaagaac gaaagtctgg ggatcgaaga tgattagata ccatcgtagt    4800
ctagaccgta aacgatgccg acttgcgatt gcgggtgtt tgtattggac cctcgcagca    4860
gcacatgaga aatcaaagtc tttgggttcc gggggagta tggtcgcaag gctgaaactt    4920
aaaggaattg acgaagggc accaccagga gtggagcctg cggcttaatt tgactcaaca    4980
cgggaaaact taccaggtcc agacataggt aggattgaca gattgagagc tctttcttga    5040
ttctatgggt ggtggtgcat ggccgttctt agttggtgga gtgatttgtc tggttaattc    5100
cgttaacgaa cgagacctcg gcctactaaa tagcggtggg tatggcgaca tacttgcgta    5160
cgcttcttag agggacatgt tcggtatacg agcaggaagt tcgaggcaat aacaggtctg    5220
tgatgccctt agatgttctg ggccgcacgc gcgctacact gatgggttca acggtggtc     5280 atcgttgttc gcagcgaggt gctttgccgg aaggcatggc aaatcctttc aacgcccatc    5340
```

-continued

```
gtgctggggc tagattttg caattattaa tctccaacga ggaattccta gtaaacgcaa    5400
gtcatcagct tgcattgaat acgtccctgc cctttgtaca caccgcccgt cgcacctacc    5460
gattgaacgg tccgatgaaa ccatgggatg accttttgag cgtttgttcg cgagggggt    5520
cagaactcgg gtgaatctta ttgtttagag gaaggtgaag tcatcacgaa ttctggatcc    5580
gatacgtaac gcgtctgcag catgcaagct tggcactggc cgtcgtttta caacgtcgtg    5640
actgggaaaa ccctggcgtt acccaactta atcgccttgc agcacatccc cctttcgcca    5700
gctggcgtaa tagcgaagag gcccgcaccg atcgcccttc ccaacagttg cgcagcctga    5760
atggcgaatg cgcctgatg cggtattttc tccttacgca tctgtgcggt atttcacacc    5820
gcatatatgg tgcactctca gtacaatctg ctctgatgcc gcatagttaa gccagccccg    5880
acacccgcca acaccgctg acgcgccctg acgggcttgt ctgctcccgg catccgctta    5940
cagacaagct gtgaccgtct ccgggagctg catgtgtcag aggttttcac cgtcatcacc    6000
gaaacgcgcg a                                                         6011
```

<210> SEQ ID NO 62
<211> LENGTH: 6661
<212> TYPE: DNA
<213> ORGANISM: Thraustochytrium sp.

<400> SEQUENCE: 62

```
gacgaaaggg cctcgtgata cgcctatttt tataggttaa tgtcatgata ataatggttt      60
cttagacgtc aggtggcact tttcggggaa atgtgcgcgg aaccctatt tgtttatttt     120
tctaaataca ttcaaatatg tatccgctca tgagacaata accctgataa atgcttcaat    180
aatattgaaa aggaagagt atgagtattc aacatttccg tgtcgccctt attcccttt     240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga   360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgctttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacggga gtcaggcaac tatggatgaa cgaaatagac   1020
agatcgctga gataggtgcc tcactgatta agcattggta actgtcagac caagtttact    1080
catatatact ttagattgat ttaaaacttc atttttaatt taaaaggatc taggtgaaga    1140
tcctttttga taatctcatg accaaaatcc cttaacgtga gttttcgttc cactgagcgt    1200
cagaccccgt agaaaagatc aaaggatctt cttgagatcc ttttttttctg cgcgtaatct    1260
gctgcttgca acaaaaaaa ccaccgctac cagcggtggt ttgtttgccg gatcaagagc    1320
taccaactct ttttccgaag gtaactggct tcagcagagc gcagatacca aatactgtcc    1380
ttctagtgta gccgtagtta ggccaccact tcaagaactc tgtagcaccg cctacatacc    1440
```

```
tcgctctgct aatcctgtta ccagtggctg ctgccagtgg cgataagtcg tgtcttaccg    1500
ggttggactc aagacgatag ttaccggata aggcgcagcg gtcgggctga acggggggtt    1560
cgtgcacaca gcccagcttg gagcgaacga cctacaccga actgagatac ctacagcgtg    1620
agcattgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cggtttcgc cacctctgac ttgagcgtcg attttgtga tgctcgtcag     1800 gggggcggag cctatggaaa aacgccagca acgcggcctt tttacggttc ctggccttt     1860 gctggccttt tgctcacatg tgtgctgggc ccagccggcc agatctgagc tcgcggccgc    1920
gatatcgcta gacaacgcca tcctcgacca cagcaaggac acgcaccgct tcggctacgg    1980
tatccagatc ggataaatat tataccgccc cttccgctct ccttttcttt tttgctcgtc    2040
tggatgccag actaaggagt ccttgctcct ctgcgcaagg ctgctcaccc agagtctctg    2100
cctgtggttg agcgcccacc aacaggttaa agcgaaccag ggccgccccg ttgccgctgc    2160
gatgtcgctg ctcttgcgag actcttcatt agatcggcgg aatgctgccg caggactgac    2220
cgcctcttcg ttcgttcgtt tgtacgcgag cggtgcgagc ggcttcgttg ttggcagata    2280
ggcagaacgc gagcagttca cgtttctttg cagctttatc tatccgcaaa ttcgcctcag    2340
cgtctgcaac tttccggtga ggacagcaga gctgcagttc tgatcgtctc catcttttgg    2400
agcgcatgtc gacgtccccc agctcgtctc cgtctcccct ggagtggacg gtctctttca    2460
cagtgcctgg gtgcggccat ttccctaaat aggttgcgca gccgagtttc cttaaacgtg    2520
cctggtccgc gtgcttccgc cttactacct gaacgcgcag tagctcggcg cgtgccgctt    2580
taaggcgggc ggggtggctg ctcttgctta cgccaggcgc gtacgtcagc agcgccggcg    2640
ccatgctgcc catagcggcc acagaatcgt aggcgctgca atcgggaact gccaagatgg    2700
caatcgagac gatcccccaa aagtggacaa gcaccgtcaa agtaacctgg ctgatgatgg    2760
ccgggaccgc ctggtgacgg ccagccggca aaaccggaat ctatcacgag gactgggcag    2820
atcaagggcc tagtgctagc gagcagctcg agcgaaagaa gcgcgccagc agcgcaggca    2880
cgccatggcc aagactagtg gcggtaccgg tacgcgtgga catatggcag catgcgcttc    2940
gcgagttttc gaaggggat cctaacacgt gctacgagat ttcgattcca ccgccgcctt    3000
ctatgaaagg ttgggcttcg gaatcgtttt ccgggacgcc ggctggatga tcctccagcg    3060
cggggatctc atgctggagt tcttcgccca ccccaacttg tttattgcag cttataatgg    3120
ttacaaataa agcaatagca tcacaaattt cacaaataaa gcatttttt cactgcattc     3180 tagttgtggt ttgtccaaac tcatcaatgt atcttatcat gtctgaattc ctcgttggag    3240
attaataatt gcaaaaatct agccccagca cgatgggcgt tgaaaggatt tgccatgcct    3300
tccggcaaag cacctcgctg cgaacaacga tgaccacccg ttgaacccat cagtgtagcg    3360
cgcgtgcggc ccagaacatc taagggcatc acagacctgt tattgcctcg aacttcctgc    3420
tcgtataccg aacatgtccc tctaagaagc gtacgcaagt atgtcgccat acccaccgct    3480
atttagtagg ccgaggtctc gttcgttaac ggaattaacc agacaaatca ctccaccaac    3540
taagaacggc catgcaccac cacccataga atcaagaaag agctctcaat ctgtcaatcc    3600
tacctatgtc tggacctggt aagttttccc gtgttgagtc aaattaagcc gcaggctcca    3660
ctcctggtgg tgcccttccg tcaattcctt taagtttcag ccttgcgacc atactccccc    3720
cggaacccaa agactttgat ttctcatgtg ctgctgcgag ggtccaatac aaacaccccg    3780
```

```
caatcgcaag tcggcatcgt ttacggtcta gactacgatg gtatctaatc atcttcgatc    3840
cccagacttt cgttcttgat taatgaaaac atgcttggta aatgccttcg ctgtagttcg    3900
tctttcggaa atccaagaat ttcacctcta gctcctaaat acgaataccc ccaactgttc    3960
ctattcatca ttactcagat gtgcaaacca acaaaatagc acccgagccc tatctgatca    4020
tcccataata aacatccagg tcatacgacc tgcttggaac actctgcttt aattacagtg    4080
aacgacgcca ctaaaaaaag aggcgaggat ggcagaggag ccgctcggca aacagagcgc    4140
agtcgcgcaa agaccggggc tcccgcccca gaaattcaac tacgagcttt ttaactgcaa    4200
caactttagc atacgcttct ggagctgaaa ttaccgcggc tgctggcacc agacttgccc    4260
tccagttgat cctcgatgag ggttttacat tgctctcatt ccaatagcaa gacgcgaagc    4320
gccccgcatt gatatttctc gtcactacct cgtggagtcc acattgggta atttacgcgc    4380
ctgctgcctt ccttggatgt ggtagccgtc tctcaggctc cctctccgga gtcgagccct    4440
aactccccgt cacccgttat agtcaccgta gtccaataca ctaccgtcga caactgatgg    4500
ggcagaaact caaacgattc atcgctccaa acaagcgatc tgctcaatta tcatgactca    4560
ccatcttact tggcttcaac tctaataagt gcggccctcc cgaacagtcg ggccctcaga    4620
catgataaga tacattgatg agtttggaca aaccacaact agaatgcagt gaaaaaaatg    4680
ctttatttgt gaaatttgtg atgctattgc tttatttgta accattataa gctgcaataa    4740
acaagttggg gtgggcgaag aactccagca tgagatcccc gcgctggagg atcatccagc    4800
cggcgtcccg gaaaacgatt ccgaagccca acctttcata aaggcggcg gtggaatcga    4860 aatctcgtag cacgtgttag tcctgctcct cggccacgaa gtgcacgcag ttgccggccg    4920
ggtcgcgcag ggcgaactcc cgcccccacg gctgctcgcc gatctcggtc atggccggcc    4980
cggaggcgtc ccggaagttc gtggacacga cctccgacca ctcggcgtac agctcgtcca    5040
ggccgcgcac ccacacccag gccagggtgt tgtccggcac cacctggtcc tggaccgcgc    5100
tgatgaacag ggtcacgtcg tcccggacca caccggcgaa gtcgtcctcc acgaagtccc    5160
gggagaaccc gagccggtcg gtccagaact cgaccgctcc ggcgacgtcg cgcgcggtga    5220
gcaccggaac ggcactggtc aacttggcca tcttgcttgg ttggcgttag gagcgggcgg    5280
aagacttggg ctcgggggag gcgagggacg caaggaaggc ggggtagaac ggcgtgttgt    5340
taggcacgac cgtctgaagg ctgattcggg tttgctctgg atgagccggg ttttgctttg    5400
atccccgcgc caaaccgctg tgccgcgcca gtgggttgcc gctcctagtg ccctcttctg    5460
gccccagtgt gccgtcgtaa tttccttctc gcgccttatt gcgcccaggt ccccacgtcg    5520
ccagtggaaa tgggggtgac gtccgttgcg gcatgagggc tagcataaac tttgggttgg    5580
gaagacggcg aaaagttggc ttcagtggag tgaggggtg aaagtccact ctgtgcgggt    5640
aaaagtggac ggtcgtccct cacagcccag aggtgctgca aaatcggcgt gcaacggcca    5700
atccgatttt agcgcgcggt tggtcgcaat ggcgtgaaac ggctcgttgc gcagccgcga    5760
accaaagggg ccgaggggt caagacgccg cgcgcgcatg acatgacgc cgactccacg    5820 aagcgccgcg cgggctctgg aagaagaga tctgcgcacg ctaaggaagg gcacgcgagg    5880
gaggcacaga tgatctggcc tggcaagaat gaatgaatcc aacattggga aaagaatgcg    5940
ggacggacgg ttggcacgct cgcggctgcg ccttgaacgg ccgctcgcgg acaaaagtta    6000 tttttttcccg tggaccgggc agcgaccgtg acggtttggg accgaggctg ccaagcgcaa    6060
tgcgtgcggg ctgggagcag tcagacgtgc agtgttcttt acaaaatcta ctacgagttg    6120
gttgtgagca agccggggg cggaaatggt cttgccgaca gagcgcgtct catgttggga    6180
```

```
aaccaagcga tctggccgac gcagttcgca atccaatgct tccgcagcgc aatggatggc    6240
caagggagac aggccaagct tggcactggc cgtcgtttta caacgtcgtg actgggaaaa    6300
ccctggcgtt acccaactta atcgccttgc agcacatccc cctttcgcca gctggcgtaa    6360
tagcgaagag gcccgcaccg atcgcccttc ccaacagttg cgcagcctga atggcgaatg    6420
gcgcctgatg cggtattttc tccttacgca tctgtgcggt atttcacacc gcatatatgg    6480
tgcactctca gtacaatctg ctctgatgcc gcatagttaa gccagccccg acacccgcca    6540
acacccgctg acgcgccctg acgggcttgt ctgctcccgg catccgctta cagacaagct    6600
gtgaccgtct ccgggagctg catgtgtcag aggttttcac cgtcatcacc gaaacgcgcg    6660
a                                                                    6661
```

<210> SEQ ID NO 63
<211> LENGTH: 85
<212> TYPE: DNA
<213> ORGANISM: Artificial sequence
<220> FEATURE:
<223> OTHER INFORMATION: Synthetic oligonucleotide

<400> SEQUENCE: 63

```
ttatacgcgt ggacatatgg cagcatgcgc ttcgcgagtt ttcgaagggg gatcctaaca    60
cgtgctacga gatttcgatt ccacc                                          85
```

<210> SEQ ID NO 64
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 64

```
atatccacgc gtaccggtac cgccactagt cttggccatg gcgtgcctgc gctgctggc     59
```

<210> SEQ ID NO 65
<211> LENGTH: 3670
<212> TYPE: DNA
<213> ORGANISM: Thraustochytrium sp.

<400> SEQUENCE: 65

```
gacgaaaggg cctcgtgata cgcctatttt tataggttaa tgtcatgata ataatggttt    60
cttagacgtc aggtggcact tttcggggaa atgtgcgcgg aacccctatt tgtttatttt    120
tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
```

```
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttaatt taaaaggatc taggtgaaga   1140 tccttttga taatctcatg accaaaatcc cttaacgtga gttttcgttc cactgagcgt   1200
cagaccccgt agaaaagatc aaaggatctt cttgagatcc ttttttctg cgcgtaatct   1260 gctgcttgca acaaaaaaa ccaccgctac cagcggtggt ttgtttgccg gatcaagagc   1320
taccaactct ttttccgaag gtaactggct tcagcagagc gcagatacca atactgtcc   1380 ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg tcgggctga acggggggtt   1560 cgtgcacaca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttgtga tgctcgtcag   1800 gggggcggag cctatggaaa aacgccagca acgcggcctt tttacggttc ctggcctttt   1860
gctggccttt tgctcacatg tgtgctgggc ccagccggcc agatctgagc tcgcggccgc   1920
gatatcgcta gacaacgcca tcctcgacca cagcaaggac acgcaccgct tcggctacgg   1980
tatccagatc ggataaatat tataccgccc cttccgctct cctttctt tttgctcgtc   2040 tggatgccag actaaggagt ccttgctcct ctgcgcaagg ctgctcaccc agagtctctg   2100
cctgtggtta agcgcccacc aacaggttaa agcgaaccag ggccgccccg ttgccgctgc   2160
gatgtcgctg ctcttgcgag actcttcatt agatcggcgg aatgctgccg caggactgac   2220
cgcctcttcg ttcgttcgtt tgtacgcgag cggtgcgagc ggcttcgttg ttggcagata   2280
ggcagaacgc gagcagttca cgtttctttg cagctttatc tatccgcaaa ttcgcctcag   2340
cgtctgcaac tttccggtga ggacagcaga gctgcagttc tgatcgtctc catcttttgg   2400
agcgcatgtc gacgtccccc agctcgtctc cgtctcccct ggagtggacg gtctctttca   2460
cagtgcctgg gtgcggccat ttccctaaat aggttgcgca gccgagtttc cttaaacgtg   2520
cctggtccgc gtgcttccgc cttactacct gaacgcgcag tagctcggcg cgtgccgctt   2580
taaggcgggc ggggtggctg ctcttgctta cgccaggcgc gtacgtcagc agcgccggcg   2640
ccatgctgcc catagcggcc acagaatcgt aggcgctgca atcgggaact gccaagatgg   2700
caatcgagac gatcccccaa aagtggacaa gcaccgtcaa agtaacctgg ctgatgatgg   2760
ccgggaccgc ctggtgacgg ccagccggca aaaccggaat ctatcacgag gactgggcag   2820
atcaagggcc tagtgctagc gagcagctcg agcgaaagaa gcgcgccagc agcgcaggca   2880
cgccatggcc aagactagtg gcggtaccgg tacgcgtgga catatggcag catgcgcttc   2940
gcgagttttc gaaggggat cctaacacgt gctacgagat ttcgattcca ccgccgcctt   3000
ctatgaaagg ttgggcttcg gaatcgtttt ccgggacgcc ggctggatga tcctccagcg   3060
cggggatctc atgctggagt tcttcgccca ccccaacttg tttattgcag cttataatgg   3120
ttacaaataa agcaatagca tcacaaattt cacaaataaa gcattttttt cactgcattc   3180
```

```
tagttgtggt ttgtccaaac tcatcaatgt atcttatcat gtctgaattc ccggggatcc    3240
tctagagtcg acctgcaggc atgcaagctt ggcactggcc gtcgttttac aacgtcgtga    3300
ctgggaaaac cctggcgtta cccaacttaa tcgccttgca gcacatcccc ctttcgccag    3360
ctggcgtaat agcgaagagg cccgcaccga tcgcccttcc caacagttgc gcagcctgaa    3420
tggcgaatgg cgcctgatgc ggtattttct ccttacgcat ctgtgcggta tttcacaccg    3480
catatatggt gcactctcag tacaatctgc tctgatgccg catagttaag ccagccccga    3540
cacccgccaa cacccgctga cgcgccctga cgggcttgtc tgctcccggc atccgcttac    3600
agacaagctg tgaccgtctc cgggagctgc atgtgtcaga ggttttcacc gtcatcaccg    3660
aaacgcgcga                                                          3670

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ggccaagttg accagtgccg                                                 20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
cagtcctgct cctcggccac                                                 20

<210> SEQ ID NO 68
<211> LENGTH: 1724
<212> TYPE: DNA
<213> ORGANISM: Artificial sequence
<220> FEATURE:
<223> OTHER INFORMATION: Synthetic construct

<400> SEQUENCE: 68
dgtagtcata cgctcgtctc aaagattaag ccatgcatgt gtaagtataa gcgattatac     60
tgtgagactg cgaacggctc attatatcag ttatgatttc ttcggtattt tctttatatg    120 gataccctgca gtaattctgg aattaataca tgctgagagg gcccgactgt tcgggagggc    180
cgcacttatt agagttgaag ccaagtaaga tggtgagtca tgataattga gcagatcgct    240
tgtttggagc gatgaatcgt ttgagtttct gccccatcag ttgtcgacgg tagtgtattg    300
gactacggtg actataacgg gtgacgggga gttagggctc gactccggag agggagcctg    360
agagacggct accacatcca aggaaggcag caggcgcgta aattacccaa tgtgactcc     420 acgaggtagt gacgagaaat atcaatgcgg ggcgcttcgc gtcttgctat tggaatgaga    480
gcaatgtaaa accctcatcg aggatcaact ggagggcaag tctggtgcca gcagccgcgg    540
taattccagc tccagaagcg tatgctaaag ttgttgcagt taaaaagctc gtagttgaat    600
ttctggggcg ggagccccgg tctttgcgcg actgcgctct gtttgccgag cggctcctct    660
gccatcctcg cctctttttt tagtggcgtc gttcactgta attaaagcag agtgttccaa    720
gcaggtcgta tgacctggat gtttattatg ggatgatcag ataggctcg ggtgctattt     780
```

-continued

```
tgttggtttg cacatctgag taatgatgaa taggaacagt tgggggtatt cgtatttagg      840
agctagaggt gaaattcttg gatttccgaa agacgaacta cagcgaaggc atttaccaag      900
catgttttca ttaatcaaga acgaaagtct ggggatcgaa gatgattaga taccatcgta      960
gtctagaccg taaacgatgc cgacttgcga ttgcggggtg tttgtattgg accctcgcag     1020
cagcacatga gaaatcaaag tctttgggtt ccgggggag tatggtcgca aggctgaaac     1080
ttaaaggaat tgacggaagg gcaccaccag gagtggagcc tgcggcttaa tttgactcaa     1140
cacgggaaaa cttaccaggt ccagacatag gtaggattga cagattgaga gctctttctt     1200
gattctatgg gtggtggtgc atggccgttc ttagttggtg gagtgatttg tctggttaat     1260
tccgttaacg aacgagacct cggcctacta aatagcggtg ggtatggcga catacttgcg     1320
tacgcttctt agagggacat gttcggtata cgagcaggaa gttcgaggca ataacaggtc     1380
tgtgatgccc ttagatgttc tgggccgcac gcgcgctaca ctgatgggtt caacgggtgg     1440
tcatcgttgt tcgcagcgag gtgctttgcc ggaaggcatg gcaaatcctt tcaacgccca     1500
tcgtgctggg gctagatttt tgcaattatt aatctccaac gaggaattcc tagtaaacgc     1560
aagtcatcag cttgcattga atacgtccct gcccttttgta cacaccgccc gtcgcaccta     1620
ccgattgaac ggtccgatga aaccatggga tgaccttttg agcgtttgtt cgcgaggggg     1680
gtcagaactc gggtgaatct tattgtttag aggaaggtga agtc                      1724
```

<210> SEQ ID NO 69
<211> LENGTH: 10
<212> TYPE: DNA
<213> ORGANISM: Artificial Sequence
<220> FEATURE:
<223> OTHER INFORMATION: Synthetic Construct

<400> SEQUENCE: 69

```
aaaacaaaaa                                                              10
```

ENGINEERING MICROORGANISMS

CROSS-REFERENCE TO RELATED APPLICATIONS

The present application claims benefit of, and priority to, U.S. provisional application Ser. No. 61/449,848, filed Mar. 7, 2011, the entire contents of which are herein incorporated by reference in their entirety.

SEQUENCE LISTING

In accordance with 37 CFR §1.52(e)(5), the present specification makes reference to a Sequence Listing (entitled "Sequence_Listing.txt," created on Mar. 7, 2012 and 108 kilobytes). The entire contents of the Sequence Listing are herein incorporated by reference.

BACKGROUND

Polyunsaturated fatty acids (PUFA) have long been recognized as having beneficial effects on health. The primary source for nutritional supplements is oil from fish species that have high concentrations of PUFA, such as anchovy, sardine, salmon, menhaden, herring, and tuna. However, lack of reliability of sources, and variability in the quality and/or quantity of PUFA isolated from fish mean there remains a need for alternative sources of PUFA.

Thraustochytrids are aquatic, eukaryotic microorganisms with the capacity to produce useful products, including PUFA and antioxidants (Carmona et al., Biosci. Biotechnol. Biochem. 67(4):884-888, 2003). These organisms are found worldwide in oceans and estuaries. Thraustochytrids are able to use a wide range of carbon and nitrogen sources for growth, indicating a potential for industrial cultivation with inexpensive nutrients.

There remains a need for improved sources of PUFA and other useful compounds.

SUMMARY

The present invention encompasses the appreciation of certain problems with available sources of PUFA and other useful compounds and agents. The present invention encompasses the recognition that genetically altered Thraustochytrids, whether by classical mutagenesis or otherwise, can provide useful sources of PUFA and other compounds and agents.

The present invention provides, in various embodiments, systems for genetically engineering Thraustochytrids, as well as genetically engineered Thraustochytrids that find various uses (e.g., PUFA production and/or biofuel production).

In certain embodiments, the invention provides isolated nucleic acid molecules comprising a Thraustochytrid or *Thraustochytrium* gene element, such as a Thraustochytrid or *Thraustochyrium* promoter or terminator. Exemplary promoters in provided isolated nucleic acid molecules include, but are not limited to, a tubulin promoter (e.g., nucleic acid sequences having at least 80%, 85%, 90%, 92%, 95%, 97%, 98%, 99%, or higher sequence identity to SEQ ID NO:6 or SEQ ID NO:10), a Δ5 elongase promoter (e.g., nucleic acid sequences having at least 80% sequence identity to SEQ ID NO:19), and a Δ4 desaturase promoter (e.g., nucleic acid sequences having at least 80%, 85%, 90%, 92%, 95%, 97%, 98%, 99%, or higher sequence identity to SEQ ID NO:24). Exemplary terminators in provided isolated nucleic acids molecules include, but are not limited to, a tubulin terminator (e.g., nucleic acid sequences having at least 80%, 85%, 90%, 92%, 95%, 97%, 98%, 99%, or higher sequence identity to SEQ ID NO:14 or SEQ ID NO:16).

In some embodiments, provided are isolated nucleic acid molecules comprising a heterologous sequence operably linked to a Thraustochytrid or *Thraustochytrium* gene promoter and a Thraustochytrid or *Thraustochytrium* gene terminator. In some embodiments, the heterologous sequence encodes a polypeptide. In some embodiments, provided isolated nucleic acid molecules further comprise a zeocin resistance gene.

In certain embodiments, provided are host cells comprising one or more provided isolated nucleic acids.

In certain embodiments, provided are methods of mutagenizing cells of a microorganism (e.g., Thraustochytrid or *Thraustochytrium*) comprising steps of: culturing cells of the microorganism on a medium, the medium comprising zeocin at a concentration at which zeocin kills 60-80% of the cells and isolating a subpopulation of cells that survive cultivation, thereby mutagenizing cells of a microorganism.

In certain embodiments, provided are Thraustochytrid or *Thraustochytrium* cells that contain one or more modifications to one or more genes encoding an enzyme polypeptide or part of an enzyme polypeptide complex involved in the PUFA biosynthetic pathway of Thraustochytrid or *Thraustochytrium*. In some embodiments, the one or modifications increase production of one or more PUFA by the modified cell as compared with a reference Thraustochytrid or *Thraustochytrium* cell when the modified and reference cells are cultured under comparable conditions. In some embodiments, the enzyme polypeptide or enzyme polypeptide complexes are selected from the group consisting of fatty acid synthase (FAS), Δ5 elongase, Δ12 elongase, Δ4 desaturase, and polyketide PUFA synthase (PKS). In some embodiments, the one or more PUFA are selected from the group consisting of alpha-linolenic acid ("ALA"), arachidonic acid ("ARA"), docosahexaenoic acid ("DHA"), docosapentaenoic acid ("DPA"), eicosopentaenoic acid ("EPA"), gamma-linolenic acid ("GLA"), and linoleic acid ("LA"). In some embodiments, the enzyme or enzyme complexes are selected from the group consisting of polyketide PUFA synthase (PKS), Δ9 desaturase, elongase, and omega-3 desaturase.

In certain embodiments, provided are methods for transforming a Thraustochytrid or *Thraustochytrium* cell comprising the steps of: (a) providing a competent Thraustochytrid or *Thraustochytrium* cell; (b) delivering a recombinant nucleic acid into the competent Thraustochytrid or *Thraustochytrium* cell, wherein the recombinant nucleic acid comprises a selectable marker; and (c) culturing the competent Thraustochytrid or *Thraustochytrium* cell in a culturing medium containing a selection agent that reduces growth of cells without the selectable marker. In some embodiments, the selectable marker is an antibiotic resistance gene. In some embodiments, the selection agent is an antibiotic. For example, the antibiotic may be zeocin. In some embodiments, zeocin is present at a concentration greater than 50 μg/mL (e.g., about 100 μg/mL).

In some embodiments of provided methods for transforming a Thraustochytrid or *Thraustochytrium* cell, the recombinant nucleic acid further comprises a gene expression cassette distinct from the selectable marker.

In some embodiments, provided methods for transforming a Thraustochytrid or *Thraustochytrium* cell further comprise a step of isolating a competent Thraustochytrid or *Thraustochytrium* cell containing the selectable marker.

In some embodiments, the step of delivering comprises biolistic delivery of particles coated with the recombinant nucleic acid. For example, particles comprising gold particles may be used in biolistic delivery.

In some embodiments, the culturing medium contains a level of salt between a lower salt concentration and an upper salt concentration. In some embodiments, the lower concentration is about 1, about 2, about 3, about 4, about 5, about 6, about 7, about 8, about 9, about 10, about 12, about 15, about 17, about 18, about 19, or about 20 g/L. In some embodiments, the upper salt concentration is about 20, about 22, about 25, about 27, about 30, about 32, about 35, about 37, about 40, about 45, about 50, about 55, about 60, about 65, or about 70 g/L. In some embodiments, the salt concentration is between about 3 g/L and about 70 g/L; between about 5 g/L and about 60 g/L; 10 g/L and about 40 g/L of salt (e.g., between about 15 g/L and about 35 g/L salt, or between about 18 g/L and about 35 g/L salt; or between about 9 g/L and about 18 g/L). In some embodiments, the salt is or comprises a salt selected from the group consisting of sodium salts (e.g., sea salt, sodium chloride, table salt, sodium sulfate, etc), potassium salts, and combinations thereof. In some embodiments, the salt is or comprises a non-chloride salt. In some embodiments, the salt is or comprises a non-chloride sodium salt.

In certain embodiments, provided are Thraustochytrid or *Thraustochytrium* cells competent for genetic transformation.

In certain embodiments, provided are Thraustochytrid or *Thraustochytrium* cells transformed with a recombinant nucleic acid.

In certain embodiments, provided are methods of culturing Thraustochytrid or *Thraustochytrium* cells, the method comprising: growing a culture comprising Thraustochytrid or *Thraustochytrium* cells under a first set of conditions under which biomass increases (and optionally other features increase or decrease as well); shifting the first set of culture conditions to a second set of conditions in which lipid productivity increases, wherein the shifting comprises one or more of: (a) decreasing oxygen concentrations from a first oxygen concentration to a second oxygen concentration; (b) increasing C:N ratio from a first C:N ratio to a second C:N ratio; (c) decreasing temperature from a first temperature to a second temperature; and combinations thereof.

In certain embodiments, provided are methods of providing a PUFA, the method comprising: providing a Thraustochytrid or *Thraustochytrium* cell that is modified as compared with a reference Thraustochytrid or *Thraustochytrium* cell in that the modified cell contains one or more genetic modifications that increase production of one or more PUFA by the modified cell as compared with the reference cell when the modified and reference cells are cultured under comparable conditions; and culturing the modified Thraustochytrid or *Thraustochytrium* cell under conditions and for a time sufficient to achieve production of the one or more PUFA.

In some embodiments, the step of providing comprises providing a Thraustochytrid or *Thraustochytrium* cell containing at least one engineered Thraustochytrid or *Thraustochytrium* promoter.

In some embodiments, the step of providing comprises providing a Thraustochytrid or *Thraustochytrium* cell containing at least one engineered Thraustochytrid or *Thraustochytrium* terminator.

In some embodiments, the step of providing comprises providing a Thraustochytrid or *Thraustochytrium* cell that is modified with respect to a reference Thraustochytrid or *Thraustochytrium* cell in that the modified Thraustochytrid or *Thraustochytrium* cell contains at least one expressed heterologous polypeptide. In some embodiments, the at least one heterologous protein is expressed from a gene that is operably linked with an engineered Thraustochytrid or *Thraustochytrium* promoter, an engineered Thraustochytrid or *Thraustochytrium* terminator, or both. In some embodiments, the at least one heterologous polypeptide comprises at least one heterologous PUFA biosynthesis polypeptide.

In some embodiments, the genetic modification comprises at least one nucleotide mutation that increases expression or activity of PUFA biosynthesis polypeptide. In some embodiments, the PUFA biosynthesis polypeptide whose expression or activity is increased is an endogenous PUFA production polypeptide. In some embodiments, the PUFA production polypeptide whose expression or activity is increased is a heterologous PUFA biosynthesis polypeptide.

In certain embodiments, provided are engineered Thraustochytrid or *Thraustochytrium* cells that express a heterologous PUFA production polypeptide.

In certain embodiments, provided are engineered Thraustochytrid or *Thraustochytrium* cells that produce at least one PUFA at a level at least 36% higher than a non-engineered Thraustochytrid or *Thraustochytrium* cell when the engineered and non-engineered cells are cultured under comparable conditions.

In certain embodiments, provided are compositions comprising: at least one PUFA; and one or more components of a Thraustochytrid or *Thraustochytrium* cell that contains an antibiotic resistance gene or is progeny of a Thraustochytrid or *Thraustochytrium* cell that contains an antibiotic resistance gene. In some embodiments, the antibiotic resistance gene is a zeocin resistance gene.

In certain embodiments, provided are compositions comprising: at least one PUFA; and one or more components of (a) a Thraustochytrid or *Thraustochytrium* cell that has been cultured in or on a medium comprising zeocin at a concentration at which zeocin kills 60-80% of the cells, or (b) a progeny of a Thraustochytrid or *Thraustochytrium* cell that has been cultured in or on a medium comprising zeocin at a concentration at which zeocin kills 60-80% of the cells.

Details of one or more embodiments of the invention are set forth in the accompanying drawings and the description below. Other features, objects, and advantages of the invention will be apparent from the description and drawings, and from the claims. All cited patents, patent applications, and references (including references to public sequence database entries) are incorporated by reference in their entireties for all purposes.

n-6 denotes the omega-6 PUFA biosynthetic pathway and n-3 denotes the omega-3 PUFA biosynthetic pathway.

Figure 2:
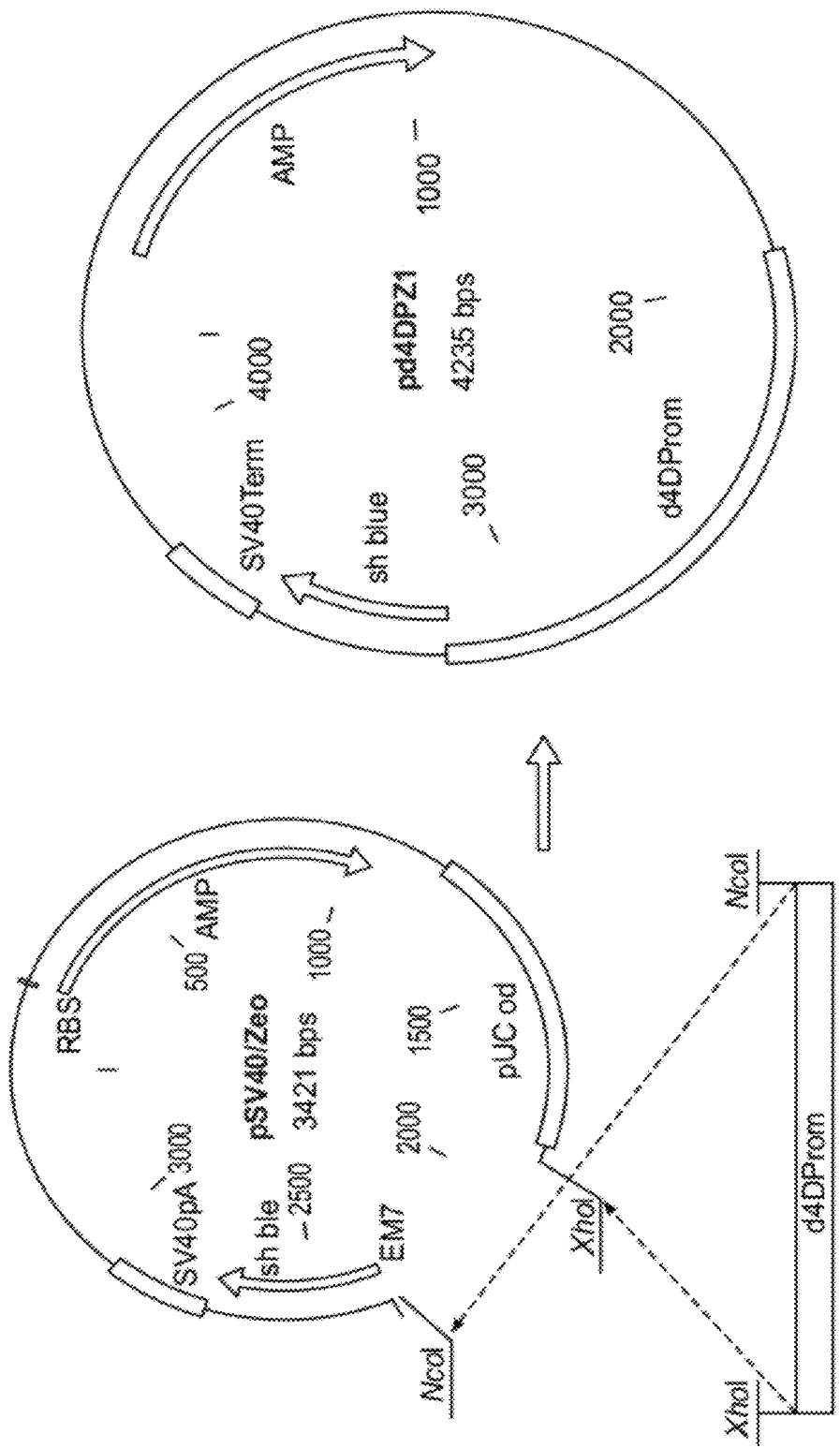

FIG. 2 is a schematic representation of the generation of the gene expression vector pd4DPZ1.

Figure 3:
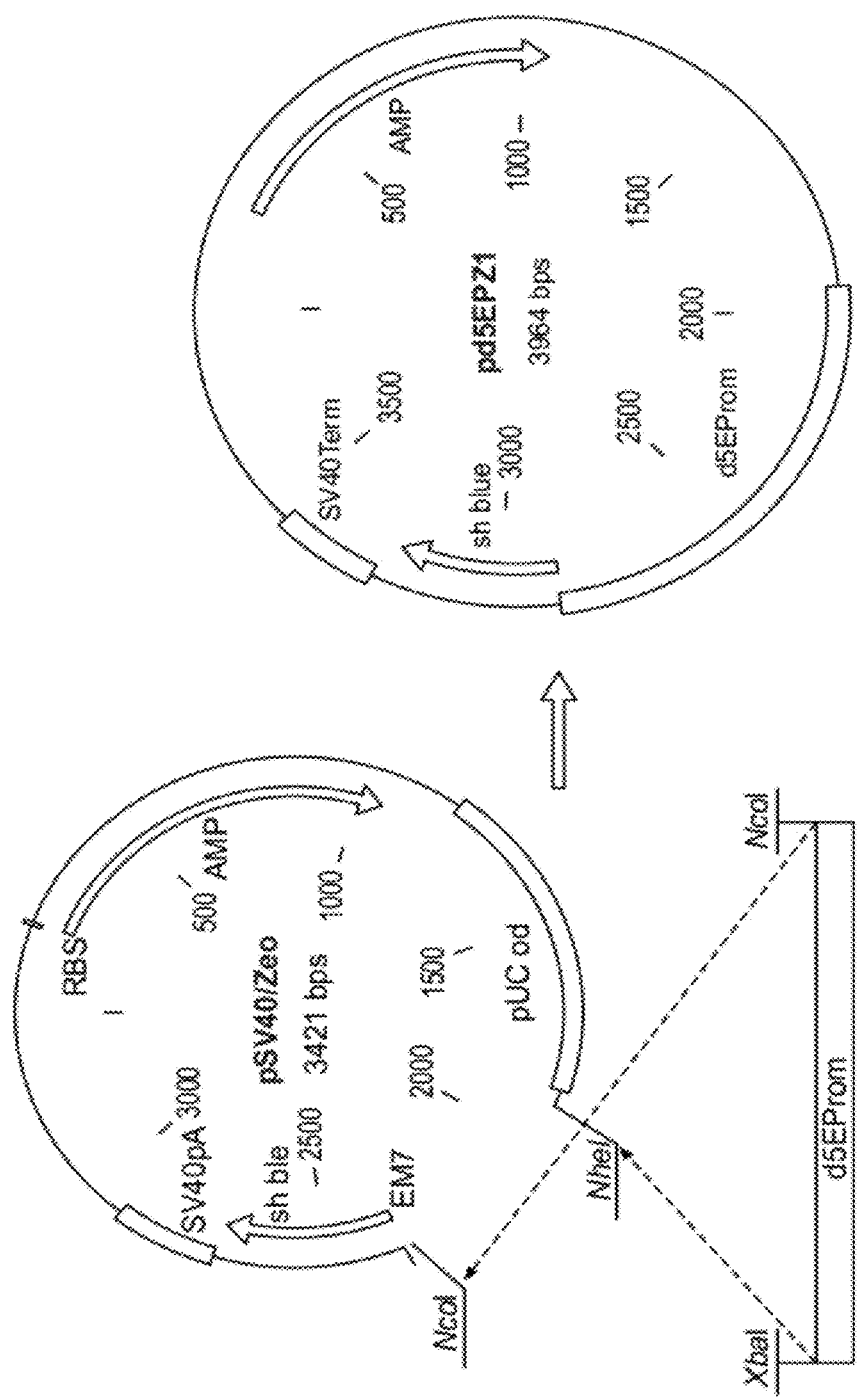

FIG. 3 is a schematic representation of the generation of the gene expression vector pd5EPZ1.

Figure 4:
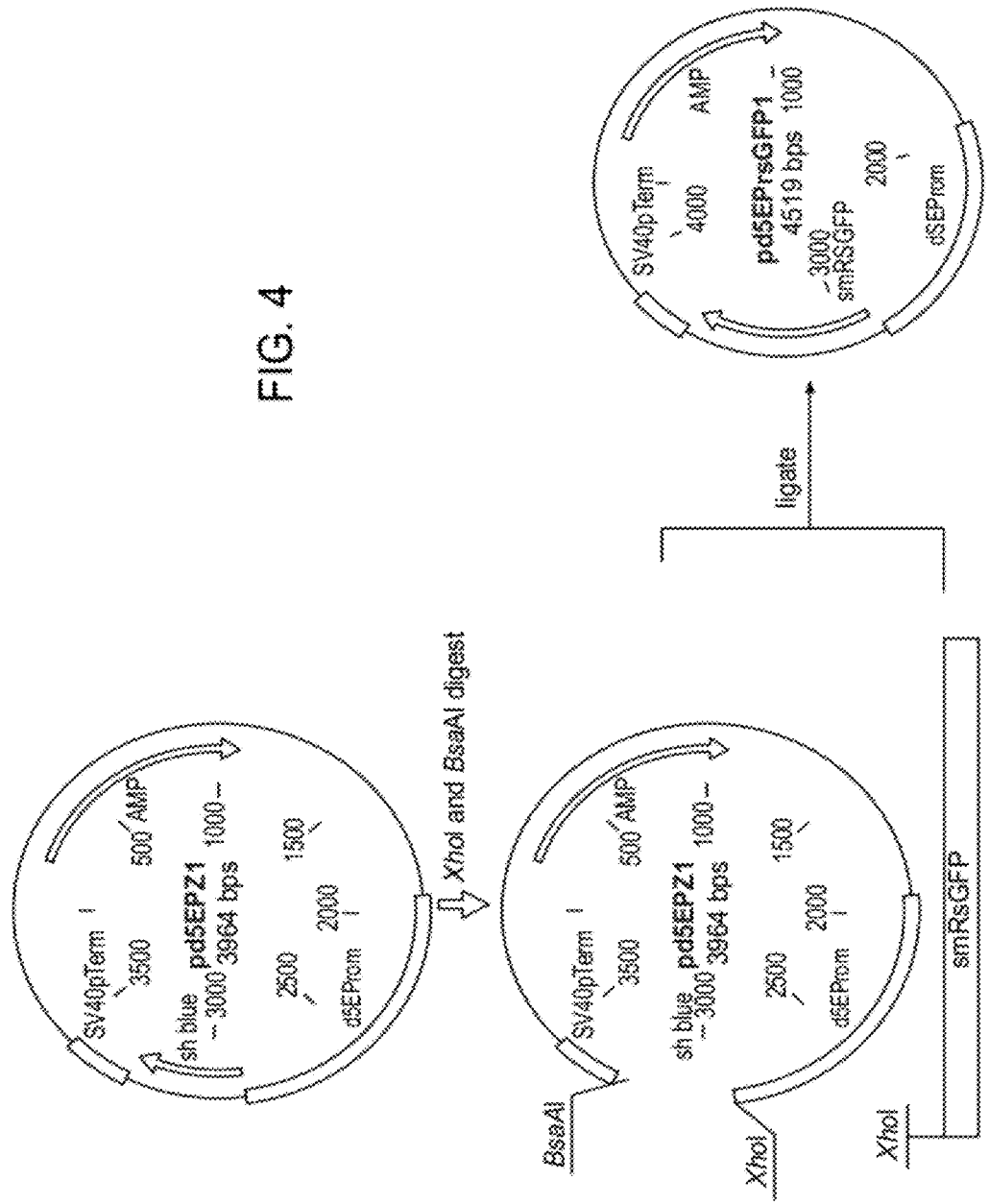

FIG. 4 is a schematic representation of the generation of the gene expression vector pd5EPrsGFP1 as well as the constructs of the intermediate plasmid produced by the processes.

Figure 5:
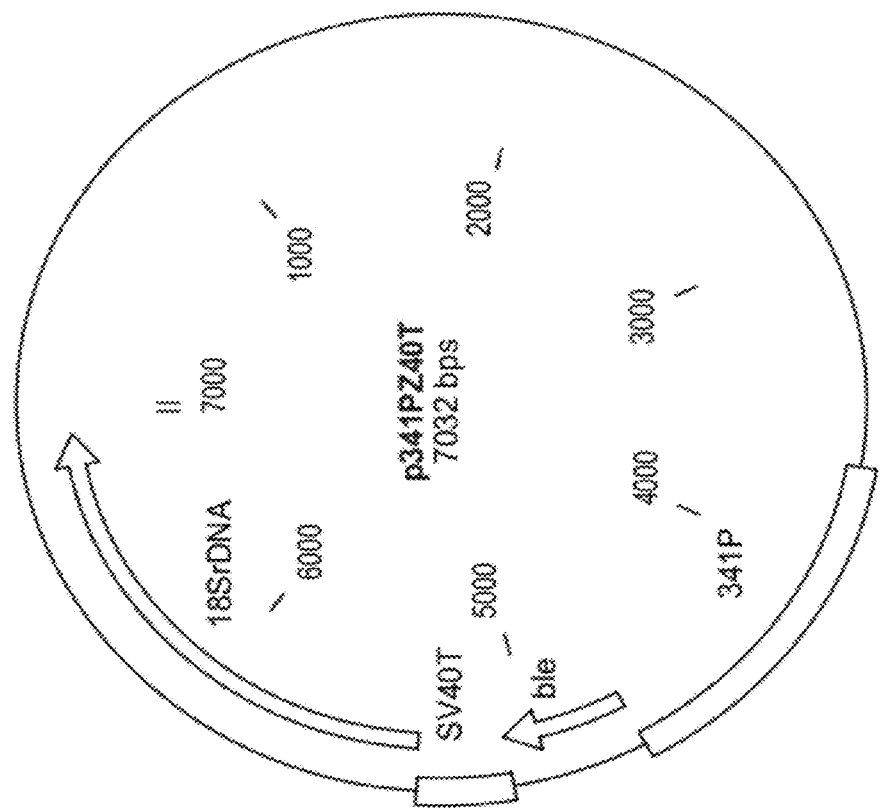

FIG. 5 is a schematic illustration of the generation of the gene expression vector p341PZ40T.

Figure 6:
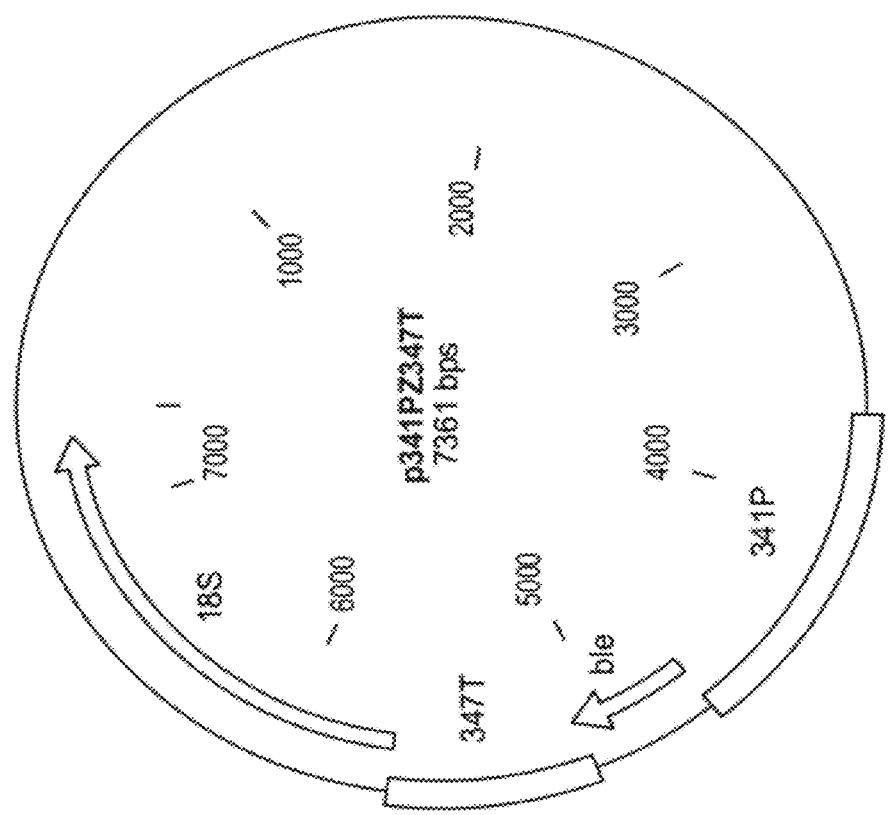

FIG. 6 is a schematic illustration of the generation of the gene expression vector p341PZ347T.

Figure 7:
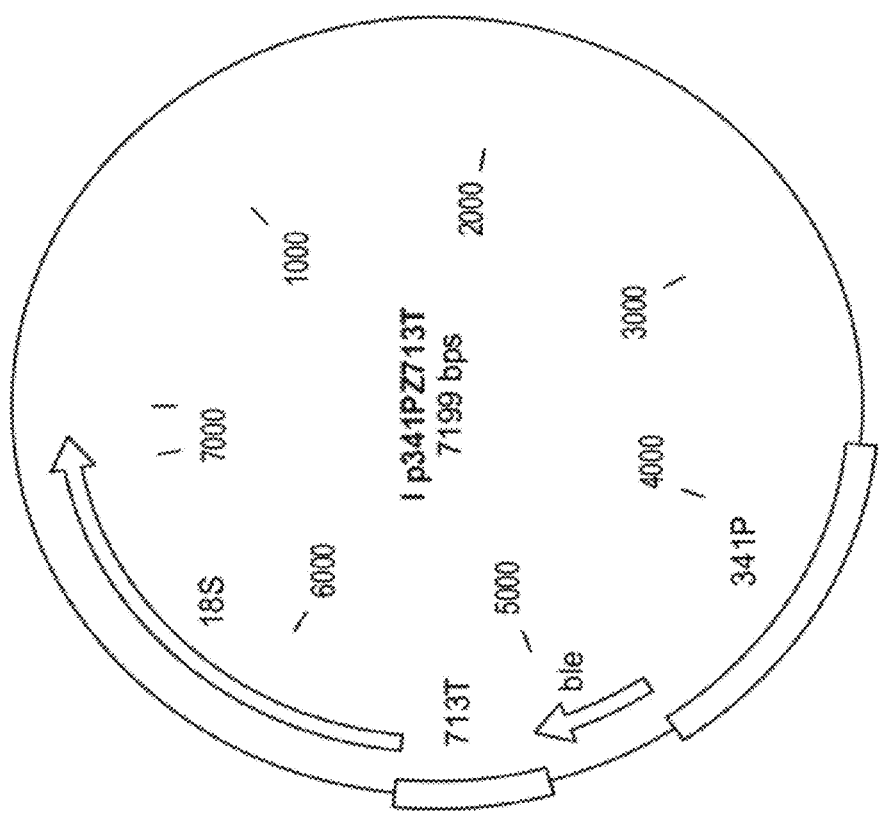

FIG. 7 is a schematic illustration of the generation of the gene expression vector p341PZ713T.

Figure 8:
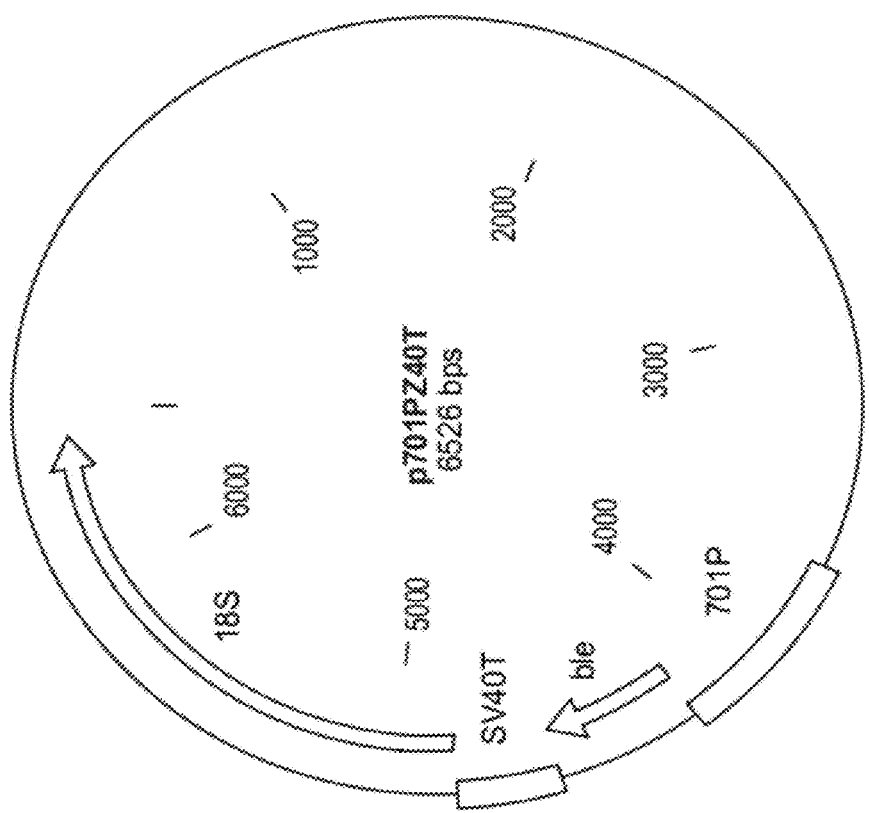

FIG. 8 is a schematic illustration of the generation of the gene expression vector p701PZ40T.

Figure 9:
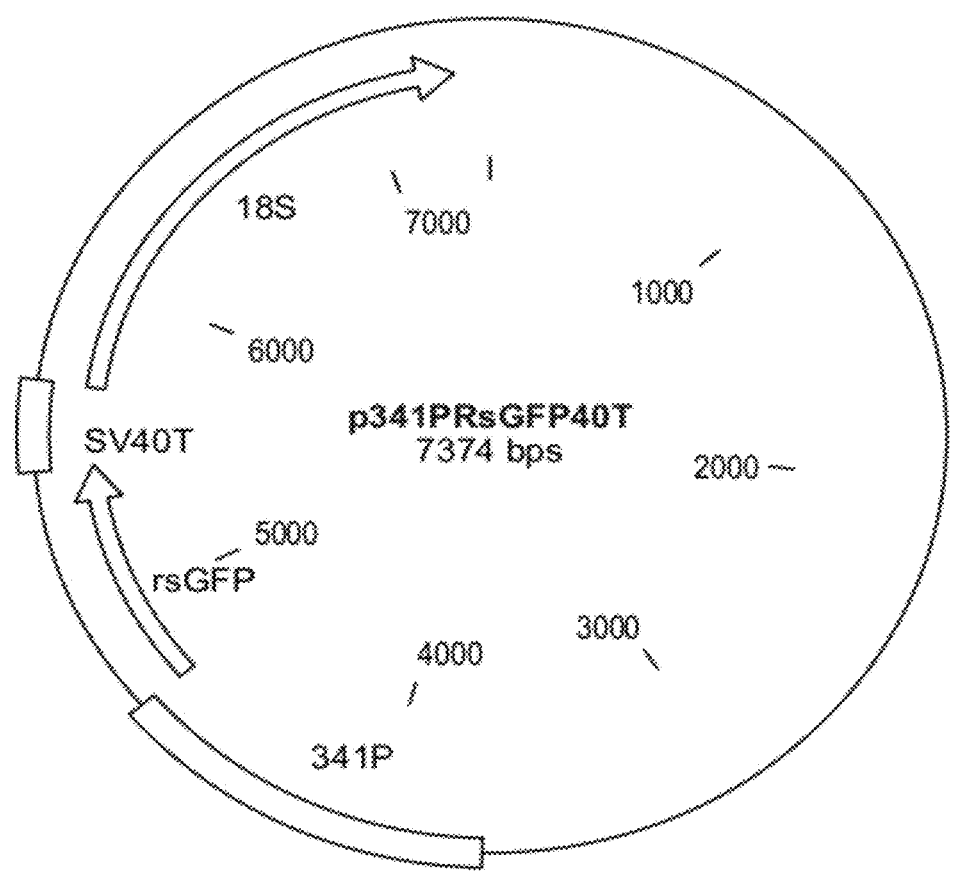

FIG. 9 is a schematic illustration of the generation of the gene expression vector p341PsmRsGFP40T.

Figure 10:
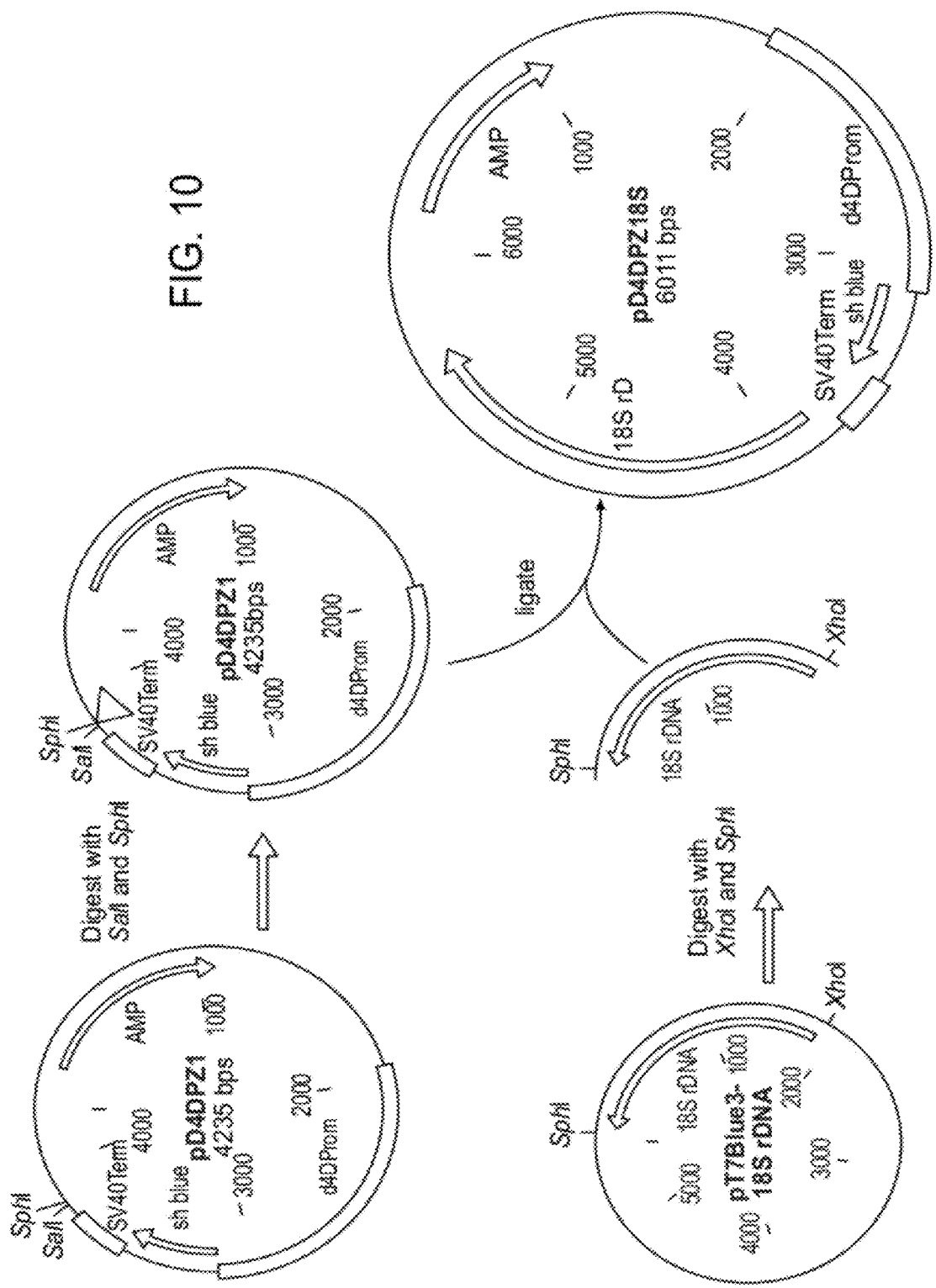

FIG. 10 is a schematic illustration of the generation of the gene expression vector pD4DPZ18S as well as the constructs of the intermediate plasmid produced by the processes.

Figure 11:
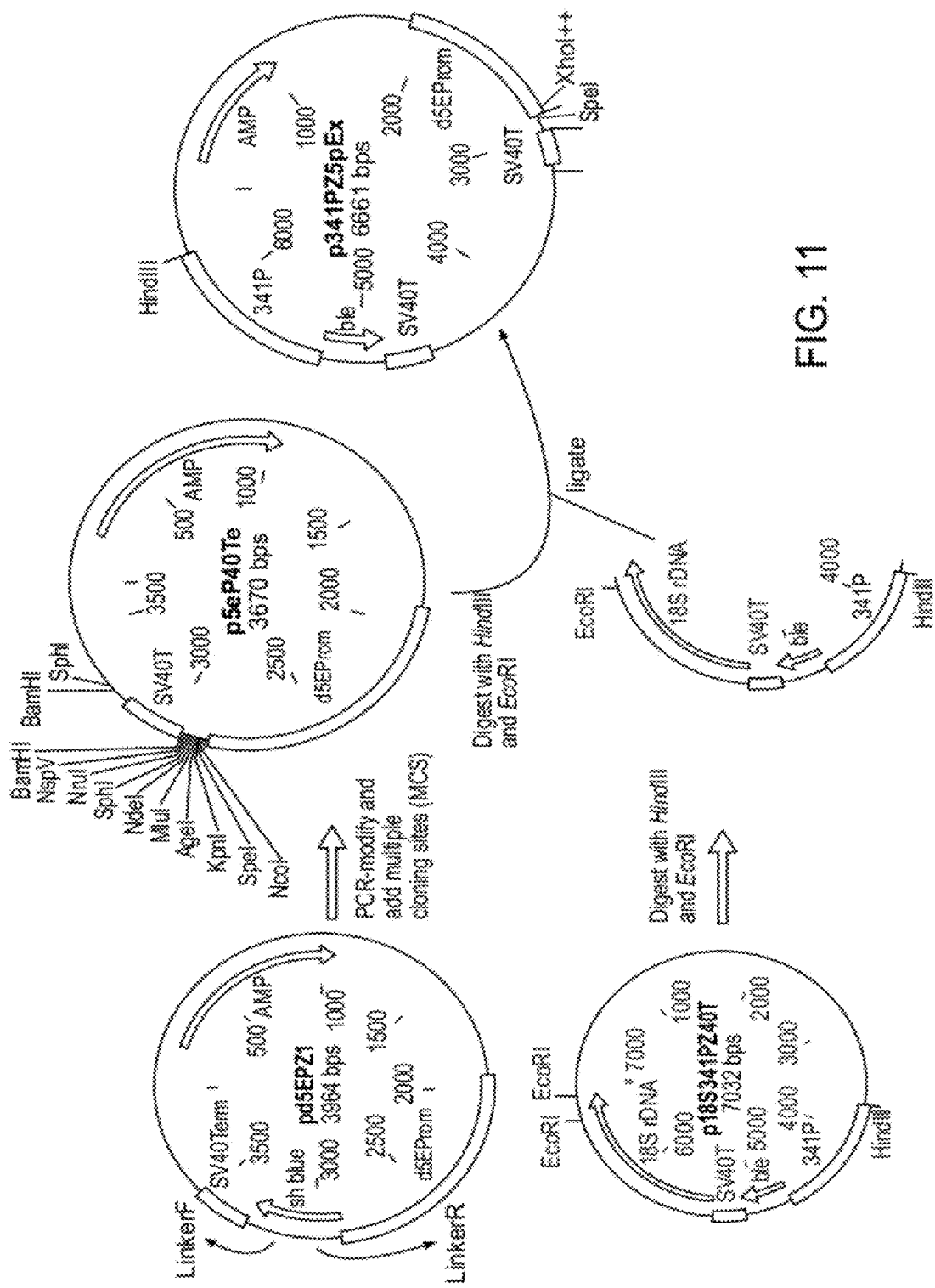

FIG. 11 is a schematic representation of the generation of the gene expression vector p341PZ5EpEx and the constructs of the intermediate plasmids produced by the processes.

Figure 12:
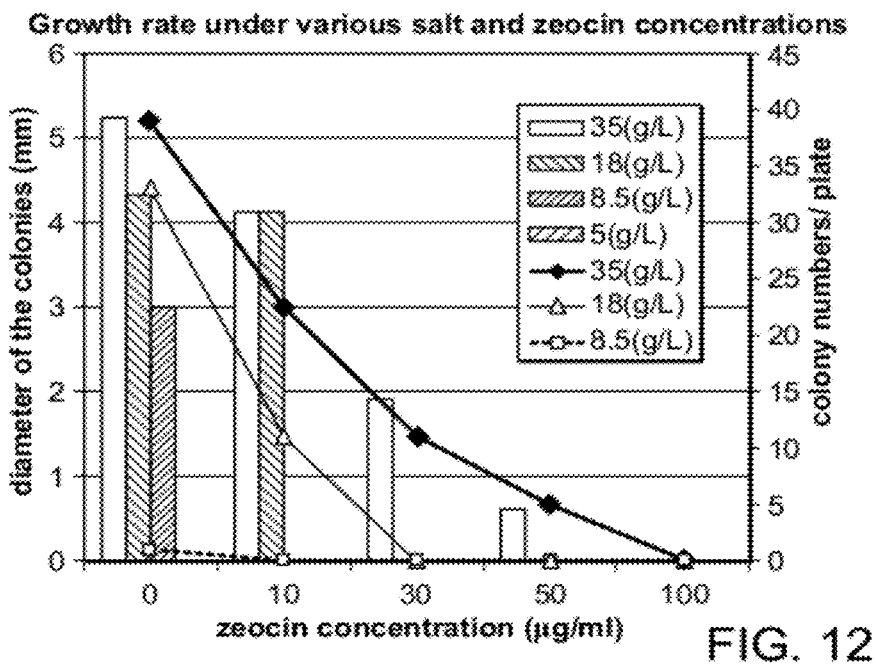

FIG. 12 illustrates effects of antibiotic zeocin on the growth and colony numbers of ONC-T18 at various salinities in the growth medium ONC-T18-GM0 plates. Results indicate that ONC-T18 grew faster and produced more colonies under higher salinity (e.g. 35 g/L artificial sea salt) in ONC-T18-GM0 medium than under lower salinity (e.g., 8.5 g/L artificial sea salt). At the median salinity (e.g., 18 g/L artificial sea salt), zeocin, at the concentration 30 μg/mL, could completely inhibit the growth of ONC-T18 in ONC-T18-GM0 agar plates.

Figure 13:
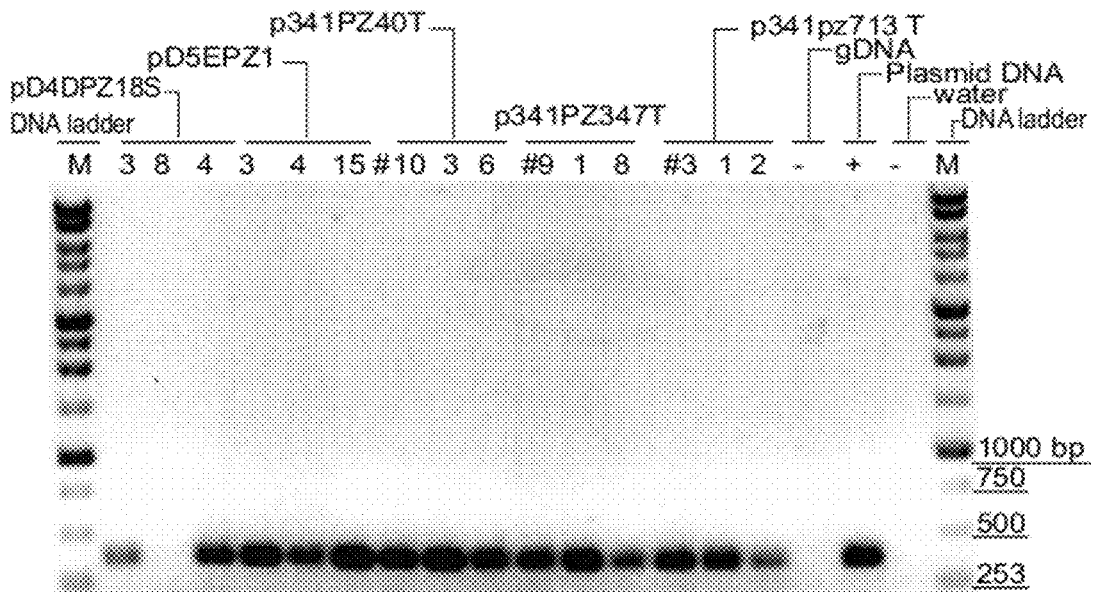

FIG. 13 illustrates zeocin resistance of ONC-T18 strains transformed with the plasmid DNAs in which the zeocin resistance gene is driven under various ONC-T18 gene promoter and terminators, in the agar plates of growth medium (ONC-T18-GM0). Results show that all of ONC-T18 transformant strains are resistant to antibiotic zeocin, but not the wild type ONC-T18 strains. Some transformant strains are highly resistant to zeocin (e.g., 5000 μg/mL).

Figure 14:
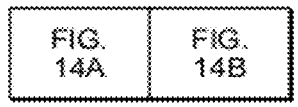
Figure 14A:
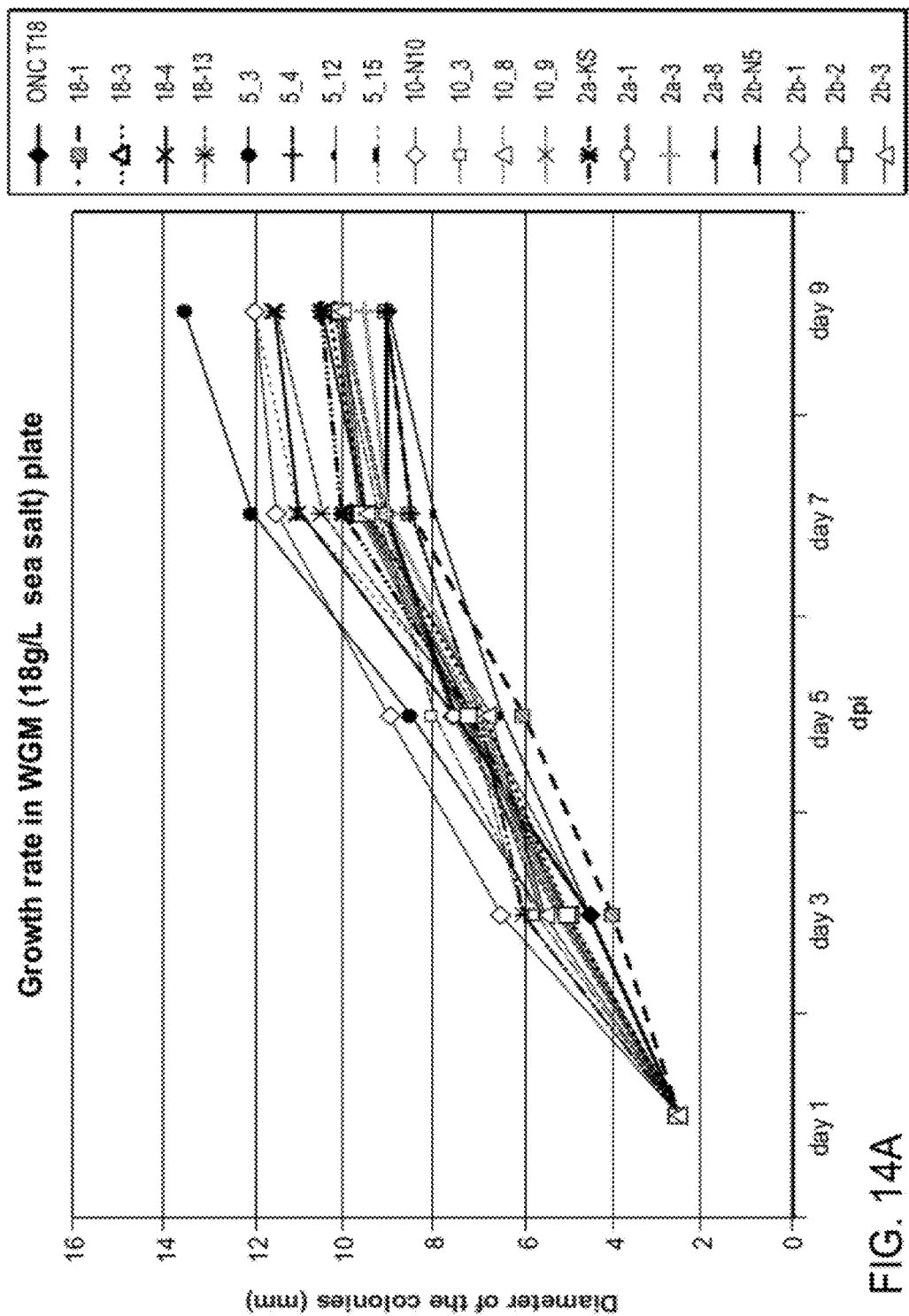
Figure 14B:
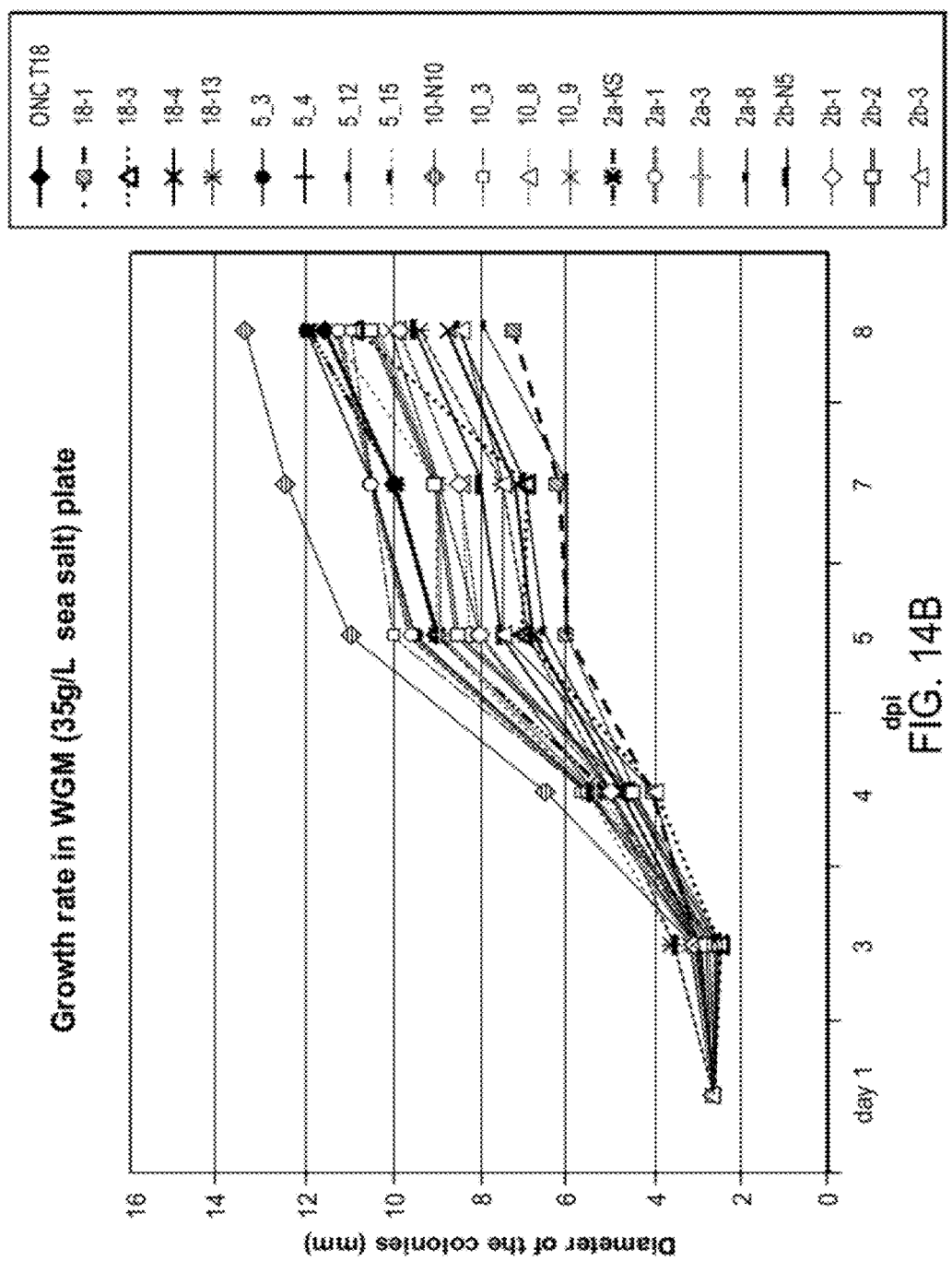

FIG. 14 illustrates the detection of the transgene of the zeocin resistance gene in the zeocin-resistant strains transformed. The zeocin gene specific DNA fragments were amplified from the genomic DNA of each transformant strain with PCR technique using zeocin resistant gene specific primers.

Figure 15:
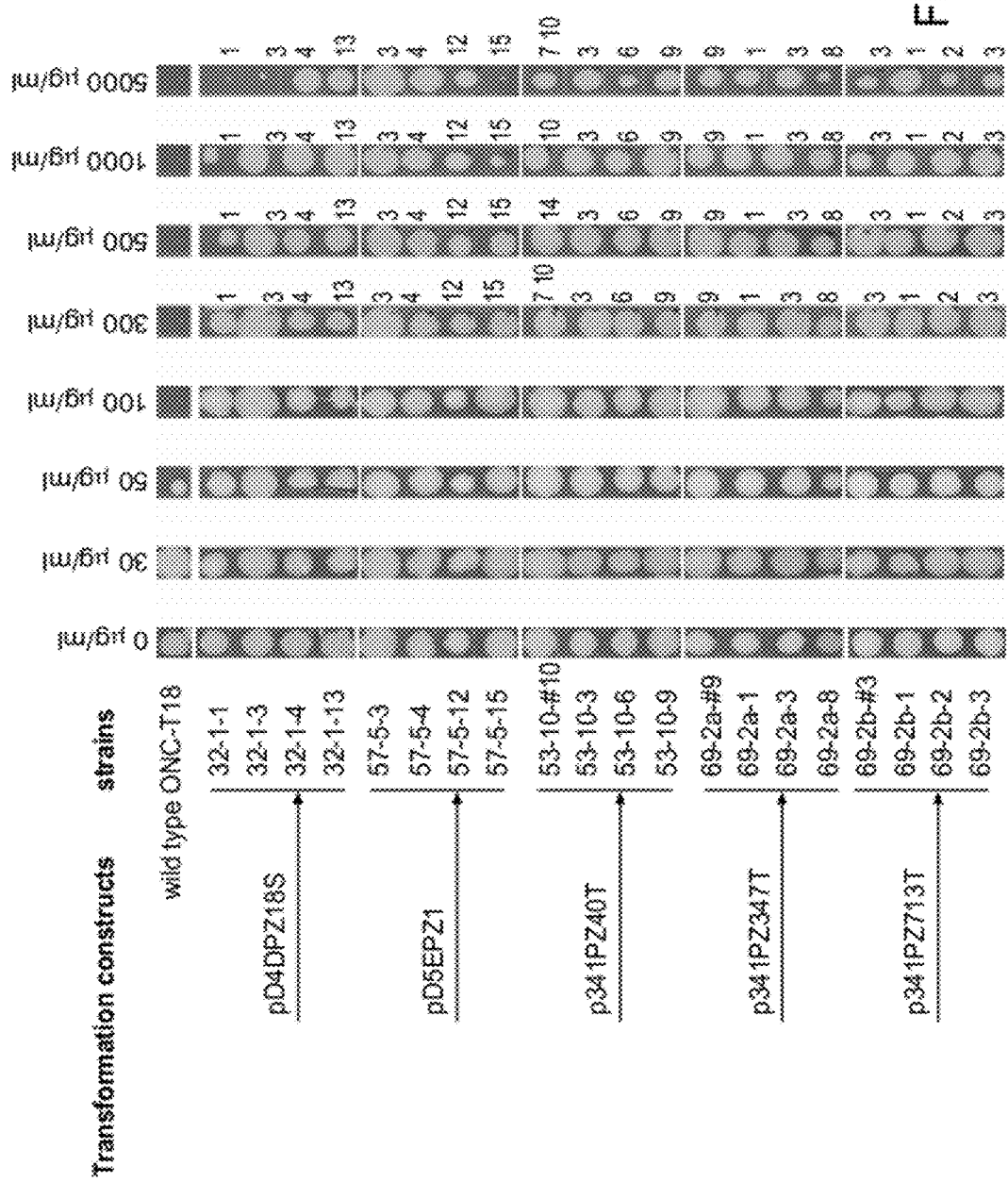

FIG. 15 illustrates the growth rates of the wild type and various transformed ONC-T18 strains in the agar plates of the growth medium (ONC-T18-GM0) containing sea salt at the concentration of 18 g/L or 35 g/L. One μL of the cell suspensions was spotted on the ONC-T18-GM0 agar plates and the diameters of the colonies were measured daily.

Figure 16:
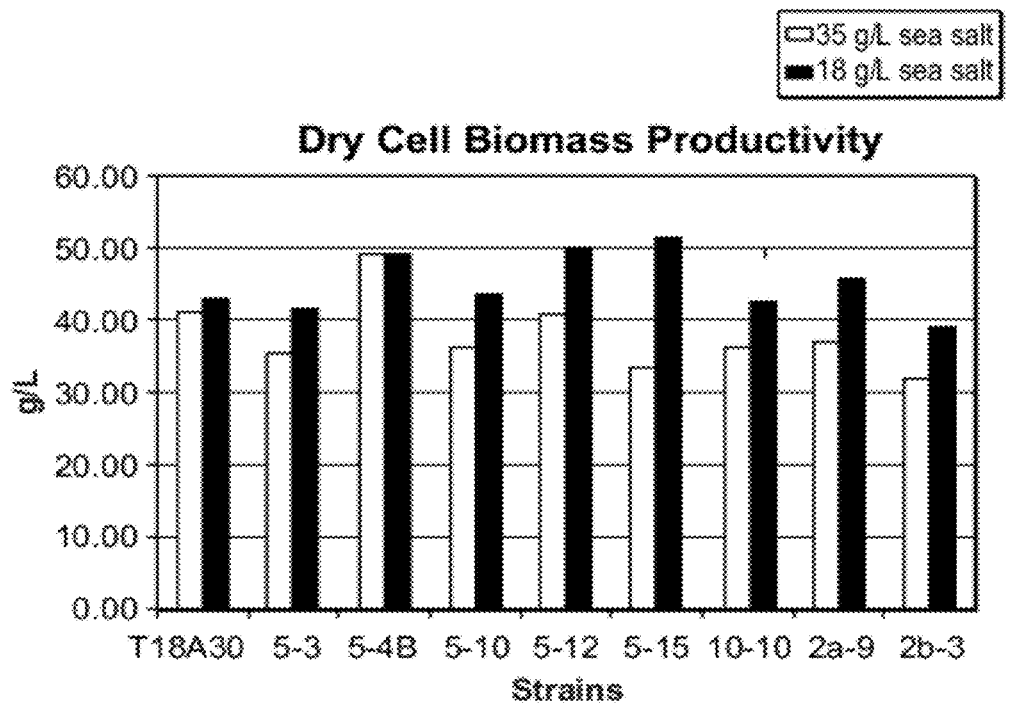

FIG. 16 illustrates the biomass productivity of the wild type and various transformed ONC-T18 strains in liquid growth medium (ONC-T18-GM0) containing artificial sea salt at the concentration of 18 g/L or 35 g/L. Results shows that at the lower salinity, all strains tested produced more biomass than at a higher salinity.

FIG. 17 illustrates DHA productivities of the wild type and various transformed ONC-T18 strains in the liquid growth medium (ONC-T18-GM0) containing artificial sea salt at the concentration of 18 g/L or 35 g/L. Results show that DHA productivities of the transformed strains differentiated in a broad range; most strains produced high DHA yield in lower salinity than at higher salinity, and high DHA yield production strains can be isolated from screening single colony cultures.

FIG. 18 illustrates the fatty acid profiles and total lipid productivities of the transformed strains that grew in liquid ONC-T18-GM0 media having various salinities. This figure illustrates the stability of the ble transgene in ONC-T18 strains transformed.

Figure 19:
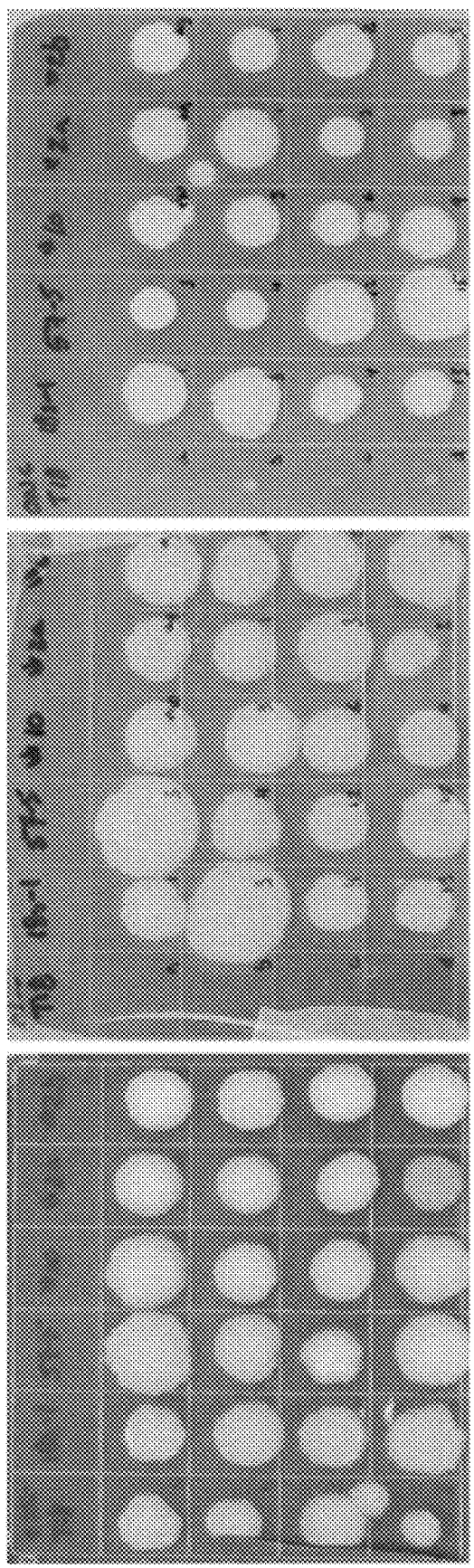

FIG. 19 illustrates a comparison of biomass, lipid, and DHA productivities of a mutagenized ONC-T18 strain and a parental strain.

DEFINITIONS

Competent: The term "competent," as used herein in reference to a cell, refers to the ability of the cell to take up extracellular genetic material. A cell may be competent naturally and/or induced artificially (e.g., in a laboratory) to be competent. In some embodiments, competent cells are able to take up extracellular genetic material when the extracellular genetic material is introduced by a particular method, e.g., a particular method of transformation. For example, a cell may be competent for one method of transformation, but not for another. Alternatively or additionally, a cell may be competent for more than one method of transformation. Competent cells may be obtained from any of a variety of sources. For example, they may be isolated from nature, prepared in the laboratory, and/or bought commercially. In some embodiments, the competence of a cell is transient. In some embodiments, the competence of a cell is permanent.

Component: The term "component," when used herein in reference to a cell, means any part of a cell, such as a structure, part of a structure, macromolecular complex, and/or molecule contained in the cell, including, but not limited to, cell membranes, cell walls, cellular nuclei, cystosol, genetic material (e.g., chromosomes), cellular organelles, or any part of or biomolecule contained in any of the aforementioned components. Organelles typically contained in a cell may differ depending on the cell type. For example, some organelles are present only in eukaryotic cells. Some organelles are only present in plant cells, and some are only present in animal cells. Non-limiting examples of types of organelles are cellular nucleus, mitochondria, chloroplasts, peroxisomes, lysosomes, vacuoles, Golgi apparatus, endoplasmic reticulum, ribosomes, and centrosomes. Non-limiting examples of biomolecules contained in a cell include, but are not limited to, nucleic acids (e.g., DNA and/or RNA), polypeptides (e.g., proteins), nucleo-protein complexes, lipids, and phospholipids. Some cells may contain exogenous genetic material (e.g., material that has been introduced into the cell by the hand of man). Such exogenous material is included in this definition. Some cells may have extracellular components such as extracellular capsules, flagella, or fimbria (pili). These extracellular components are also included in this definition.

Engineered: In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present invention, an engineered polynucleotide comprises a regulatory sequence that is found in nature in operative association with a first coding sequence but not in operative association with a second coding sequence, is linked by the hand of man so that it is operatively associated with the second coding sequence. To give but one specific example that is described herein, in some embodiments of the present invention, a *Thraustochytrium* Δ4 desaturase promoter is linked to nucleic acid encoding a polypeptide other than a *Thraustochytrium* Δ4 desaturase polypeptide. Comparably, a cell or organism is considered to be "engineered" if it has been manipulated so that its genetic information is altered (e.g., new genetic material not previously present has been introduced, for example by transformation, mating, or other mechanism, or previously present genetic material is altered or removed, for example by substitution or deletion mutation). As is common practice and is understood by those in the art, progeny of an engineered polynucleotide or cell are typically still referred to as "engineered" even though the actual manipulation was performed on a prior entity.

Genetic modification: The term "genetic modification", as used herein, refers to a manipulation by the hand of man through the use of genetic engineering. The term "genetic modifications" encompasses any types of changes to the genetic material of a cell, including changes to the nucleotide (e.g., DNA or RNA) sequence of the genetic material of the cell and chemical modifications to the genetic material of the cell (e.g., modifications such as methylation that may affect the expression of a genetic locus). Cells or organisms that are manipulated in such a manner are said to be "genetically modified" or "transgenic". For example, the term "transgenic cell", as used herein, refers to a cell whose DNA contains an exogenous nucleic acid not originally present in the non-transgenic cell. A transgenic cell may be derived or regenerated from a transformed cell or derived from a transgenic cell. Exemplary transgenic cells in the context of the present invention include, but are not limited to, transgenic Thraustochytrid or *Thraustochytrium* cells. Transgenic cells typically express DNA sequences that confer to the cells characteristics different from that of native, non-transgenic cells of the same strain. Progeny of transgenic cells are typically considered transgenic as well.

Heterologous: The term "heterologous", as used herein to refer to nucleic acids (e.g., nucleic acids including regulatory sequences and/or genes) or polypeptides, refers to a nucleic acid or polypeptide that is artificially introduced into a cell and/or does not naturally occur in the cell in which it is present. In some embodiments, a heterologous nucleic acid has a nucleotide sequence that is identical to that of a nucleic acid naturally present in the cell. For example, in some embodiments, a Thraustochytrid host cell is engineered to include a nucleic acid having a Thraustochytrid or *Thraustochytrium* regulatory sequence. Although the Thraustochytrid or *Thraustochytrium* regulatory sequence may naturally occur in the host cell, the introduced nucleic acid is heterologous according to the present disclosure. In many embodiments a heterogous nucleic acid has a nucleotide sequence that is different from that of any nucleic acid that is naturally present in the cell. In some embodiments, a nucleic acid that is heterologous to a particular cell has a nucleic acid sequence that is identical to that of a nucleic acid that is naturally found in a source organism that is different from the cell into which the heterologous nucleic acid is introduced.

Host cell: As used herein, the "host cell" is a cell that is manipulated according to the present disclosure. For example, in some embodiments, a host cell is manipulated such that its production of one or more PUFA is increased (e.g., via PUFA increasing modification). A "modified host cell", as used herein, is any host cell which has been modified, engineered, or manipulated in accordance with the present disclosure as compared with an otherwise identical parental cell, and/or as compared with a particular reference cell (e.g., a wild type cell). In some embodiments, the modified host cell has at least one (and optionally more than one) modification that results in increased production of PUFA or other cellular materials (e.g., at least one PUFA increasing modification) by the modified host cell as compared with the parent or reference cell.

Introduce: The term "introduce", as used herein with reference to introduction of a nucleic acid into a cell or organism is intended to have its broadest meaning and to encompass introduction, for example by transformation methods (e.g., calcium-chloride-mediated transformation, electroporation, particle bombardment), and also introduction by other methods including transduction, conjugation, and mating. In some embodiments, a vector is utilized to introduce a nucleic acid into a cell or organism.

Isolated: The term "isolated", as used herein, means that the isolated entity has been separated from at least one component with which it was previously associated. When most other components have been removed, the isolated entity is "purified" or "concentrated". Isolation and/or purification and/or concentration may be performed using any techniques known in the art including, for example, fractionation, extraction, precipitation, or other separation.

Operably linked: The term "operably linked", as used herein, refers to a relationship between two nucleic acid sequences wherein the expression of one of the nucleic acid sequences is controlled by, regulated by or modulated by the other nucleic acid sequence. In some embodiments, a nucleic acid sequence that is operably linked to a second nucleic acid sequence is covalently linked, either directly or indirectly, to such second sequence, although any effective three-dimensional association is acceptable. A single nucleic acid sequence can be operably linked to multiple other sequences. For example, a single promoter can direct transcription of multiple RNA species.

Polypeptide: The term "polypeptide", as used herein, generally has its art-recognized meaning of a polymer of at least three amino acids. However, the term is also used to refer to specific functional classes of polypeptides, such as, for example, desaturases, elongases, etc. For each such class, the present specification provides several examples of known sequences of such polypeptides. Those of ordinary skill in the art will appreciate, however, that the term "polypeptide" is intended to be sufficiently general as to encompass not only polypeptides having the complete sequence recited herein (or in a reference or database specifically mentioned herein), but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Other regions of similarity and/or identity can be determined by those of ordinary skill in the art by analysis of the sequences of various polypeptides described herein. As is known by those of ordinary skill in the art, a variety of strategies are known, and tools are available, for performing comparisons of amino acid or nucleotide sequences in order to assess degrees of identity and/or similarity. These strategies include, for example, manual alignment, computer assisted sequence alignment and combinations thereof. A number of algorithms (which are generally computer implemented) for performing sequence alignment are widely available, or can be produced by one of skill in the art. Representative algorithms include, e.g., the local homology algorithm of Smith and Waterman (Adv. Appl. Math., 1981, 2: 482); the homology alignment algorithm of Needleman and Wunsch (J. Mol. Biol., 1970, 48: 443); the search for similarity method of Pearson and Lipman (Proc. Natl. Acad. Sci. (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.). Readily available computer programs incorporating such algorithms include, for example, BLASTN, BLASTP, Gapped BLAST, PILEUP, CLUSTALW, etc. When utilizing BLAST and Gapped BLAST programs, default parameters of the respective programs may be used. Alternatively, the practitioner may use non-default parameters depending on his or her experimental and/or other requirements (see for example, the Web site having URL www.ncbi.nlm.nih.gov).

PUFA biosynthetic pathway: A "PUFA biosynthetic pathway" is a biosynthetic pathway that produces PUFA and/or PUFA precursors.

PUFA biosynthesis polypeptide: The term "PUFA biosynthesis polypeptide" as used herein, refers to polypeptides involved in the production of a PUFA such as, but not limited to alpha linolenic acid ("ALA"), arachidonic acid ("ARA"), docosahexanenoic acid ("DHA"), docosapentaenoic acid ("DPA"), eicosapentaenoic acid ("EPA"), gamma-linolenic acid ("GLA"), linoleic acid ("LA") and/or linolenic acid. In some embodiments, PUFA biosynthesis polypeptides are enzymes that catalyze particular steps in a synthesis pathway that ultimately produces a PUFA. In some embodiments, a PUFA biosynthesis polypeptide is a fatty acid synthase. In some embodiments, PUFA biosynthesis polypeptides catalyze elongation of a fatty acid. In some embodiments, PUFA biosynthesis polypeptides catalyze desaturation of a fatty acid. In some embodiments, the term "PUFA biosynthesis polypeptide" may also encompass polypeptides that do not themselves catalyze synthetic reactions, but that regulate expression and/or activity of other polypeptides that do so. PUFA biosynthesis polypeptides include, for example, fatty acid synthase polypeptides, elongase polypeptides, $\Delta 9$ desaturase polypeptides, $\Delta 12$ desaturase polypeptides, $\Delta 6$ desaturase polypeptides, $\Delta 8$ desaturase polypeptides, $\Delta 5$ desaturase polypeptides, $\Delta 4$ desaturase polypeptides, and $\omega 3$ desaturase polypeptides.

PUFA increasing modification: A "PUFA increasing modification", as used herein, refers to a modification of a host cell that increases its production of at least one PUFA. In some embodiments, such increased production results in a level of PUFA that is at least 1%-1000% higher than wild type, e.g., about 1%, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 550%, 600%, 650%, 700%, 750%, 800%, 850%, 900%, 950, 1000% higher than that of the parent cell into which the modification was introduced, and/or than that of a particular reference cell (e.g., a wild type cell). In some embodiments, a PUFA increasing modification increases expression or activity of one or more PUFA biosynthesis polypeptides. In some embodiments, a PUFA increasing modification decreases expression or activity of one or more polypeptides that interferes with expression or activity of a PUFA biosynthesis polypeptide, including for example, by competing with the PUFA biosynthesis polypeptide for access to a substrate. In some embodiments, a PUFA increasing modification comprises introduction of a heterologous nucleic acid into a host cell. In some embodiments, a PUFA increasing modification increases overall levels of fatty acid in a cell. In some embodiments, a PUFA increasing modification increases overall level of one or more particular PUFA in a cell, with or without increasing overall levels of fatty acid in the cell. In some embodiments, a PUFA increasing modification increases levels of PUFA including but not limited to ALA, ARA, DHA, DPA, EPA, GLA, and/or LA.

Progeny: The term "progeny," when used herein in reference to a cell, means a cell that arises from another cell (the "parent cell") (e.g., by cell division or budding) such that the "progeny cell" contains at least some of the genetic material of the parent cell. In some embodiments, the progeny cell contains all of genetic material of the parent cell. In some embodiments, the progeny cell does not contain all of the genetic material of the parent cell. In some embodiments, the progeny cell contains some genetic material in addition to the genetic material of the parent cell. In some such embodiments, the additional genetic material is heterologous to the strain or species of the cell. The term "progeny" is meant to encompass not only direct progeny of a parent cell (e.g. cells that result from one division of or budding from a parent cell), but all indirect progeny of a parent cell (e.g., cells that result from more than one cycle of division of or budding from a parent cell). Thus, a given parent cell may have many cellular progeny, even though that cell may generate only a limited number of (e.g., two) cells in each cycle of division or budding. The term "progeny" is also meant to encompass cells that have undergone one or more manipulations by the hand of man (e.g., genetically manipulated or genetically engineered). Thus, for example, when a parent cell line is genetically manipulated or genetically engineered, all of the cells that arise therefrom are considered progeny of the cell line. All of the progeny of those progeny are also considered progeny of the parent cell line, and so on.

Promoter or Promoter element: As used herein, the terms "promoter" and "promoter element" refer to a polynucleotide that regulates expression of a selected polynucleotide sequence operably linked to the promoter, and that effects expression of the selected polynucleotide sequence in cells. The term "*Thraustochytrium* promoter", as used herein, refers to a promoter that functions in a *Thraustochytrium* cell. The term "Thraustochytrid promoter", as used herein, refers to a promoter that functions in a Thraustochytrid cell.

Reference cell: The phrase "reference cell", as used herein, refers to a cell that is normal with respect to at least one characteristic for comparison purposes. For example, a reference cell for comparing against a genetically engineered cell can be a cell that is not genetically engineered. In some embodiments, a reference cell contains no genetic modifications. In some embodiments, a reference cell is a cell of a wild type strain. In some embodiments, a reference cell contains some genetic modifications characteristic of a particular strain against which it is being compared, but does not contain one or more genetic modifications characteristic of the particular strain against which it is being compared. For example, such a reference cell would be useful for evaluating the effect of the one or more genetic modifications that it does not contain. Thus, for example, the term "reference *Thraus-*

*tochytrium* cell" (or "reference Thraustochytrid cell") means a *Thraustochytrium* cell (or Thraustochytrid cell) of the same or similar strain as the cell to which it is being compared, except that the reference *Thraustochytrium* cell (or reference Thraustochytrid cell) lacks one or more characteristics (e.g., one or more genetic modifications) of a *Thraustochytrium* cell (or Thraustochytrid cell) against which the reference *Thraustochytrium* cell (or reference Thraustochytrid cell) is being compared.

Selectable marker: The phrase "selectable marker," as used herein, refers either to a nucleotide sequence, e.g., a gene, that encodes a product (protein) that allows for selection, or to the gene product (e.g., protein) itself. The term "selectable marker" is used herein as it is generally understood in the art and refers to a marker whose presence within a cell or organism confers a significant growth or survival advantage or disadvantage on the cell or organism under certain defined culture conditions (selective conditions). For example, the conditions may be the presence or absence of a particular compound or a particular environmental condition such as increased temperature, increased radiation, presence of a compound that is toxic in the absence of the marker, etc. The presence or absence of such compound(s) or environmental condition(s) is referred to as a "selective condition" or "selective conditions." By "growth advantage" is meant either enhanced viability (e.g., cells or organisms with the growth advantage have an increased life span, on average, relative to otherwise identical cells), increased rate of proliferation (also referred to herein as "growth rate") relative to otherwise identical cells or organisms, or both. In general, a population of cells having a growth advantage will exhibit fewer dead or nonviable cells and/or a greater rate of cell proliferation that a population of otherwise identical cells lacking the growth advantage. Although typically a selectable marker will confer a growth advantage on a cell, certain selectable markers confer a growth disadvantage on a cell, e.g., they make the cell more susceptible to the deleterious effects of certain compounds or environmental conditions than otherwise identical cells not expressing the marker. Antibiotic resistance markers are a non-limiting example of a class of selectable marker that can be used to select cells that express the marker. In the presence of an appropriate concentration of antibiotic (selective conditions), such a marker confers a growth advantage on a cell that expresses the marker. Thus cells that express the antibiotic resistance marker are able to survive and/or proliferate in the presence of the antibiotic while cells that do not express the antibiotic resistance marker are not able to survive and/or are unable to proliferate in the presence of the antibiotic. For example, a selectable marker of this type that is commonly used in plant cells is the NPTII protein, which encodes a protein that provides resistance against the antibiotic kanamycin. Additional selectable markers include proteins that confer resistance against carbenecillin (e.g., β-lactamases), proteins that confer resistance against gentamicin, hygronycin, etc.). A second non-limiting class of selectable markers are nutritional markers. Such markers are generally enzymes that function in a biosynthetic pathway to produce a compound that is needed for cell growth or survival. In general, under nonselective conditions the required compound is present in the environment or is produced by an alternative pathway in the cell. Under selective conditions, functioning of the biosynthetic pathway, in which the marker is involved, is needed to produce the compound.

Selection agent: The phrase "selection agent," as used herein refers to an agent that introduces a selective pressure on a cell or populations of cells either in favor of or against the cell or population of cells that bear a selectable marker. For example, in certain embodiments, the selection agent is an antibiotic and the selectable marker is an antibiotic resistance gene. In certain exemplary embodiments, zeocin is used as the selection agent.

Source organism: A "source organism", as used herein, is an organism that naturally contains or produces a polynucleotide, polypeptide, or other compound (e.g., a heterologous nucleic acid) that is to be introduced in accordance with the present invention into a recipient or host cell. In some embodiments, the particular source organism to be selected is not essential to the practice of the present disclosure. Relevant considerations may include, for example, how closely related the potential source and host organisms are in evolution, or how related the source organism is with other source organisms from which sequences of other relevant nucleic acids and/or polypeptides have been selected. Where a plurality of different heterologous nucleic acids are to be introduced into and/or expressed by a host cell, different sequences may be from different source organisms, or from the same source organism. To give but one example, in some cases, individual polypeptides may represent individual subunits of a complex protein activity and/or may be required to work in concert with other polypeptides in order to achieve the goals of the present disclosure. In some embodiments, it will often be desirable for such polypeptides to be from the same source organism, and/or to be sufficiently related to function appropriately when expressed together in a host cell. In some embodiments, such polypeptides may be from different, even unrelated source organisms. It will further be understood that, where a heterologous polypeptide is to be expressed in a host cell, it will often be desirable to utilize nucleic acid sequences encoding the polypeptide that have been adjusted to accommodate codon preferences of the host cell and/or to link the encoding sequences with regulatory elements active in the host cell. For example, when the host cell is a *Thraustochytrium* cell, it will often be desirable to alter the gene sequence encoding a given polypeptide such that it conforms more closely to the codon preferences of such a cell. In certain embodiments, a gene sequence encoding a given polypeptide is optimized even when such a gene sequence is derived from the host cell itself (and thus is not heterologous). For example, a gene sequence encoding a polypeptide of interest may not be codon optimized for expression in a given host cell even though such a gene sequence is isolated from the host cell strain. In such embodiments, the gene sequence may be further optimized to account for codon preferences of the host cell. Those of ordinary skill in the art will be aware of host cell codon preferences and will be able to employ the methods and compositions disclosed herein to optimize expression of a given polypeptide in the host cell.

Substrate: A "substrate" as used herein to describe substrates of an enzyme, refers to any entity that can be modified by activity of the enzyme.

Terminator: As used herein, the term "terminator" refers to a polynucleotide that abrogates expression of a selected polynucleotide sequence operably linked to the terminator in cells. In some embodiments, a terminator sequence is downstream of a stop codon in a gene. The term "*Thraustochytrium* terminator", as used herein, refers to a terminator that functions in a *Thraustochytrium* cell. The term "Thraustochytrid terminator", as used herein, refers to a terminator that functions in a Thraustochytrid cell.

Transformation: The term "transformation," as used herein refers to a process by which an exogenous nucleic acid molecule (e.g., a vector or recombinant nucleic acid molecule) is introduced into a recipient cell or microorganism. The exogenous nucleic acid molecule may or may not be integrated into (i.e., covalently linked to) chromosomal DNA making up the genome of the host cell or microorganism. For example, the exogenous polynucleotide may be maintained on an episomal element, such as a plasmid. Alternatively or additionally, the exogenous polynucleotide may become integrated into a chromosome so that it is inherited by daughter cells through chromosome replication. Methods for transformation include, but are not limited to, calcium phosphate precipitation; $Ca^{2+}$ treatment; fusion of recipient cells with bacterial protoplasts containing the recombinant nucleic acid; treatment of the recipient cells with liposomes containing the recombinant nucleic acid; DEAE dextran; fusion using polyethylene glycol (PEG); electroporation; magnetoporation; biolistic delivery; retroviral infection; lipofection; and microinjection of DNA directly into cells. In some circumstances, an exogenous nucleic acid is introduced in to a cell by mating with another cell. For example, in *S. cerevisiae*, cells mate with one another.

Transformed: The term "transformed," as used in reference to cells, refers to cells that have undergone "transformation" as described herein such that the cells carry exogenous genetic material (e.g., a recombinant nucleic acid). The term "transformed" can also or alternatively be used to refer to microorganisms, strains of microorganisms, tissues, organisms, etc.

DETAILED DESCRIPTION OF CERTAIN PARTICULAR EMBODIMENTS

As described herein, the present invention provides a variety of reagents and methods related to the production of PUFA and/or to the modification of Thraustochytrids. In general, the invention relates to modification of Thraustochytrid host cells, and in particular to engineering Thraustochytrids, particularly to increase their production of compounds of interest (e.g., PUFA). The present invention encompasses identification of certain *Thraustochystrium* sp. genetic regulatory elements, as well as the development of methodologies for mutagenesis of Thraustochytrid or *Thraustochytrium*. In certain embodiments, the invention further provides engineered *Thraustochytrium* sp. strains, and products produced from and with them. Certain details of particular embodiments of these and other aspects of the present invention are discussed in more detail below.

Host Cells

As noted, the present invention provides reagents and methodologies for the manipulation of host cells.

In general, identified reagents (e.g., regulatory elements, vectors, selectable markers, mutagenic agents, etc.) and methodologies (including, for example, methods of mutagenizing) may be utilized together with any appropriate host cell. Those of ordinary skill in the art, having read the present disclosure and therefore having such reagents in hand, will readily be able to identify appropriate host cells in which such elements are active.

In some embodiments, host cells for use in accordance with the present invention are Thraustochytrid cells. In some embodiments, host cells are members of the order *Thraustochytriales*. In some embodiments, host cells are members of the Thraustochytriaceae subclass. In some embodiments, host cells are members of a genus selected from the group consisting of *Thraustochytrium, Ulkenia, Schizochytrium, Aurantiochytrium, Aplanochytrium, Botryochytrium, Japonochytrium, Oblongichytrium, Parietichytrium,* and *Sicyoidochytrium*. In some embodiments, host cells are not of the genus *Schizochytrium*.

In some embodiments, host cells utilized in accordance with the present invention are members of the genus *Thraustochytrium*. In some embodiments, a host cell is a *Thraustochytrium* cell from one of the following species: *Thraustochytrium aggregatum, Thraustochytrium aureum, Thraustochytrium gaertnerium, Thraustochytrium kinnei, Thraustochytrium motivum, Thraustochytrium multirudimentale, Thraustochytrium pachydermum, Thraustochytrium roseum, Thraustochytrium* sp. 1.3A4.1, *Thraustochytrium* sp. ATCC 26185, *Thraustochytrium* sp. BL13, *Thraustochytrium* sp. BL14, *Thraustochytrium* sp. BL2, *Thraustochytrium* sp. BL3, *Thraustochytrium* sp. BL4, *Thraustochytrium* sp. BL5, *Thraustochytrium* sp. BL6, *Thraustochytrium* sp. BL7, *Thraustochytrium* sp. BL8, *Thraustochytrium* sp. BL9, *Thraustochytrium* sp. BP3.2.2, *Thraustochytrium* sp. BP3.3.3, *Thraustochytrium* sp. caudivorum, *Thraustochytrium* sp. CHN-1, *Thraustochytrium* sp. FJN-10, *Thraustochytrium* sp. HK1, *Thraustochytrium* sp. HK10, *Thraustochytrium* sp. HK5, *Thraustochytrium* sp. HK8, *Thraustochytrium* sp. HK8a, *Thraustochytrium* sp. KK17-3, *Thraustochytrium* sp. KL1, *Thraustochytrium* sp. KL2, *Thraustochytrium* sp. KL2a, *Thraustochytrium* sp. ONC-T18, *Thraustochytrium* sp. PJA10.2, *Thraustochytrium* sp. TR1.4, *Thraustochytrium* sp. TRR2, *Thraustochytrium striatum,* or *Thraustochytrium visurgense*.

In some embodiments, host cells used in accordance with the present invention are members of the genus *Schizochytrium*. In some embodiments, a host cell is a *Thraustochytrium* cell from one of the following species: *Schizochytrium limacinum, Schizochytrium mangrovei, Schizochytrium minutum, Schizochytrium* sp. (ATCC 20111), *Schizochytrium* sp. (ATCC 20888), *Schizochytrium* sp. BR2.1.2, *Schizochytrium* sp. BUCAAA 032, *Schizochytrium* sp. BUCAAA 093, *Schizochytrium* sp. BUCACD 152, *Schizochytrium* sp. BUCARA 021, *Schizochytrium* sp. BUCHAO 113, *Schizochytrium* sp. BURABQ 133, *Schizochytrium* sp. BURARM 801, *Schizochytrium* sp. BURARM 802, *Schizochytrium* sp. FJU-512, *Schizochytrium* sp. KH105, *Schizochytrium* sp. KR-5, *Schizochytrium* sp. PJ10.4, *Schizochytrium* sp. SEK 210, *Schizochytrium* sp. SEK 345, *Schizochytrium* sp. SEK 346, *Schizochytrium* sp. SR21, or *Schizochytrium* sp. TIO01.

In certain embodiments, a host cell is a *Thraustochytrium* sp. ONC-T18 cell. ONC-T18 is a marine *Thraustochytrium* originally isolated from the leaves of salt marsh grasses in Advocate Harbor, Bay of Fundy, Nova Scotia, Canada. ONC-T18 is described in U.S. Pat. Pub. 2009/0117194, which is herein incorporated by reference in its entirety. In some embodiments, a *Thraustochytrium* cell has an 18s rRNA sequence that is at least 97%, 98%, 99%, 99.1%, 99.2%, 99.3%, 99.4%, 99.5%, 99.6%, 99.7%, 99.8%, 99.9% or more (e.g., including 100%) identical to SEQ ID NO:68. In some embodiments, a host cell is a *Thraustochytrium* sp. ONC-T18 cell from cells deposited under ATCC strain accession number PTA-6245.

Engineering Microorganisms

The present disclosure provides, inter alia, regulatory elements, selectable markers, methods for mutagenesis, and transformation methods for manipulation of microorganisms such as Thraustochytrids. As will be appreciated by those of ordinary skill in the art after consideration of the present disclosure, the tools provided herein can be used alone and in various combinations to implement any desired genetic modification. For example, in certain embodiments, provided transformation methods are used to introduce nucleic acid molecules encoding one or more genes. Nucleic acid molecules can include promoter, terminator, or selectable marker sequences provided herein, or a combination thereof. In certain embodiments, provided methods of mutagenesis are used to generate strains (e.g., Thraustochytrid strains) having desired properties. Such strains may also be transformed (e.g., with nucleic acids including one or more regulatory elements provided herein).

Gene Expression

The present disclosure encompasses compositions and methods for engineering microorganisms. In certain embodiments, the present disclosure provides compositions and methods for engineering Thraustochytrids (e.g., *Thraustochytrium*). "Engineered" cells include cells that have been modified (e.g., by introduction of an exogenous nucleic acid) and progeny thereof that retain the modification.

In some embodiments, the present disclosure provides nucleic acids that include regulatory sequences from Thraustochytrid or *Thraustochytrium*. Gene expression in eukaryotes often requires regulatory sequences that are species-specific, or that function in organisms that are closely related. The availability of regulatory sequences from Thraustochytrid or *Thraustochytrium* allows genes of interest to be expressed in Thraustochytrids. In some embodiments, regulatory sequences include promoter sequences. In some embodiments, regulatory sequences include terminator sequences.

The present disclosure provides an isolated nucleic acid including a Thraustochytrid or *Thraustochytrium* promoter. In some embodiments, a nucleic acid provided herein includes a *Thraustochytrium* Δ4 desaturase gene promoter. A sequence of an exemplary Δ4 desaturase gene promoter is shown in SEQ ID NO:24. In some embodiments, a nucleic acid provided herein includes a *Thraustochytrium* Δ5 elongase gene promoter. A sequence of an exemplary Δ5 elongase gene promoter is shown in SEQ ID NO:19. A *Thraustochytrium* Δ5 elongase gene promoter is a strong promoter in Thraustochytrids (e.g., *Thraustochytrium*). In some embodiments, a nucleic acid provided herein includes a Thraustochytrid or *Thraustochytrium* tubulin gene promoter. Sequences of exemplary *Thraustochytrium* tubulin gene promoters are shown in SEQ ID NOs:6 and 10.

In some embodiments, an isolated nucleic acid including a Thraustochytrid or *Thraustochytrium* promoter provided herein is a cassette, e.g., an expression cassette. In some embodiments, an isolated nucleic acid including a Thraustochytrid or *Thraustochytrium* promoter provided herein is a vector, e.g., an expression vector.

In some embodiments, the present disclosure provides a cell engineered to include a Thraustochytrid or *Thraustochytrium* gene promoter. In some embodiments, a Thraustochytrid or *Thraustochytrium* cell is engineered to include a Thraustochytrid or *Thraustochytrium* promoter, e.g., a *Thraustochytrium* Δ4 desaturase gene promoter, a *Thraustochytrium* Δ5 elongase gene promoter, or a *Thraustochytrium* tubulin gene promoter.

The present disclosure provides an isolated nucleic acid including a Thraustochytrid or *Thraustochytrium* gene terminator. In some embodiments, a nucleic acid provided herein includes a Thraustochytrid or *Thraustochytrium* tubulin gene terminator. Sequences of exemplary *Thraustochytrium* tubulin gene terminators are shown in SEQ ID NOs:14 and 18.

In some embodiments, an isolated nucleic acid including a Thraustochytrid or *Thraustochytrium* gene terminator provided herein is a cassette, e.g., an expression cassette. In some embodiments, an isolated nucleic acid including a Thraustochytrid or *Thraustochytrium* gene terminator provided herein is a vector, e.g., an expression vector.

In some embodiments, provided isolated nucleic acids include one or more gene regulatory elements. In some such embodiments, included gene regulatory elements facilitate inducible gene regulation. Non-limiting examples of inducible systems that may be employed in combination with provided nucleic acids include tetracycline-inducible systems, ethanol inducible systems, and chemically inducible gene expressions systems. (See, e.g. Park and Morschhäuser (2005), Li et al. (2005), and Jepson et al. (1998), the entire contents of each of which are incorporated by reference herein).

Nucleic acids having regulatory sequences provided herein may be operably linked to a heterologous sequence, such as a gene encoding a heterologous polypeptide. For example, in some embodiments, provided are gene expression cassettes that typically comprise a Thraustochytrid or *Thraustochytrium* gene promoter operably linked to heterologous nucleic acid sequence, which is operably linked to a Thraustochytrid or *Thraustochytrium* gene terminator. In some embodiments, the heterologous nucleic acid sequence comprises at least part of a coding sequence in a gene, e.g., the heterologous nucleic acid sequence encodes a gene product such as a polypeptide or RNA. In some embodiments, provided gene expression cassettes further comprise a selection marker (e.g., a zeocin resistance gene such as Sh ble, or any other selection marker discussed herein).

Molecular biology and DNA manipulation procedures can generally be performed according to Sambrook et al. or Ausubel et al. (Sambrook J, Fritsch E F, Maniatis T (eds). 1989. Molecular Cloning. A Laboratory Manual. Cold Spring Harbor Laboratory Press: New York; Ausubel F M, Brent R, Kingston R E, Moore D D, Seidman J G, Smith J A, Struhl K (eds). 1998. Current Protocols in Molecular Biology. Wiley: New York).

Mutagenesis

In another aspect, the present disclosure provides agents and/or methods for mutagenizing microorganisms, as well as strains and/or cells produced by mutagenesis. For example, as described herein, it has been discovered that antibiotics such as bleomycins, phleomycins, and/or tallysomycins can be used to mutagenize microorganisms. The availability of such effective mutagens for microorganisms such as Thraustochytrids (e.g., *Thraustochytrium*) allows for the development of strains having desired features. In particular, the present disclosure demonstrates that zeocin (phleomycin D1) can be used to mutagenize microorganisms such as Thraustochytrids (e.g., *Thraustochytrium*).

The antibiotic zeocin is a basic, water soluble, copper-chelated glycopeptide from culture broth of a *Streptomyces verticillus* mutant (InvivoGen, San Diego, Calif., USA). Zeocin is a member of the phleomycin group of antibiotics, which are glycopeptides that have been widely used as potent anti-tumor agents against lymphomas, head and neck cancers and testicular cancer (Umezawa et al., New antibiotics, bleomycin A and B, Journal of Antibiot., (1966)19:200-209; Sikic et al., Bleomycin Chemotherapy, Academic Press, Orlando, Fla., (1985)). It is generally believed that the molecular mode of action of these antibiotics is related to their ability to bind DNA by intercalation of their planar bithiazole-containing moiety and cleave DNA resulting single strand break or double strand break that causes cell death (Povirk et al., Nucleic Acids Research, (1977) 4:3573-3580). Because of their toxicity toward a broad spectrum of cell types, this group of antibiotics is employed as drugs for positive selection. The present disclosure encompasses the discovery that zeocin is a useful mutagen for industrial microbial strain improvement. Additionally, it is shown herein that at certain concentrations at which zeocin kills most treated cells, surviving cells have increased mutation frequency. The ability to produce cells with increased mutation frequency allows for easier selection and isolation of mutagenized strains.

In some embodiments, the present disclosure provides systems and/or methods for mutagenizing Thraustochytrid cells. In some embodiments, the present disclosure provides systems and methods for mutagenizing cells selected from the group consisting of *Thraustochytrium* cells, *Ulkenia* cells, *Schizochytrium* cells, *Aurantiochytrium* cells, *Aplanochytrium* cells, *Botryochytrium* cells, *Japanochytrium* cells, *Oblongichytrium* cells, *Parietichytrium* cells, *Sicyoidochytrium* cells, fungi of *Mortierella*, heterotrophically grown algae (e.g., a species of the genus *Crypthecodinium*). In some particular embodiments, the present invention provides systems and/or reagents for mutagenesis of ONC-T18.

In certain exemplary embodiments, a microorganism is mutagenized by application to a suitable solid medium (e.g., agar medium) comprising a relevant antibiotic (e.g., zeocin), wherein the antibiotic is present at a concentration below the concentration at which it exhibits complete or nearly complete inhibition of cell growth. Microorganisms used for these methods do not carry a zeocin resistance gene (e.g., Sh ble). In some embodiments, the antibiotic (e.g., zeocin) is used for mutagenesis at a concentration below the concentration at which it kills at least 85%, 90%, 95%, or 100% of cells of that type. In some embodiments, antibiotic (e.g., zeocin) is used for mutagenesis at a concentration above the concentration at which it kills 30%, 40%, 50%, or 60% of cells of that type. In some embodiments, antibiotic (e.g., zeocin) is used for mutation. In some embodiments, antibiotic is used at a concentration and under conditions at which it increases mutation frequency in cells exposed to it above that of spontaneous mutation observed for the cells. In some embodiments, antibiotic is used at a concentration and under conditions at which it inhibits growth or kills 60-80% of cells of that type.

ONC-T18 cells are highly sensitive to zeocin at a concentration of 100 g/mL (see Example 3). Thus, in some embodiments, zeocin is used for mutagenesis at a concentration below 100 g/mL (e.g., at 90, 85, 80, 75, 70, 65, 60, 55, 50, 45, 40, 35, or 30 g/mL). In some embodiments, zeocin is used for mutagenesis at a concentration of about 50 g/mL. In some embodiments, medium in which cells are mutagenized with zeocin has a salt concentration of 18 g/L or less. Mutagenized cells may show morphology changes relative to cells grown at lower concentrations or in the absence of the mutagen. To give but a few examples, in some embodiments, mutagenized cells show altered growth rate, color, and/or total or specific lipid amount.

In certain exemplary methods of mutagenesis, cells (e.g., Thraustochytrid or *Thraustochytrium* cells) are spread onto a solid medium containing antibiotic (e.g., zeocin) at a concentration of 40-60 g/mL. Colonies emerging under these conditions after at least 4 days (e.g., 5, 6, 7, 8, 9, or 10 days) are isolated. Isolated cells can be tested for a desired feature resulting from mutagenesis. For example, cells from mutagenized colonies can be compared to reference cells (e.g., parental cells) to detect a change in a feature, such as biomass and/or lipid productivity.

The present disclosure provides microorganisms (e.g., Thraustochytrid or *Thraustochytrium* isolated by antibiotic (e.g., zeocin) mutagenesis. In some embodiments, a microbial strain (e.g., a *Thraustochytrium* strain) isolated by antibiotic (e.g., zeocin) mutagenesis produces at least 10%, 20%, 30%, 40%, 50% more total lipids than a parental or reference strain. In some embodiments, a Thraustochytrid strain isolated by zeocin mutagenesis produces at least 10%, 20%, 30%, 40%, 50% more ALA, ARA, DHA, DPA, EPA, GLA, and/or LA, or a combination thereof, than a parental strain. In some embodiments, a Thraustochytrid strain isolated by zeocin mutagenesis produces at least 10%, 20%, 30%, 40%, 50% more ARA, DHA, EPA, or a combination thereof, than a parental strain.

One particular strain of ONC-T18 isolated by zeocin mutagenesis produces about 36% more DHA than its parental strain.

Selection

The present disclosure provides methods for selecting microorganisms such as Thraustochytrids (e.g., *Thraustochytrium*). Such methods may be used in conjunction with and/or as a part of, for example, transformation methods as described herein in order genetically manipulate the microorganisms.

Generally, in provided selection methods, a selection agent is used to favor growth of microorganisms bearing a selectable marker suitable for the selection agent over microorganisms that do not bear the selectable marker. Typically the selection agent inhibits, reduces, and/or slows growth of microorganisms that do not bear the selection marker. During selection, microorganisms are typically cultivated in growth medium as described herein, except that the growth medium is supplemented with the selection agent ("selection medium").

In certain selection methods of the present disclosure, microorganisms are cultivated in selection medium for a period of time sufficient to allow the culture to become comprised predominantly of cells that bear the selection marker. That is, during the period of growth in selection medium, cells that do not bear the selection marker do not grow and are overtaken in the culture by cells that do bear the selection marker. In some embodiments, microorganisms are cultivated in selection medium for between 1 to 15 days, 1 to 12 days, or 1 to 9 days. In certain embodiments, microorganisms are cultivated in selection medium for a period of time longer than 1, 2, 3, 4, 5, 6, 7, 8, 9, or 10 days and/or shorter than 50, 45, 40, 35, 30, 25, 20, 15, 14, 13, 12, 11, or 10 days. In certain exemplary embodiments, microorganisms are cultivated in selection medium for between about 3 and about 5 days, or between about 5 and about 10 days, etc. In some embodiments, microorganisms are kept in selection medium after selection. In some embodiments, microorganisms are transferred to a medium without a selection agent for at least a period of time, e.g., during a recovery phase.

In some embodiments, the selectable marker is removed after the cells have been grown for a period of time in selection medium. Removal of the selectable marker may be performed immediately after the period of time the cells are grown in selection medium, after a "recovery period" during which the cells are grown in medium without a selection agent, or later (e.g., after the cells have been stored for a period of time, after the cells have been frozen and then thawed). Methods of genetically engineering cells such that introduced genetic elements (e.g., selectable markers) can later be removed are well known in the art. Such methods typically employ the use of recombinase polypeptides, which typically recognize particular nucleotide sequences ("recognition sites" or "recognition sequences"). For example, a selectable marker can be engineered into a Thraustochytrid or *Thraustochyrium* cell with recognition sites for a particular recombinase flanking the selectable marker. When deletion of the selectable marker is desired, the cells can be exposed to an appropriate recombinase (that is, a recombinase that recognizes the recognition sites flanking the selectable marker), which perform a homologous recombination reaction on the recognition sites, resulting in deletion or inversion of the nucleic acid sequence between the recognition sites.

In some embodiments, the selection agent is or comprises an antibiotic and the selection marker is or comprises a resistance gene for the antibiotic.

In some embodiments, a combination of selection agents is used and/or a combination of selection markers is used.

In certain exemplary embodiments, a microorganism undergoes selection by application to a suitable medium comprising zeocin, wherein the zeocin is present at a concentration above a threshold concentration.

The threshold concentration may correspond approximately to a concentration at which zeocin exhibits complete or nearly complete inhibition of growth of cells that do not contain a zeocin resistance gene. In some embodiments, the threshold concentration is at or above the concentration at which zeocin kills at least 85%, 90%, or 100% of cells of that type that do not contain a zeocin resistance gene. In some embodiments, the threshold concentration may vary depending on culture conditions (e.g., salt concentration, type of culture medium, culture temperature, liquid or solid culture, etc.). In many embodiments, the threshold concentration is above 50 µg/mL. In some embodiments, the threshold concentration is at or above 60, 65, 70, 75, 80, 85, 90, 95, 100, 110, 120, 130, 140, 150, 160, 170, 180, 190, or 200 µg/mL. In some embodiments, the threshold concentration is at or about 100 µg/mL.

In some embodiments, the antibiotic resistance gene is or comprises a phleomycin, belomycin and/or tallysomycin resistance gene. In some embodiments, the antibiotic resistance gene is or comprises a gene (e.g., the ble gene) from *S. hidustanus*.

In some embodiments, the salt concentration of the medium used during selection differs from a salt concentration typically used in medium used for cultivation of the microorganism without selection. In some embodiments, the salt concentration in the medium used during selection is approximately the same as a salt concentration typically used in medium used for cultivation of the microorganism without selection. In certain exemplary embodiments, the salt concentration is between about 10 g/L and about 40 g/L, between about 15 g/L and about 35 g/L, and/or between about 18 g/L and about 35 g/L. In some embodiments, the salt concentration is about 18 g/L. In some embodiments, the salt concentration is about 35 g/L.

In some embodiments, a zeocin concentration at or above 30 µg/mL is used when the culture medium has a salt concentration of about 18 g/L. In some embodiments, a zeocin concentration at or above 100 µg/mL is used when the culture medium has a salt concentration of about 35 g/L.

In certain exemplary embodiments, the suitable medium used during selection is a solid medium. When a solid medium is used, microorganisms may be spread out (e.g., using an inoculation loop, a cell spreader, beads, or other mechanisms for spreading) on a planar surface of the solid medium such that single-cell colonies may be allowed to grow.

Single-cell colonies may be picked and cultivated to obtain larger and/or sufficient quantities for analysis (e.g., transgene analysis, analysis of growth characteristics, analysis of lipid profile, etc.) and/or production of compounds as described herein. Alternatively or additionally, single-cell colonies and/or cultures obtained therefrom may be stored (e.g., by freezing in an appropriate freezing medium) for later use.

Transformation

The present disclosure provides methods for transforming Thraustochytrid (e.g., *Thraustochytrium*) cells. Such methods generally comprise steps of providing a competent Thraustochytrid cell; delivering a heterologous (e.g., recombinant or engineered) nucleic acid into the competent cell, wherein the recombinant nucleic acid comprises a selectable marker; and culturing the competent cell in a culturing medium containing a selection agent that reduces growth of cells without the selectable marker.

Thraustochytrid cells competent for genetic transformation are provided by the present disclosure. In certain exemplary embodiments, competent cells are of the strain ONC-T18. Such competent cells may be provided by any of a variety of methods, a non-limiting example of which is described in greater detail in Example 5. In methods of preparing competent cells such as the one described in Example 5, competent cells are obtained by inoculating solid or liquid medium with inoculum from a desired strain of Thraustochytrid or *Thraustochytrium* and allowing the cells to grow, supplying fresh culture media as necessary. Preparation of competent cells typically involves one or more phases of growth in a liquid medium followed by centrifugation of the cells and resuspension of the cells in sterile liquid to a desired cell density. Competent cells may be prepared fresh as needed for experiments, and/or they may be prepared and then stored (e.g., frozen) for future use.

In some embodiments, cells are grown in flasks (e.g., of volumes of 250 mL, 500 mL, or 1 L).

In some embodiments, cells are grown in a nitrogen-source-rich medium. To give but one example, in some embodiments, cells are grown in a medium with high levels of peptone. In some such embodiments, cells are grown in a medium comprising at least 5-25 g/L of peptone (or other nitrogen source).

In some embodiments, cells are grown in high levels of dissolved oxygen. In some embodiments, cells are agitated during growth, e.g., at about 100 to about 500, or about 125 to about 400, or at about 150 to about 300 rpm.

In some embodiments, cells are mutagenized during vegetative propagation. In some embodiments, cells are mutagenized during vigorous vegetative propagation. In some embodiments, cells are not mutagenized during the zoospore stages.

The heterologous (e.g., recombinant, synthesized (whether chemically or biologically), and/or engineered in that its nucleic acid sequence was selected by the hand of man) nucleic acid may be a DNA, an RNA, an RNA:DNA hybrid, or any suitable derivative thereof. In many embodiments, the recombinant nucleic acid is delivered as part of a vector. Any of a variety of vectors may be suitable for use in accordance with methods of the disclosure including, but not limited to, plasmids, cosmids, BACs (bacterial artificial chromosomes), YACs (yeast artificial chromosomes), and viral vectors. In some embodiments, the heterologous DNA may be or comprise chemically synthesized polynucleotides. In some embodiments, the heterologous DNA may comprise enzymatically synthesized polynucleotides. In some embodiments, heterologous DNA is or comprises a polymerase chain reaction ("PCR") product.

Recombinant or engineered nucleic acids typically comprise a selection marker for use in selection methods as described herein. Typically, the selection marker comprises a gene expression cassette that allows expression of a gene product that, when present in a cell, allows growth of the cell in selection medium containing a selection agent at or above a threshold concentration as described herein. For example, in embodiments wherein an antibiotic is used as a selection agent, the selection marker comprises a gene expression cassette for expressing a corresponding antibiotic resistance gene.

In some embodiments, recombinant or engineered nucleic acids further comprise one or more additional gene expression cassettes for expression one or more desirable gene products. Representative one or more desirable gene products may include, for example, a polypeptide that has commercial value, and/or may be a polypeptide (e.g., an enzyme polypeptide or other biosynthetic pathway component) that is important for the synthesis of one or more downstream products (e.g., compounds such as PUFA) that have commercial value. Alternatively or additionally, a desirable gene product may confer certain desirable characteristics to the microorganism (e.g., suitability for growth in a particular set of conditions; suitability for growth in large-scale production methods, etc.). Alternatively or additionally, a desirable gene product may be one that allows labeling of cells that have been transformed. Alternatively or additionally, in some embodiments, cells are engineered to produce elevated levels of one or more biofuels, drugs, vaccines, antibodies, lipids, resolvins, neuroprotectins, pharmaceutical compounds, polypeptides, etc.

Elements that are typically contained in a gene expression cassette have been described herein, e.g., a promoter or other gene regulatory element that drives expression of the gene, the gene to be expressed, and a terminator sequence that works in the microorganism to be transformed. The gene to be expressed may be referred to as a "transgene." The transgene may in some embodiments be a heterologous gene, e.g., one that is not normally present in the microorganism. Either or both the selection marker and the additional gene expression cassette may include such a heterologous gene.

Accordingly, vectors suitable for use in accordance with methods of the disclosure include gene expression vectors.

In some embodiments, one recombinant nucleic acid is delivered into a microorganism. For example, a microorganism may be transformed with one plasmid construct comprising a recombinant nucleic aid.

In some embodiments, more than one recombinant nucleic acid is delivered into a microorganism. For example, a combination of plasmid constructs (each plasmid construct comprising a recombinant nucleic acid) may be delivered into a microorganism. In some such embodiments, a combination of selection agents and selection markers is used to select for presence of the combination of desired recombinant nucleic acids.

Any of a variety of methods for introducing genetic material (e.g., genetic material comprising a recombinant nucleic acid) into a cell may be suitable for use in accordance with transformation methods of the present disclosure. Introduction methods include, but are not limited to, calcium phosphate precipitation; $Ca^{2+}$ treatment; fusion of recipient cells with bacterial protoplasts containing the recombinant nucleic acid; treatment of the recipient cells with liposomes containing the recombinant nucleic acid; DEAE dextran; fusion using polyethylene glycol (PEG); electroporation; magnetoporation; biolistic delivery; retroviral infection; lipofection; and micro-injection of DNA directly into cells.

In certain exemplary embodiments, a biolistic delivery method (also known as "gene cannon," "particle bombardment," and "micro-projectile" method) is used. In such embodiments, a biolistic device accelerates particles coated with the recombinant nucleic acid to speeds sufficient to penetrate cell membranes (and/or cell walls, if present). In some embodiments, the particles comprise or consist of gold particles. Methods for biolistic delivery of genetic material are known in the art, and equipment and reagents for performing such biolistic deliveries are commercially available. See, e.g., Sanford et al., Part. Sci. Technol. 5:27 (1987), Sanford, J. C., Trends Biotech. 6:299 (1988), Sanford, J. C., Physiol. Plant 79:206 (1990), and Klein et al., Biotechnology 10:268 (1992), the entire contents of each of which is incorporated herein by reference.

In some embodiments, nucleic acids are delivered using a method such as *Agrobacterium*-mediated transformation, protoplast transformation, etc, as would be known and understood by those of ordinary skill in the art.

After delivery of a heterologous (e.g., recombinant or engineered) nucleic acid, cells are cultured in a medium containing a selection agent that reduces growth of cells without the selectable marker, as described herein in the "Selection" section. Cells that are selected (e.g., exhibit presence of the selectable marker and therefore of the recombinant nucleic acid) can be stored, analyzed, and/or grown in larger quantities as desired.

In certain exemplary embodiments, transformed cells are subject to one or more analyses to confirm presence of the recombinant nucleic acid. For example, a PCR analysis may be used to confirm presence of a genetic element, e.g., a transgene and/or a selectable marker, that is part of the recombinant nucleic acid.

Engineered Strains

The present disclosure provides, inter alia, regulatory sequences, transformation methods, methods of mutagenesis, and genetic selection methods that enable manipulation of certain microorganisms such as Thraustochytrids. The compositions and methods provided herein can be used to engineer microorganisms (e.g., Thraustochytrids) for any of a number of applications. As noted above, regulatory sequences and selectable markers provided herein can be used to express any polypeptide of interest in an organism in which the sequences and/or selectable markers are operable (e.g., in Thraustochytrids). In some embodiments a polypeptide from a different organism is expressed. In some embodiments, a polypeptide from the host cell is expressed (e.g., overexpressed).

In some embodiments, microorganisms are engineered to have increased production of a compound of interest. In some embodiments, microorganisms are engineered to have increased production of a fatty acid, an antioxidant, resolvins and/or protectins. Alternatively or additionally, in some embodiments, cells are engineered to produce elevated levels of one or more biofuels, drugs, vaccines, antibodies, lipids, resolvins, neuroprotectins, pharmaceutical compounds, polypeptides, etc.

The present disclosure provides Thraustochytrid microorganisms (e.g., *Thraustochytrium*) that are engineered to have increased production of PUFA. That is, the present disclosure provides engineered Thraustochytrid cells including a PUFA increasing modification. In some embodiments, such microorganisms are engineered to have altered (e.g., increased or decreased) expression of a PUFA biosynthesis polypeptide.

Figure 1:
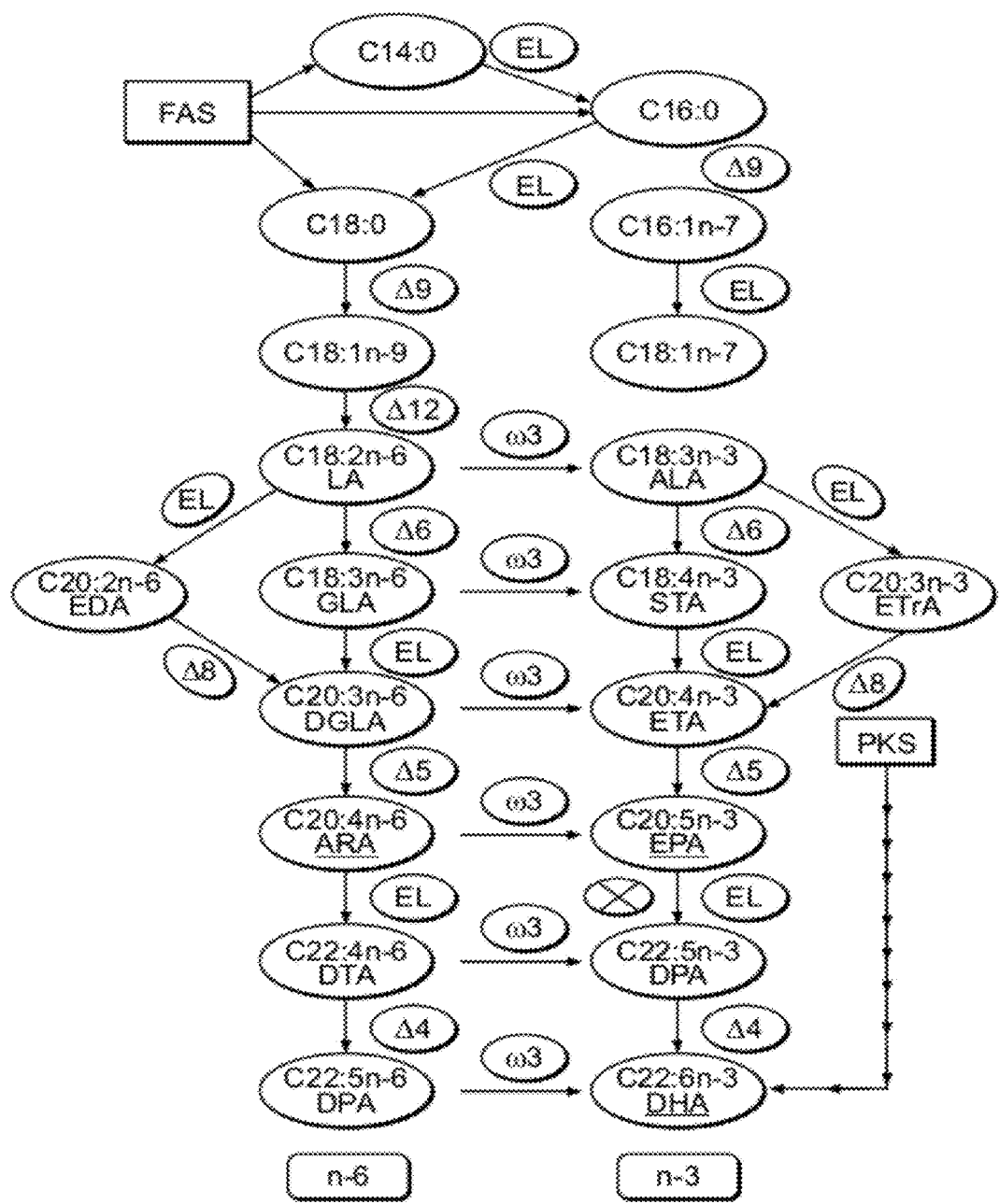
FIG. 1 shows a representation of the putative biosynthetic pathways of PUFA in *Thraustochytrium* sp. ONC-T18 ("ONC-T18", ATCC accession no.: PTA-6245; International Patent Application No. PCT/IB2006/003977, the entire contents of which are herein incorporated by reference). FAS, fatty acid synthase; EL, elongase; Δ8, Δ8 desaturase; Δ5, Δ5 desaturase; Δ4, Δ4 desaturase; ω3, omega-3 desaturase; C14:0, myristic acid; C16:0, palmitic acid; C16:1n-7, palmitoleic acid; C18:0, stearic acid; C18:1n-7, cis-vaccenic acid; C18:1n-9, oleic acid; C18:2n-6 (LA), linoleic acid; C18:3n-3 (ALA), α-linolenic acid; C18:3n-6 (GLA), γ-linolenic acid; C18:4n-3 (STA), stearidonic acid; C20:2n-6 (EDA), eicosadienoic acid; C20:3n-6 (DGLA), dihomo-γ-linolenic acid; C20:4n-3 (ETA), eicosatetraenoic acid; C20:3n-3 (ETE), eicosatetraenoic acid; C20:4n-6 (ARA), arachidonic acid; C20:5n-3 (EPA), eicosapentaenoic acid; C22:4n-6 (DTA), docosatetraenoic acid; C22:5n-3 (DPA), docosapentaenoic acid; C22:5n-6, docosapentaenoic acid; C22:6n-3 (DHA), docosahexaenoic acid; and PKS, polyketide PUFA synthase.

As depicted in FIG. 1, PUFA biosynthesis in ONC-T18 involves generation of fatty acids such as myristic acid (C14:0) and stearic acid (C18:0) by the fatty acid synthase (FAS) enzyme complex, followed by a series of enzymatic reactions on such fatty acids. Each of these reactions is typically catalyzed by either a desaturase (which removes hydrogen atoms to create a carbon-carbon double bond) or an elongase (which lengthen fatty acids by adding two carbon atoms to the fatty acid's carboxylic acid end). The polyketide PUFA synthase (PKS) complex also generates DHA in ONC-T18. PUFA biosynthesis in ONC-T18 appears to have at least two intersecting biosynthetic pathways: the omega-6 and the omega-3

PUFA biosynthetic pathways. Conversion of omega-6 fatty acids to omega-3 fatty acids can be catalyzed by omega-3 desaturase. Thus, as depicted in FIG. 1, a variety of fatty acids are produced at various points in the pathway.

In some embodiments, expression of one or more genes encoding enzyme polypeptides in the pathway is regulated to increase production of particular PUFA and/or other fatty acids as desired. For example, expression of the FAS gene may be downregulated to increase PUFA production. Downregulation of expression of the Δ5 elongase, Δ4 desaturase, and/or any of the PKS genes may increase EPA production and/or PUFA production. Downregulation of expression of any one of the PKS genes may increase ARA production. Upregulation of expression of any of the PKS genes may increase DHA production. Upregulation of expression the Δ12 elongase gene may increase ARA and EPA production.

In some embodiments, expression of one or more genes encoding enzyme polypeptides in the pathway is regulated to produce biofuels. For example, downregulation of expression of any of the PKS, Δ9 desaturase, elongase, and omega-3 desaturase genes, and/or upregulation of FAS gene expression may increase production of short chain lipids for use as biofuel stocks.

In some embodiments, alteration (e.g., downregulation or upregulation) of gene expression of a pathway component is accomplished by generating a gene knockout by, e.g., homologous recombination. Typically, a linearized DNA construct is introduced into cells using any of a variety of techniques including, but not limited to, biolistic projectile DNA delivery. In some embodiments, the frequency of homologous recombination in ONC-T18 is greater than about 50%, 55%, 60%, 65%, 70%, 75%, 80%, 85%, or 90%.

In some embodiments alteration (e.g., downregulation or upregulation) of gene expression of a pathway component is accomplished by mutagenesis of one or more gene targets.

In some embodiments, engineered microorganisms provided herein can produce a lipid fraction comprising n-3 DHA, EPA and n-6 DPA at greater than about 4.0 g/L of medium. In some embodiments, microorganisms provided herein can produce a lipid composition comprising n-3 DHA, EPA and n-6 DPA at greater than about 20.0 g/L of medium. In some embodiments, microorganisms can produce a lipid composition comprising n-3 DHA, EPA and n-6 DPA at greater than about 14.0 g/L of medium. In some embodiments, microorganisms can produce from about 1.5 g/L to about 5.0 g/L (e.g., about 4.6 g/L) of the n-3 DHA, from about 0.5 g/L to about 1.5 g/L (e.g., about 0.22 g/L) of the n-3 EPA, and from about 0.5 g/L to about 1.5 g/L of the n-6 DPA. In some embodiments, engineered microorganisms provided herein can produce a lipid composition comprising n-3 DHA, EPA, n-6 DPA, or ARA at a yield up to about 120 g/L, which corresponds to more than about 75% of total lipids. In some embodiments, engineered microorganisms provided herein can produce a lipid composition comprising short chain fatty acids (typically C12-C18 fatty acids) at a yield up to about 128 g/L, which corresponds to more than about 80% of total lipids. Furthermore, the microorganism can produce a lipid fraction comprising myristic, myristoleic, pentadecanoic, palmitic, palmitoleic, stearic oleic, linoleic, alpha-linolenic, gamma-linolenic, eicosadienoic, arachidonic, eicosapentaenoic, docosahexanoic, and docosapentaenoic acids greater than 300 mg/g or even 800 mg/g of cellular biomass. In some embodiments, the microorganism can also produce a fraction comprising between 44.3 and 57 mg/g myristic acid (equal to 1134.5 to 1458.1 mg/L), 0.5 to 0.65 mg/g myristoleic acid (equal to 13.3 to 16.63 mg/L), 33.5 to 34.6 mg/g, pentadecanoic acid (equal to 856.9 to 885.1 mg/L), 121.9 and 165.1 mg/g palmitic acid (equal to 3118.2 to 4923.3 mg/L), 7.9 to 28.5 mg/g palmitoleic acid (equal to 202.1 to 729 mg/L), 4.38 to 5.9 mg/g stearic acid (equal to 112 to 151 mg/L), 6.94 to 9.9 mg/g oleic acid (equal to 177.5 to 253.2 mg/L), 0.4 to 1.3 mg/g linoleic acid (equal to 11.26 to 33.3 mg/L), 0.5 to 1.0 mg/g eicosadienoic acid (equal to 12.8 to 25.6 mg/L), 0.4 to 0.5 mg/g arachidonic acid (equal to 10.2 to 13 mg/L), 75 to 100 mg/g docosahexanoic acid (equal to 1918 to 2560 mg/L), 1.9 to 6 mg/g eicosapenatenoic acid (equal to 48.6 to 153.5 mg/L) and 17.1 to 33.7 mg/g docosapentaenoic acid (equal to 437.4 to 862.1 mg/L), having a total fatty acid content within the cellular biomass of between 301 to 800 mg/g (equal to 7700 to 20,209 mg/L).

Fermentation and Production

Certain methods of the invention include or can be used in conjunction with steps of culturing a microorganism (e.g., a Thraustochytrid, e.g., a *Thraustochytrium* sp.). Cultivation methods for Thraustochytrids have been described, e.g., in U.S. Patent Publication US2009/0117194A1, the entire contents of which are herein incorporated by reference. Typically, microorganisms are grown in a growth medium (also known as "culture medium"). Any of a variety of media may be suitable for use in accordance with selection methods of the present invention. Typically the medium supplies various nutritional components, including a carbon source and a nitrogen source, for the microorganism.

Microorganisms provided herein can be cultivated under conditions that increase biomass and/or production of a compound of interest. Thraustochytrids are typically cultured in saline media. For example, Thraustochytrids can be cultured in medium having a salt concentration between about 2.0-50.0 g/L. In some embodiments, Thraustochytrids are cultured in media having a salt concentration between about 2-35 g/L. In some embodiments, Thraustochytrids are cultured in a medium having a salt concentration between about 18-35 g/L. It has been found under certain circumstances that Thraustochytrids grow well in low salt conditions. In some embodiments, Thraustochytrids are cultured in a medium having a salt concentration between about 5-20 g/L. In some embodiments, Thraustochytrids are cultured in a medium having a salt concentration between about 5-15 g/L. Culture media may or may not include NaCl. Culture media may or may not include addition of NaCl. In some embodiments, a medium contains artificial sea salt, e.g., INSTANT OCEAN™, Aquaria, Inc. Culture media may or may not include natural or artificial seawater. In some embodiments, a medium contains natural or artificial seawater, e.g., from about 2% to 100% seawater.

Chloride ions may cause corrosion of the fermentor or other downstream processing equipment. In some embodiments, the chloride concentration in culture media is reduced. In some embodiments, culture media include non-chloride-containing sodium salts (e.g., sodium sulfate) as a source of sodium. For example, a significant portion of the total sodium may be supplied by non-chloride salts such that less than about 100%, 75%, 50%, or 25% of the total sodium in culture media is supplied by sodium chloride.

In some embodiments, culture media have chloride concentrations of less than about 3 g/L, 500 mg/L, 250 mg/L, or 120 mg/L. In some embodiments, culture media have chloride concentrations of between about 60 mg/L and 120 mg/L.

Examples of non-chloride sodium salts suitable for use in accordance with the present invention include, but are not limited to, soda ash (a mixture of sodium carbonate and sodium oxide), sodium carbonate, sodium bicarbonate, sodium sulfate, and mixtures thereof. See, e.g., U.S. Pat. Nos.

5,340,742 and 6,607,900, the entire contents of each of which are incorporated by reference herein.

Media for Thraustochytrid culture can include any of a variety of carbon sources. Examples of carbon sources include fatty acids; lipids; glycerols; triglycerols; carbohydrates such as glucose, starch, celluloses, hemicelluloses, fructose, dextrose, xylose, lactulose, galactose, maltotriose, maltose, lactose, glycogen, gelatin, starch (corn or wheat), acetate, m-inositol (derived from corn steep liquor), galacturonic acid (derived from pectin), L-fucose (derived from galactose), gentiobiose, glucosamine, alpha-D-glucose-1-phosphate (derived from glucose), cellobiose, dextrin, and alpha-cyclodextrin (derived from starch); sucrose (from molasses); polyols such as maltitol, erythritol, adonitol and oleic acids such as glycerol and tween 80; amino sugars such as N-acetyl-D-galactosamine, N-acetyl-D-glucosamine and N-acetyl-beta-D-mannosamine; and any kind of biomass or waste stream.

In some embodiments, media include carbon sources at a concentration of about 5 g/L to about 200 g/L. In some embodiments, media have a C:N (carbon to nitrogen ratio) ratio between about 1:1 and about 40:1. In some embodiments in which two-phase cultures are used, media have a C:N ratio of between about 1:1 to about 5:1 for the first phase, then about 1:1 to about 1:~0 (i.e., no or nearly no nitrogen) in the second phase.

Media for Thraustochytrids culture can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$), peptone, tryptone, yeast extract, malt extract, fish meal, sodium glutamate, soy extract, casamino acids and distiller grains. Concentrations of nitrogen sources in suitable media typically range between about 1 g/L and about 25 g/L.

In some embodiments, media include a phosphate, such as potassium phosphate or sodium-phosphate. Inorganic salts and trace nutrients in media can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Vitamins such as pyridoxine hydrochloride, thiamine hydrochloride, calcium pantothenate, p-aminobenzoic acid, riboflavin, nicotinic acid, biotin, folic acid and vitamin B12 can be included.

For example, a suitable medium might be comprised of between about 11 and about 13 g/L (e.g., about 12 g/L) sodium sulfate, between about 0.45 and about 0.55 g/L (e.g., about 0.5 g/L) KCl, between about 1.8 and about 2.2 g/L (e.g., about 2 g/L) $MgSO_4.7H_2O$, between about 0.3 and about 0.4 g/L (e.g., about 0.35 g/L) Hodag K-60 antifoam, between about 0.60 and about 0.70 g/L (e.g. about 0.65 g/L) $K_2SO_4$, between about 0.9 and about 1.1 g/L (e.g., about 1.0 g/L) $KH_2PO_4$, between about 0.95 and about 1.1 g/L (e.g., about 1 g/L) $(NH_4)_2SO_4$, between about 0.15 and about 0.19 (e.g., about 0.17 g/L) $CaCl_2.H_2O$, between about 2 and about 10 g/L (e.g., about 4.5 g/L) 95 DE corn syrup (solids basis), between about 2.7 and about 3.3 mg/L (e.g., about 3 mg/mL) $MnCl_2.4H_2O$, between about 2.7 and about 3.3 mg/L (e.g., about 3 mg/mL) $ZnSO_4.7H_2O$, between about 0.035 and about 0.045 mg/L (e.g., about 0.04 mg/L) $CoCl_2.6H_2O$, between about 0 and about 0.045 mg/L (e.g., about 0.04 mg/L) $Na_2MoO_4.2H_2O$), between about 1.8 and about 2.2 mg/L (e.g., about 2 mg/L) $CuSO_4.5H_2O$, between about 1.8 and about 2.2 mg/L (e.g., about 2 mg/L) $NiSO_4.6H_2O$, between about 9 and about 11 mg/L (e.g., about 10 mg/L) $FeSO_4.7H_2O$, between about 4 and about 15 mg/L (e.g., about 9.5 mh/L) thiamine, between about 0.05 and about 0.25 mg/L (e.g., about 0.15 mg/L) vitamin $B_{12}$, between about 1.3 and about 5.1 (e.g., about 3.2 mg·L) calcium pantothenate, and about 28% $NH_4OH$ solution.

The pH of medium is adjusted to between 3.0 and 10.0 using acid or base where appropriate, and/or using the nitrogen source. In some embodiments, medium is adjusted to have a between pH 4.0 and 6.5. Medium can be sterilized.

In some embodiments, a medium used for culture of a microorganism is a liquid medium. In some embodiments, a medium used for culture of a microorganism is a solid medium. In addition to carbon and nitrogen sources as discussed herein, a solid medium may contain one or more components (e.g., agar or agarose) that provide structural support and/or allow the medium to be in solid form.

Cells can be cultivated for anywhere from 1-60 days. In some embodiments, cultivation is carried out for 14, 13, 12, 11, 10, 9, 8, 7, 6, 5, 4, 3, 2, or 1 days, or less. In some embodiments, cultivation is carried out at temperatures between 4 to 30° C., e.g., 18 to 28° C. In some embodiments, cultivation includes aeration-shaking culture, shaking culture, stationary culture, batch culture, semi-continuous culture, continuous culture, rolling batch culture, or wave culture, or the like. Cultivation can be carried out using a conventional agitation-fermenter, a bubble column fermenter (batch or continuous cultures), a wave fermentor, etc.

In some embodiments, cultures are aerated by shaking. In some embodiments, shaking ranges from 100 to 1000 rpm, e.g., from 350 to 600 rpm, from 1000 and 450 rpm. In some embodiments, cultures are aerated differently (e.g., using different shaking speeds) during biomass-producing phases as they are during lipid-producing phases. For example, in some embodiments, cultures are aerated by shaking at a speed between about 150 and about 350 rpm during biomass phases and at a speed between about 30 and about 120 rpm during lipid-producing phases. Alternatively or additionally, shaking speeds may vary depending on the type of culture vessel (e.g., shape or size of flask).

In some embodiments, the level of dissolved oxygen (DO) is higher during the biomass production phase than it is during the lipid production phase, e.g., DO levels are reduced during the lipid production phase. In some embodiments, the level of dissolved oxygen is reduced below saturation; in some embodiments, the level of dissolved oxygen is reduced to a very low, or even undetectable, level.

It has been discovered that production of desirable lipids can be enhanced by culturing cells in according to methods that involve a shift of one or more culture conditions in order to obtain higher quantities of desirable compounds. In some embodiments, cells are cultured first under conditions that maximize biomass, followed by a shift of one or more culture conditions to conditions that favor lipid productivity. Conditions that are shifted can include oxygen concentration, C:N ratio, temperature, and combinations thereof. In certain embodiments, a two-stage culture is performed in which a first stage favors biomass production (e.g., using conditions of high oxygen (e.g., generally or relative to the second stage), low C:N ratio, and ambient temperature), followed by a second stage that favors lipid production (e.g., in which oxygen is decreased, C:N ratio is increased, and temperature is decreased). That is, in some embodiments, the present invention provides methods that involve culturing cells under a first set of conditions that includes one or more conditions selected from the group consisting of a first oxygen concentration, a first C:N ratio, a first temperature, and combinations thereof. Culturing under this first set of conditions continues for a first time period, the duration of which may vary. At the end of the first time period (which is not necessarily a discrete point in time), one or more conditions are altered so that cells are cultured under a second set of conditions that includes one or more conditions selected from the group consisting of a second oxygen concentration, a second C:N ratio, a second temperature, and combinations thereof. In some embodiments, some conditions are changed at the end of the first time period, and some are maintained until the end of a second time period at which time one or more conditions may be changed again, and/or one or more conditions may be changed for a first time. In some embodiments, the first C:N ratio in within the range of about 2:1 to about 1:1; and the first temperature is within the range of about 10 to about 30° C. In some embodiments, the second C:N ratio is about 1:~0; and the second temperature is within the range of about 15 to about 30° C.

In some embodiments, a shift from a first condition to a second condition is performed and/or occurs gradually; in some embodiments, the shift from a first condition to a second condition is performed and/or occurs abruptly.

In some embodiments of culture methods provided herein, oxygen concentration is shifted (e.g., decreased) during cultivation in a number of possible ways including, for example, by shifting the intensity of aeration.

In some embodiments of culture methods provided herein, temperature is shifted (e.g., decreased) during cultivation by at least 2° C. In some embodiments, temperature is shifted by 3° C., 4° C., 5° C., 6° C., 7° C., 8° C., 9° C., or 10° C. In some embodiments, temperature is shifted from about 25° C. to about 20° C.

Cells' productivity for compounds of interest can be evaluated by any available method(s).

Products

PUFA and other compounds produced according to the present disclosure can be utilized in any of a variety of applications, for example exploiting their biological or nutritional properties. In some embodiments of the present disclosure, compounds are used in pharmaceuticals, food supplements, animal feed additives, cosmetics, etc. Compounds produced in accordance with the present disclosure may also be used as intermediates in the production of other compounds.

It will be appreciated that, in some embodiments of the present disclosure, PUFA and/or other compounds produced by manipulated cells as described herein are incorporated into a final product (e.g., food or feed supplement, infant formula, pharmaceutical, etc.) in the context of the host cell. For example, host cells may be lyophilized, freeze dried, frozen, pasteurized, or otherwise inactivated, and then whole cells may be incorporated into or used as the final product. In some embodiments, a host cell (whether or not dried) may be further processed prior to incorporation in the product (e.g., via lysis, sonication, bead milling, pressure treatment, freeze-thawing, pulsed field electrophoresis (PFE) to separate components, and/or enzyme treatment, or combinations thereof; in some embodiments, at least two or more such processes are utilized). Lysed cells can be extracted into an oil using an appropriate solvent and refined using well known processes. In some embodiments, a final product incorporates only a portion of the host cell (e.g., fractionated by size, solubility), separated from the whole. For example, in some embodiments of the disclosure, lipids are isolated from the host cells and are incorporated into or used as the final product. Lipids containing PUFA can be extracted using supercritical fluid extraction, or extraction with one or more solvents (e.g., acetone, chloroform, isopropanol, hexane, methylene chloride, or methanol). In some embodiments, lipids are concentrated by any of a variety of methods, such as urea complexation, column chromatography, and/or supercritical fluid fractionation. Techniques for concentration of solvent-extracted lipids include hydrolysis (e.g., using base, acid, or enzymatic hydrolysis), further extraction, acidification, crystallization, filtration, and combinations thereof (see, e.g., U.S. Pat. Pub. 2009/0117194).

In some embodiments of the present disclosure, one or more produced PUFA and/or other compounds are incorporated into a component of food or feed (e.g., a food supplement). Types of food products into which compounds can be incorporated according to the present disclosure are not particularly limited, and include beverages such as milk, water, sports drinks, energy drinks, teas, and juices; confections such as jellies and biscuits; fat-containing foods and beverages such as dairy products; processed food products such as soft rice (or porridge); infant formulae; breakfast cereals; or the like. In some embodiments, one or more produced compounds is incorporated into a dietary supplement, such as for example a multivitamin. In certain embodiments, a PUFA compound produced according to the present disclosure is included in a dietary supplement and may be directly incorporated into a component of food or feed (e.g., a food supplement).

Examples of feedstuffs into which compounds produced in accordance with the present disclosure may be incorporated include, for instance, pet foods such as cat foods, dog foods and the like, feeds for aquarium fish, cultured fish or crustaceans, etc., feed for farm-raised animals (including livestock and fish or crustaceans raised in aquaculture). Food or feed material into which the compound(s) produced in accordance with the present disclosure is incorporated is preferably palatable to the organism which is the intended recipient. This food or feed material may have any physical properties currently known for a food material (e.g., solid, liquid, soft).

In some embodiments, one or more produced compounds (e.g., PUFA) is incorporated into a pharmaceutical. Examples of such pharmaceuticals include, for instance, various types of tablets, capsules, drinkable agents, etc. In some embodiments, the pharmaceutical is suitable for topical application. Dosage forms are not particularly limited, and include capsules, oils, granula, granula subtilae, pulveres, tabellae, pilulae, trochisci, or the like. Oils and oil-filled capsules may provide additional advantages both because of their lack of ingredient decomposition during manufacturing, and because PUFA-containing lipid droplets may be readily incorporated into oil-based formulations.

Pharmaceuticals according to the present disclosure may be prepared according to techniques established in the art including, for example, the common procedure as described in the United States Pharmacopoeia, for example.

Compounds produced according to the present disclosure (whether isolated or in the context of cells) may be incorporated into products as described herein by combinations with any of a variety of agents. For instance, such compounds may be combined with one or more binders or fillers. In some embodiments, inventive products will include one or more chelating agents, pigments, salts, surfactants, moisturizers, viscosity modifiers, thickeners, emollients, fragrances, preservatives, etc., and combinations thereof.

EXAMPLES

Example 1

Isolation and Identification of Promoter and Terminator Sequences

This example describes identification and isolation of certain exemplary gene expression promoter and terminator nucleic acid sequences from ONC-T18.

Ocean Nutrition Canada Limited has largely sequenced the genome of ONC-T18 using both shot-gun sequencing and pyrosequencing (GS-20; 454) techniques. Among other things, the present disclosure provides analysis of such sequence information, for example utilizing publicly available EST (expressed sequence tag) collection information (Huang et al., 2008), the functional annotation of and/or bioinformatics software (e.g., Kodon package available from Applied Maths and/or one or more algorithms such as BLAST). To provide tools for expression of homologous and heterologous genes (e.g., genes involved in lipid and fatty acid biosynthesis within Thraustochytrid microbes), housekeeping tubulin gene promoters and terminators and desaturase and elongase promoters were cloned from genomic DNA of *Thraustochytrium* sp. ONC-T18 using polymerase chain reaction (PCR) techniques.

1. Isolation and Identification of a Tubulin Gene Promoter #701.

Oligonucleotide primers #52 (SEQ ID NO: 1) and #53 (SEQ ID NO: 2) were designed based on the *Thraustochytrium* sp. ONC-T18 genomic sequence data using the bioinformatics software package Kodon (Applied Maths). Oligonucleotide primers were synthesized and purchased from Invitrogen (California, USA).

Genomic DNA of ONC-T18 was extracted from cells cultured in the growth medium (ONC-T18-GM0) at 25° C. for 36 hours in a shaker incubator with constant agitation at 150 rpm. Cells of 50 mL cultures were harvested by centrifugation for 5 min at room temperature at 4300 rpm in a Sorvall Super T21 centrifuge with the rotor ST-H750 with the adapter Sorvall #00436. Genomic DNA was isolated from the cells using the Ultraclean Microbial DNA Isolation kit (MO BIO Laboratories, Inc, Solana Beach, Calif.) following the manufacturer's protocol.

The components of the growth medium ONC-T18-GM0 are: 5 g/L yeast extract (RM668, HiMedia labs), 5 g/L soy peptone (RM007, HiMedia labs), 10 g/L D(+)-glucose (CERELOSE™ Dextrose 020010, Corn Products International), 35 g/L artificial sea salt (INSTANT OCEAN™, Aquaria, Inc.), 1.25 mg/L trace elements (5 g/L $NaH_2PO_4.H_2O$, 3.15 g/L $FeCl_3.6H_2O$, 4.36 g/L $Na_2EDTA.2\ H_2O$, 0.6125 mg/L $CuSO_4.5H_2O$, 0.0597 g/L $Na_2MoO_4.2H_2O$, 0.022 g/L $ZnSO_4.7H_2O$, 0.01 g/L $CoCl_2.6H_2O$, 0.18 g/L $MnCl_2.4H_2O$, 13 µg/L $H_2SeO_3$, 2.7 mg/L $NiSO_4.6H_2O$, 1.84 mg/L $Na_3VO_4$ and 1.94 mg/L $K_2CrO_4$) and 1.25 mg/L vitamins (1 mg/L vitamin B12, 1 mg/L biotin, 0.20 g/L thiamine HCl).

The tubulin gene promoter #701 including the partial open reading frame sequence was amplified from genomic DNA of ONC-T18 using the following PCR conditions: 94° C. for 1 minute, 94° C. for 30 seconds and 68° C. for 6 minutes and repeated for 30 cycles, and 72° C. for 10 minutes. PCR was carried out in a 50 µL reaction mixture containing 2.5 units TaKaRa LA Taq™ DNA Polymerase (TAKARA BIO INC., Shiga, Japan), 1×LA PCR Buffer II, dNTP Mixture (0.40 mM each), 225 ηg of the template genomic DNA, 0.20 µM primer #52 and 0.20 µM primer #53.

PCR products were resolved in 0.8% agarose gel for electrophoresis at 65 voltages for 60 minutes. Bands with the expected sizes were cut out with a razor blade and DNAs were extracted and purified with QIAquick Gel Extraction Kit (Qiagen, Valencia, Calif.) as per manufacturer's protocol.

The purified DNA fragments were cloned into pT7Blue-3 vector using Perfectly Blunt® Cloning Kits (Novagen, San Diego, Calif.) as per manufacturer's protocol. Positive clones were screened using direct colony PCR method. Briefly, transformed *Escherichia coli* colonies were picked with toothpicks and swirled in a 20 µL PCR reaction mixture containing following components: Taq DNA polymerase (Sigma), 1×PRC buffer, 2.5 mM $MgCl_2$, dNTPs mixture (0.20 mM each), 0.25 µM primer #62 (SEQ ID NO: 3) and 0.25 µM primer #63 (SEQ ID NO:4) in a 200 µL PCR tube, respectively. Meanwhile colonies were also streaked on a reference plate for the isolation of plasmid DNAs.

The PCR was carried out under the following conditions: 94° C. for 3 minute for one cycle; 94° C. for 1 minute, 53° C. for 2 minutes and 72° C. for 4 minutes, and repeated for 30 cycles; and 72° C. for 10 minutes. PCR products were differentiated in 0.8% agarose gel. Colonies from which a PCR product of the expected size was amplified were considered to be positive colonies.

Plasmid DNA of the positive clone JZ2-17-10 was isolated from the bacterial *E. coli* cells of 3 mL culture using Zyppy™ Plasmid Miniprep Kit (Zymo Research Corp., Orange, Calif.). Its insert was sequenced using the forward primer #62 (SEQ ID NO:3) and the reverse primer #63 (SEQ ID NO: 4). The resulting sequences were assembled and analyzed using bioinformatics software package Kodon (Applied Maths) and algorithms BLAST. The nucleotide sequence of the insert from the clone JZ2-17-10 is 724 base pairs long (SEQ ID NO: 5). The 498 nucleotides upstream of the putative translation start code ATG of a partial putative tubulin gene open-reading frame (ORF) was determined to be a putative gene expression promoter (sequence #701; SEQ ID NO: 6) based on analyses using various bioinformatics software. Typical gene promoter elements were identified within this sequence. A search for sequences homologous to this putative promoter sequence #701 (SEQ ID NO: 6) was performed in various databases of the GenBank including the database of the patent sequences using The Basic Local Alignment Search Tool (BLAST) (Altschul et al., 1990). No sequence homologous to this unique promoter sequence #701 was found. The 5'-end partial sequence of the ORF has the greatest homology to *Chlamydomonas reinhardtii* beta tubulin 2 (TUB2) gene (GenBank accession No.: XM_001693945) in a BLAST search.

The identified promoter sequence is 498 nucleotides long and contains a −10 Pribnow-Schaller box (AGGAAGACT) at the position 444, and a −35 box at position 424 (CTGACG), a putative transcription start site at position 459, and a putative transcription factor binding site AAGGTAGA at position 468.

2. Isolation and Identification of a Tubulin Gene Promoter #341.

Oligonucleotide primers #54 (SEQ ID NO: 7) and #55 (SEQ ID NO: 8) were designed based on *Thraustochytrium* sp. ONC-T18 genomic sequence data using the bioinformatics software package Kodon (Applied Maths). Oligonucleotide primers were synthesized and purchased from Invitrogen (California, USA).

The tubulin gene promoter #341, including the downstream partial open reading sequence, was amplified from the genomic DNA of ONC-T18 by PCR using the same conditions as described for the isolation of the tubulin gene promoter #701. The purified DNA fragment amplified was cloned into pT7Blue-3 vector using Perfectly Blunt® Cloning Kits (Novagen, San Diego, Calif.) as per manufacturer's protocol. The plasmid DNA of the positive clone JZ2-17-14 was isolated from *E. coli* cells of 3 mL culture using Zyppy™ Plasmid Miniprep Kit (Zymo Research Corp., Orange, Calif.).

The insert of the recombinant plasmid DNA was sequenced using the forward primer #62 (SEQ ID NO:3) and the reverse primer #63 (SEQ ID NO:4). The resulting sequences were assembled and analyzed using bioinformatics software package Kodon (Applied Maths) and algorithms BLAST. The insert nucleotide sequence of the clone JZ2-17-14 is 1115 base pairs long (SEQ ID NO:9). A partial ORF of a tubulin gene located at the 3'-end sequence of the insert, has been identified. The upstream sequence of the putative translation start code ATG of the ORF is considered as the putative promoter #341 (SEQ ID NO:10).

A search for sequences homologous to the tubulin gene promoter #341 (SEQ ID NO:10) was performed in various Genbank databases including the database of patent sequences using The Basic Local Alignment Search Tool (BLAST) (Altschul et al., 1990). No sequence homologous to this unique tubulin gene promoter #341 sequence was found. The 5'-end sequence of the putative partial ORF has the greatest homology to *Chlamydomonas reinhardtii* alpha tubulin 2 (TUA2) gene (GenBank accession No.: 5728641) in a BLAST search.

This 1104 nucleotide long promoter sequence contains a −10 box (CGCTAAAAT) at position 542, and −35 box (TTCACG) at position 518, the putative transcription start site at position 557 and the putative transcription factor binding site GCTAAAAT at position 543 as well as a −10 box (TAGTAGATT) at position 143, and −35 box (TTGCTC) at position 125, the putative transcription start site at position 158 and the putative transcription factor binding sites ATTTTGTA at position 149 and TTTTGTAA at position 150.

3. Isolation and Identification of a Tubulin Gene Terminator #347.

Oligonucleotide primers #58 (SEQ ID NO: 11) and #59 (SEQ ID NO: 12) were designed based on genomic sequence data of ONC-T18 using bioinformatics software package Kodon (Applied Maths). The oligonucleotide primers were synthesized and purchased from the company Invitrogen (California, USA).

The tubulin gene terminator #347 was amplified from genomic DNA of ONC-T18 with PCR using the same conditions as described for the isolation of the tubulin gene promoter #341. The purified DNA fragment was cloned into pT7Blue-3 vector using Perfectly Blunt® Cloning Kits (Novagen, San Diego, Calif.) as per manufacturer's protocol. The plasmid DNA of the positive clone JZ2-17-22 was isolated from the bacterial *E. coli* cells of 3 mL culture using the Zyppy™ Plasmid Miniprep Kit (ZYMO RESEARCH CORP., Orange, Calif.).

The insert of the recombinant plasmid DNA was sequenced using the forward primer #62 (SEQ ID NO:3) and the reverse primer #63 (SEQ ID NO:4). The resulting sequences were assembled and analyzed using bioinformatics software package Kodon (Applied Maths) and algorithms BLAST. The insert of the nucleotide sequence of the clone JZ2-17-22 is 727 base pairs long (SEQ ID NO:13). The 5'-end sequence of the insert has been identified as a putative partial ORF that contains a putative gene translational stop codon TAA. The downstream sequence of the stop codon TAA is considered as the putative tubulin gene terminator #347 (SEQ ID NO:14).

A search for sequences homologous to the tubulin gene terminator #347 sequence (SEQ ID NO:14) was performed in various databases of the Genbank including the database of the patent sequences using The Basic Local Alignment Search Tool (BLAST) (Altschul et al., 1990). No homologous sequence of this unique tubulin gene terminator #347 sequence was found. The partial sequence of the putative ORF has the greatest homologue to *Ceratopteris richardii* alpha tubulin gene (GenBank accession No.: XM_001691824) in a BLAST search.

The 590 nucleotide long terminator sequence contains a putative polyadenalytion signal sequence AAAACAAAAA (SEQ ID NO:69) functioning for the termination of transcription by RNA polymerase.

4. Isolation and Identification of a Tubulin Gene Terminator #713.

Oligonucleotide primers #60 (SEQ ID NO: 15) and #61 (SEQ ID NO: 16) were designed based on genomic sequence data of ONC-T18 using bioinformatics software package Kodon (Applied Maths). The oligonucleotide primers were synthesized and purchased from Invitrogen (California, USA).

The tubulin gene terminator #713 was amplified from the genomic DNA of ONC-T18 with PCR using the same conditions as described for the isolation of the tubulin gene promoter #341. The purified DNA fragment was cloned into pT7Blue-3 vector using Perfectly Blunt® Cloning Kits (Novagen, San Diego, Calif.) as per manufacturer's protocol. The plasmid DNA of the positive clone JZ2-22-9 was isolated from the bacterial *E. coli* cells of 3 mL culture using Zyppy™ Plasmid Miniprep Kit (Zymo Research Corp., Orange, Calif.).

The insert of the recombinant plasmid DNA was sequenced using the forward primer #62 (SEQ ID NO:3) and the reverse primer #63 (SEQ ID NO:4). The resulting sequences were assembled and analyzed using bioinformatics software package Kodon (Applied Maths) and algorithms BLAST. The insert of the nucleotide sequence of the clone JZ2-22-9 is 869 base pairs long (SEQ ID NO:17). The 5'-end sequence of the insert has been identified as a putative partial ORF that contains a putative gene translational stop codon TAA. The downstream sequence of the stop codon TAA is considered as the putative tubulin gene terminator #347 (SEQ ID NO:18).

A search for a sequence homologous to the tubulin gene terminator #713 sequence (SEQ ID NO:18) was performed in various databases of the Genbank including the database of the patent sequences using The Basic Local Alignment Search Tool (BLAST) (Altschul et al., 1990). No sequence homologous to this unique tubulin gene terminator #713 sequence was found. The partial sequence of the putative ORF has the greatest homology to *Cyanophora paradoxa* beta 1 tubulin (tubB1) gene (GenBank accession No.: AF092952) in a BLAST search.

The 640 nucleotide long terminator sequence (SEQ ID NO:14) contains a putative polyadenalytion signal sequence CATAAA functioning for the termination of transcription by message RNA polymerases.

5. Isolation and Identification of a Δ5 Elongase Gene (PCT/IB2007/004553) Promoter Sequence (SEQ ID NO: 19).

Based on the genomic sequence data of ONC-T18 using bioinformatics software package Kodon (Applied Maths), the oligonucleotide primer #3 (SEQ ID NO: 20) in which a restriction enzyme site XbaI was added at its 5'-end for the convenience of downstream molecular cloning, and primer #4 (SEQ ID NO: 21) in which a restriction enzyme site NcoI was added at its 5'-end, were designed. The oligonucleotide primers were synthesized and purchased from Invitrogen (California, USA). The Δ5 elongase gene promoter was amplified from the genomic DNA of ONC-T18 with PCR, precipitated, digested with the restriction enzymes XhoI and NcoI, agarose-gel-purified and cloned into the corresponding restriction sites of the vector pSV40/Zeo2 (Invitrogen Corporation, California). The insert of the positive clone JZ1-57-7 was sequenced using primer #14 (SEQ ID NO:22) and primer #15 (SEQ ID NO:23). The resulting sequences were assembled and analyzed using bioinformatics software package Kodon (Applied Maths) and algorithms BLAST. The insert of the nucleotide sequence of the clone JZ1-57-7 is 950 base pair long (SEQ ID NO: 19) and has been identified as the Δ5 elongase gene promoter (SEQ ID NO:19) of ONC-T18.

This 950 nucleotide long promoter sequence (SEQ ID NO:19) contains a −10 box (TGCCAGACT) at position 113, −35 box (TTTTCT) at position 91, a putative transcription start site at position 128 and putative transcription factor binding sites CTCCTTTT, TTTCTTTT, TTCTTTTT and TTGCTCCT at position 87, 92, 93 and 131 as well as a −10 box (AGTTCTGAT) at position 444, a −35 box (TTTCCG) at position 419, and a putative transcription start site at position 459.

A search for sequences homologous to the Δ5 elongase gene promoter sequence (SEQ ID NO:19) was performed in various databases of the Genbank including the database of the patent sequences using the Basic Local Alignment Search Tool (BLAST) (Altschul et al., 1990). No sequence homologous to the Δ5 elongase gene promoter sequence (SEQ ID NO:19) was found.

6. Isolation and Identification of a Δ4 Desaturase Gene (PCT/1B2007/004553) Promoter Sequence (SEQ ID NO:24).

The oligonucleotide primer #1 (SEQ ID NO: 25) in which an restriction enzyme site XhoI was added at its 5′-end for the convenience of downstream molecular cloning and primer #2 (SEQ ID NO: 26) in which an restriction enzyme site NcoI was added at its 5′-end, were employed for the isolation of the Δ4 desaturase gene promoter sequence (SEQ ID NO:24). The DNA fragment of Δ4 desaturase gene promoter was amplified using PCR, precipitated, digested with the restriction enzymes XhoI and NcoI, agarose-gel-purified and cloned into the corresponding restriction sites of the vector pSV40/Zeo2 (Invitrogen Corporation, California) digested with the same restriction enzymes and gel-purified. The insert of a positive clone JZ1-57-1 was sequenced using the primer #14 (SEQ ID NO:22) and primer #15 (SEQ ID NO:23). The resulting sequences were assembled and analyzed using bioinformatics software package Kodon (Applied Maths) and algorithms BLAST. The insert of the nucleotide sequence of the clone JZ1-57-1 is 1216 base pairs long (SEQ ID NO: 24) and has been identified as the Δ4 desaturase gene promoter (SEQ ID NO:24) of ONC-T18.

This 1216 nucleotide long promoter sequence (SEQ ID NO:24) contains a −10 box (GCGTATTAT) at position 58, −35 box (CTACAG) at position 34, the putative transcription start site at position 73 and a putative transcription factor binding sites TTATATTT and TTTTCGCA at positions 63 and 69 as well as a −10 box (CGTCATCCT) at the position 1038, −35 box (TGGACG) at position 1014, and a putative transcription start site at position 1053.

A search for sequences homologous to the Δ4 desaturase gene promoter sequence (SEQ ID NO:24) was performed in various databases of the Genbank including the database of the patent sequences using the Basic Local Alignment Search Tool (BLAST) (Altschul et al., 1990). No sequence homologous to the Δ4 desaturase gene promoter (SEQ ID NO:15) was found.

Example 2

Nucleic Acid Constructs

This example describes the construction of the Thraustochytrid-specific gene expression vectors.

1. Generation of the Recombinant Plasmid Vectors pD4DPZ1 (SEQ ID NO:30; FIG. 2) and pE5PZ1 (SEQ ID NO:31; FIG. 3).

Promoter DNA fragments of the Δ4 desaturase and Δ5 elongase genes of ONC-T18 were amplified with PCR using the genomic DNA of ONC-T18 as the template and TaKaRa LA Taq™ DNA polymerase (TAKARA BIO INC., Shiga, Japan). Primer #1 (SEQ ID NO: 25) bearing the restriction enzyme site XhoI at its 5′-end, and primer #2 (SEQ ID NO: 26) embracing the restriction enzyme site NcoI at its 5′-end were utilized for the amplification of the Δ4 desaturase gene promoter (SEQ ID NO:24). Primer #3 (SEQ ID NO: 20) bearing the restriction enzyme site XbaI at its 5′-end and primer #4 (SEQ ID NO: 21) containing the restriction enzyme site NcoI at its 5′-end were employed for the amplification of the Δ5 elongase promoter (SEQ ID NO:19). PCR reactions were carried out in a volume of 50 μL reaction mix containing 2.5 units TaKaRa LA Taq™ DNA Polymerase (TAKARA BIO INC., Shiga, Japan), 1×LA PCR Buffer II, dNTP Mixture (0.40 mM each), 225 ηg of the genomic DNA template, 0.20 μM primers [primer pairs, #1 (SEQ ID NO: 25) and #2 (SEQ ID NO: 26) for amplification of the Δ4 desaturase gene promoter, and #3 (SEQ ID NO: 20) and #4 (SEQ ID NO: 21) for amplification of the Δ5 elongase promoter] under the following conditions: 94° C. for 30 seconds for one cycle, 98° C. for 10 seconds and 55° C. for 5 seconds, 72° C. for 2 minutes for 30 cycles.

The PCR products were precipitated following these procedures: added nuclease-free ddH$_2$O to a total volume 200 μL, then added 20 μL 3M NaAc (pH 5.2) and 440 μL 100% ethanol and mixed by briefly vortexing, incubated in ice for 1 hours, centrifuged at full speed with a desktop centrifuge for 10 minutes, discarded the supernatant, added 500 μL 75% ethanol and centrifuged for 2 minutes at full speed, discarded the supernatant and vacuum-dried the DNA pellets for about 10 minutes. The PCR products of the Δ4 desaturase gene promoter were digested with restriction enzymes NcoI (10 units) and XhoI (10 units) in a volume of 25 μL reaction mixture containing 1× NEBuffer 2 and 1×BSA; (New England Biolabs, Ipswich, Mass., USA) at 37° C. for 2 hours. PCR products of the Δ5 elongase gene promoter were digested with restriction enzymes NcoI (10 units) and XbaI (10 units) in the same conditions. The digested PCR products were resolved in 0.8% agarose gel for electrophoresis at 88 voltages for 45 minutes. The DNA bands of the PCR products were cut out with a razor blade from the agarose gel and the DNAs were extracted and purified with QIAquick Gel Extraction Kit (Qiagen, Valencia, Calif.) as per the manufacturer's protocol. The resulting Δ4 desaturase gene promoter DNA fragment with the enzyme-specific sticky ends was ligated into the corresponding restriction sites NcoI and XhoI of the vector pSV40/Zeo2 digested with the same restriction enzymes and agarose-gel-purified, to yield the vector pD4DPZ1 (SEQ ID NO:30; FIG. 2). The resulting Δ5 elongase gene promoter DNA fragment with the enzyme-specific sticky ends, was ligated into the restriction sites of the vector pSV40/Zeo2 (Invitrogen Corporation, California) digested with NcoI and NheI restriction enzymes and agarose-gel-purified, to yield the vector pE5PZ1 (SEQ ID NO:31; FIG. 3). The ligation reactions were carried out in a volume of 10 μL reaction mix containing 1× ligation buffer, the insert and vector DNAs (3:1 molar ratio) and 0.5 unit T4 DNA ligase (Invitrogen, California) at the ambient temperature for 12 hours. Then the ligated DNAs were transformed into the *E. coli* Top10 competent cells (Invitrogen Corporation, California). The plasmid DNAs of three colonies of the transformants were isolated from 3 mL bacterial cultures using Zyppy™ Plasmid Miniprep Kit (Zymo Research Corp., Orange, Calif.). The integrity of the clones was preliminarily tested with restriction enzyme digestions using enzymes XhoI and NotI for Δ5 elongase gene promoter construct, and enzymes NcoI and XhoI for Δ4 desaturase gene promoter construct. The inserts of the preliminarily identified positive clones JZ1-57-1 of Δ4 desaturase gene promoter vector, and JZ1-57-7 of Δ5 elongase gene promoter vector were thoroughly sequenced using the primer #14 (SEQ ID NO:22) and primer #15 (SEQ ID NO:23). The resulting vector pD4DPZ1 (SEQ ID NO: 30; FIG. 2) contains the ble gene from *Streptoalloteichus hidustanus*, flanked by Δ4 desaturase gene promoter of ONC-T18 and the SV40 terminator. The resulting vector pE5PZ1 (SEQ ID NO:31; FIG. 3) also contains the ble gene flanked by Δ5 elongase gene promoter of ONC-T18 and the SV40 terminator.

The present invention therefore provides, among other things, vectors comprising a *Thraustochytrium* promoter operatively linked to a heterologous gene. In some embodiments, such vectors include, for example, a terminator, one or more replication origins, and one or more detectable or selectable markers.

2. Generation of Green Fluorescent Protein (GFP) Marker Gene Expression Vector (SEQ ID NO:32; FIG. 4).

For preparing the template plasmid DNA of GFP gene, the bacterial stock of *E. coli* containing the plasmid pCD3-327 [GenBank accession No. U70496; (Davis and Vierstra, 1998)] was purchased from the *Arabidopsis* Deposit Center (Ohio, USA). The bacteria were streaked in the LB agar plate containing 100 μg/mL ampicillin. A single colony was inoculated in 3 mL LB medium containing 100 μg/mL ampicillin and grown overnight. The plasmid DNA from the cultured bacteria was isolated using Ultraclean Microbial Miniprep DNA Isolation kit (MO BIO Laboratories, Inc, Solana Beach, Calif.) as per the manufacturer's protocol.

The GFP gene DNA fragment was amplified with PCR using TaKaRa PrimeStar Taq™ DNA Polymerase (TAKARA BIO INC., Shiga, Japan), the template plasmid pCD3-327 DNA and primer pairs #5 (SEQ ID NO:33) bearing the restriction enzyme site XhoI at its 5'-end and #6 (SEQ ID NO:34). Then the PCR products were precipitated with ethanol and digested with restriction enzyme XhoI and gel-purified. The gel-purified DNA was ligated into the restriction enzyme sites XhoI and BsaAI of the backbone of the vector pE5PZ1 plasmid DNA (SEQ ID NO:31; FIG. 3) digested with XhoI and BsaAI enzymes and gel purified, to replace the ble gene with the green fluorescent protein (GFP) marker gene and yield the expression vector pE5PRsGFP1 (SEQ ID NO:32; FIG. 4) in which the GFP gene is flanked by Δ5 elongase gene promoter of ONC-T18 and the SV40 terminator.

The present invention therefore provides, among other things, vectors comprising a *Thraustochytrium* promoter operatively linked to a heterologous gene. In some embodiments, such vectors include, for example, a terminator, one or more replication origins, and one or more detectable or selectable markers. In light of the description provided herein of a plurality of such vectors, and sequence information with regard to certain elements such as promoters and/or terminators sufficient to permit linkage of elements (e.g., promoters, terminators) having such sequences to other elements, those of ordinary skill in the art, reading the present disclosure, would be well enabled to make and use a wide range of different individual vector constructs, for example by combining provided sequences with any of a variety of known other elements, often according to known techniques.

3. Generation of the Recombinant Plasmid Vectors p341PZ40T (SEQ ID NO:35; FIG. 5).

To construct the vector p341PZ40T (SEQ ID NO:35; FIG. 5) which contains the ble gene from *Streptoalloteichus hidustanus*, flanked by the tubulin gene promoter #341 of ONC-T18 and SV40 terminator, the DNA fragment of the tubulin gene promoter #341 was amplified with PCR using the primer pairs #66 (SEQ ID NO:36) and #67 (SEQ ID NO:37), and the template plasmid DNA of the clone JZ2-17-14 described in Example 1. The 5'-end sequence of primer #66 (SEQ ID NO:36) is complementary to a small region of an intermediate vector derived from vector pT7Blue-3 (Novagen, Gibbstown, N.J., USA), and its 3'-end is complementary to the minus-strand of the 5'-end of the tubulin gene promoter #341 of ONC-T18. The 5'-end sequence of primer #67 (SEQ ID NO:37) is complementary to the plus-strand of the 5'-end sequence of the open reading frame of the ble gene and its 3'-end is complementary to the plus-strand of the 3'-end of the tubulin gene promoter #341 of ONC-T18.

The DNA fragment of the ble gene ORF including SV40 terminator located at its 3'-end was also amplified with PCR using the primer pairs #68 (SEQ ID NO:38) and #71 (SEQ ID NO:39), and the plasmid template DNA of the vector pSV40/Zeo2 (Invitrogen, California). The 5'-end sequence of primer #68 (SEQ ID NO:38) is complementary to the minus-strand of the 3'-end sequence of the tubulin gene promoter #341 of ONC-T18 and its 3'-end sequence is complementary to the minus-strand of the 5'-end of the ble gene ORF. The 5'-end sequence of primer #71 (SEQ ID NO:39) is complementary to a small region of an intermediate vector derived from vector pT7Blue-3 and its 3'-end sequence is complementary to the plus-strand of the 3'-end sequence of SV40 terminator.

The PCR reactions were carried out in a volume of 50 μL reaction mix containing 2.5 units TaKaRa PrimeStar Taq™ DNA Polymerase (Takara Bio Inc., Shiga, Japan), 1× PrimerStar PCR Buffer, dNTP Mixture (0.40 mM each), 1 ηg of the template plasmid DNA, 0.20 μM of each primer of the primer pairs. The PCR conditions, 98° C. for 10 seconds and 55° C. for 5 seconds and 72° C. for 2 minutes, for 30 cycles, were employed. The PCR products of the tubulin gene promoter #341 and ble gene ORF were resolved in 0.8% agarose gel for electrophoresis at 65 voltages for 60 minutes. The bands with the right sizes were cut out with a razor blade and their DNAs were extracted and purified with QIAquick Gel Extraction Kit (Qiagen, Valencia, Calif.) as per manufacturer's protocol. Then the gel-purified PCR products were mixed in similar molar ratios, which were used as the DNA templates for the extension PCR to fuse the tubulin gene promoter #341, the ble gene ORF including SV40 terminator together (Higuchi, Krummel, and Saiki, 1988; Zhang, Wege, and Jeske, 2001). The extension PCR was carried out in a volume of 50 μL reaction mix using TaKaRa PrimeStar Taq™ DNA Polymerase (Takara Bio Inc., Shiga, Japan), ~100 ng of the template DNA of the mixed PCR products, and the primer pairs #66 (SEQ ID NO:36) and #71 (SEQ ID NO:39) (0.20 μM each). The PCR conditions, 98° C. for 10 seconds, 50° C. for 5 minutes and 72° C. for 3 minutes for 6 cycles; and 98° C. for 10 seconds, 50° C. for 5 seconds and 72° C. for 3 and a half minutes for 25 cycles, were employed. The PCR product containing ONC-T18-specific ble gene expression cassette was gel purified with QIAquick Gel Extraction Kit (Qiagen, Valencia, Calif.) as per manufacturer's protocol, and cloned into an intermediate vector derived from vector pT7Blue-3 (Novagen, Gibbstown, N.J., USA) using extension PCR (Higuchi, Krummel, and Saiki, 1988; Zhang, Wege, and Jeske, 2001). The extension PCR was carried out in a volume of 50 μL PCR reaction mix containing 2.5 units TaKaRa PrimeStar Taq™ DNA Polymerase (Takara Bio Inc., Shiga, Japan), 1× PrimerStar PCR Buffer, dNTP Mixture (0.40 mM each), 200 ng DNA of the gel purified PCR product containing the ONC-T18-specific ble gene expression cassette and 600 ng plasmid DNA of an intermediate vector linearized with the restriction enzyme HindIII. The PCR conditions, 98° C. for 10 seconds, 60° C. for 5 seconds and 72° C. for 5 and a half minutes for 30 cycles, were employed. Afterward the template plasmid DNA was destroyed by the restriction enzyme digestion of DpnI which specifically digested the methylated plasmid DNA isolated from some bacterial strains. This digestion was carried out in a reaction volume of 150 µL containing 50 µL extension PCR products, 30 unit DpnI and 1× restriction enzyme reaction buffer 4 (New England Biolabs, Ipswich, Mass., USA) at 37° C. for 2 hours. After digestion, the DpnI enzyme was inactivated by incubation at 80° C. for 20 minutes. Then added sterilized water in the digestion mixture up to 350 µL and further desalted and concentrated the DNA to ~100 ng/µL using the column Microcon (YM-100, Millipore Corporate, Billerica, Mass.). One µL of the desalted DNA was used to transform the Top10 E. coli competent cells (Invitrogen, California, USA) using the electroporator (Eppendorf 5210) set up at 1890 voltages as well as the electroporation cuvettes of 1 mm gap (Eppendorf, N.Y., USA). Positive colonies were preliminarily screened with the direct colony PCR as described in Example 1 using the primer pairs #64 (SEQ ID NO:40) and #65 (SEQ ID NO:41). The insert of the positive clone JZ2-53-10 was completely sequenced using forward and reverse primers as well as internal primers #15 (SEQ ID NO:23), #16 (SEQ ID NO:42), #54 (SEQ ID NO: 7), #64 (SEQ ID NO:40), #65 (SEQ ID NO:41) and #85 (SEQ ID NO:43). The resulting sequences were assembled and analyzed using bioinformatics software package Kodon (Applied Maths) and the integrity of the cloned insert was confirmed. The resulting ble gene expression vector was named p341PZST (SEQ ID NO:35; FIG. 5), in which the ble gene is flanked by the tubulin gene promoter #341 of ONC-T18 and SV40 terminator.

The present invention therefore provides, among other things, vectors comprising a *Thraustochytrium* promoter operatively linked to a heterologous gene. In some embodiments, such vectors include, for example, a terminator, one or more replication origins, and one or more detectable or selectable markers. In light of the description provided herein of a plurality of such vectors, and sequence information with regard to certain elements such as promoters and/or terminators sufficient to permit linkage of elements (e.g., promoters, terminators) having such sequences to other elements, those of ordinary skill in the art, reading the present disclosure, would be well enabled to make and use a wide range of different individual vector constructs, for example by combining provided sequences with any of a variety of known other elements, often according to known techniques.

4. Generation of the Recombinant Plasmid Vectors p341PZ347T (SEQ ID NO:44; FIG. 6).

To construct the vector p341PZ347T (SEQ ID NO:44; FIG. 6) which contains the ble gene from *Streptoalloteichus hidustanus*, flanked by the tubulin gene promoter #341 and a tubulin gene terminator #347 of ONC-T18, the DNA fragment of the tubulin gene promoter #341 was amplified with PCR using the primer pairs #66 (SEQ ID NO:36) and #67 (SEQ ID NO:37), and the template plasmid DNA of the clone JZ2-17-14 described in Example 1.

The DNA fragment of the ble gene ORF was also amplified with PCR using primer pairs #68 (SEQ ID NO:38) and #72 (SEQ ID NO:45), and the plasmid template DNA of vector pSV40/Zeo2 (Invitrogen, California). The 5'-end sequence of primer #72 (SEQ ID NO:45) is complementary to the plus-strand of the 5'-end sequence of the tubulin gene terminator #347.

The DNA fragment of the tubulin gene terminator #347 was amplified with PCR using primer pairs #73 (SEQ ID NO:46) and #74 (SEQ ID NO:47), and the template plasmid DNA of clone JZ2-17-22, described in Example 1. The 5'-end sequence of the primer #73 (SEQ ID NO:46) is complementary to the minus-strand of the 3'-end sequence of the open reading frame of the ble gene and its 3'-end is complementary to the minus-strand of the 5'-end of the tubulin gene terminator #347 of ONC-T18. The 5'-end sequence of the primer #74 (SEQ ID NO:47) is complementary to a small region of an intermediate vector derived from the vector pT7Blue-3 and its 3'-end is complementary to the plus-strand of the 3'-end of the *Thraustochytrium* sp. tubulin gene terminator #347.

The PCRs were carried out exactly as described in Example 2, section 3. The PCR products were gel purified with QIAquick Gel Extraction Kit (Qiagen, Valencia, Calif.) as per manufacturer's protocol. The gel-purified PCR products of the tubulin gene promoter #341, ble gene ORF and tubulin gene terminator #347, were mixed in similar molar ratios, which were used as DNA templates for the extension PCR to fuse the tubulin gene promoter #341, the ble gene ORF and the tubulin gene terminator #347 together. The extension PCR was carried out using primer pairs #66 (SEQ ID NO: 36) and #74 (SEQ ID NO: 47), 0.20 µM each, as described in Example 2, section 3. The fusion PCR product was gel purified with the QIAquick Gel Extraction Kit (Qiagen, Valencia, Calif.) as per manufacturer's protocol, and cloned into an intermediate vector derived from vector pT7blue-3 using extension PCR as described in Example 2, section 3. The extension PCR products were transformed into Top10 E. coli competent cells (Invitrogen, California, USA) with electroporation. The positive colonies were initially screened with colony PCR method using primer pairs #64 (SEQ ID NO: 40) and #65 (SEQ ID NO:41), primer pairs #16 (SEQ ID NO:42) and #59 (SEQ ID NO:12), and primer pairs #54 (SEQ ID NO:7) and #15 (SEQ ID NO:23). The insert of the positive clone JZ2-69-2a was completely sequenced using forward and reverse primers as well as internal primers #15 (SEQ ID NO:23), #16 (SEQ ID NO:42), #54 (SEQ ID NO: 7), #59 (SEQ ID NO:12), #63 (SEQ ID NO:4), #64 (SEQ ID NO:40), #65 (SEQ ID NO:41), and #85 (SEQ ID NO: 43). The resulting sequences were assembled and analyzed using bioinformatics software package Kodon (Applied Maths) and the integrity of the cloned insert was confirmed. The resulting ble gene expression vector was named to p341PZ347T (SEQ ID NO:44; FIG. 6) in which the ble gene is flanked by the tubulin gene promoter #341 of ONC-T18 and terminator #347.

The present invention therefore provides, among other things, vectors comprising *Thraustochytrium* promoters and terminators operatively linked to a heterologous gene (e.g., so that the promoter is upstream of the gene and the terminator is downstream). In some embodiments, such vectors include, for example, one or more replication origins, and one or more detectable or selectable markers. The present invention therefore provides, among other things, vectors comprising a *Thraustochytrium* promoter operatively linked to a heterologous gene. In some embodiments, such vectors include, for example, a terminator, one or more replication origins, and one or more detectable or selectable markers.

5. Generation of the Recombinant Plasmid Vector p341P713T (SEQ ID NO:48; FIG. 7).

To construct vector p341PZ713T (SEQ ID NO:48; FIG. 7) which contains the ble gene from *S. hidustanus*, flanked by tubulin gene promoter #341 and tubulin gene terminator #713 of ONC-T18, the DNA fragment of tubulin gene promoter #341 was amplified with PCR using primer pair #66 (SEQ ID NO:36) and #67 (SEQ ID NO:37), and the template plasmid DNA of the clone JZ2-17-14 described in Example 1.

The DNA fragment of the ble gene ORF was amplified with PCR using primer pair #68 (SEQ ID NO:38) and #75 (SEQ ID NO:49), and the plasmid template DNA of the vector pSV40/Zeo2 (Invitrogen, California). The 5'-end sequence of the primer #75 (SEQ ID NO:49) is complementary to the plus-strand of the 5'-end sequence of the tubulin gene terminator #713.

The DNA fragment of tubulin gene terminator #713 was amplified with PCR using the primer pair #76 (SEQ ID NO:50) and #77 (SEQ ID NO:51), and the template plasmid DNA of the clone JZ2-22-9 described in Example 1. The 5'-end sequence of the primer #76 (SEQ ID NO:50) is complementary to the minus-strand of the 3'-end sequence of the ble gene ORF and its 3'-end complementary to the minus-strand of the 5'-end of tubulin gene terminator #713 ONC-T18. The 5'-end sequence of the primer #77 (SEQ ID NO:51) is complementary to a small region of an intermediate vector derived from vector pT7blue-3 and its 3'-end complementary to the plus-strand of the 3'-end of the tubulin gene terminator #713 of ONC-T18.

The PCR products of the tubulin gene promoter #341, ble gene ORF and tubulin gene terminator #713, were gel-purified, mixed in similar molar ratios, and used as the DNA template for extension PCR using the primer pairs #66 (SEQ ID NO:36) and #77 (SEQ ID NO:51) to fuse the tubulin gene promoter #341, the ble gene ORF and tubulin gene terminator #713 together. The fused PCR product was gel purified with QIAquick Gel Extraction Kit (Qiagen, Valencia, Calif.), and cloned into an HindIII-linearized intermediate vector derived from vector pT7blue-3 using a second extension PCR. One microliter (~100 ηg) extension PCR product DNAs were used to transform Top10 E. coli competent cells (Invitrogen, California, USA) with electroporation. Positive colonies were initially screened with colony PCR using primer pair #64 (SEQ ID NO:40) and #65 (SEQ ID NO.41), primer pair #16 (SEQ ID NO:42) and #77 (SEQ ID NO:51), and primer pair #54 (SEQ ID NO:7) and #15 (SEQ ID NO:23). The insert of the positive clone JZ2-69-2b was completely sequenced using forward and reverse primers as well as internal primers #15 (SEQ ID NO:23), #16 (SEQ ID NO:42), #54 (SEQ ID NO: 7), #63 (SEQ ID NO:4), #64 (SEQ ID NO:40), #65 (SEQ ID NO:41), and #85 (SEQ ID NO:43). The resulting sequences were assembled and analyzed using bioinformatics software package Kodon (Applied Maths), and the integrity of the cloned insert was confirmed. Resulting ble gene expression vector was named to p341PZ713T (SEQ ID NO: 48; FIG. 7), in which the ble gene is flanked by the tubulin gene promoter #341 and terminator #713 of ONC-T18.

The present invention therefore provides, among other things, vectors comprising *Thraustochytrium* promoters and terminators operatively linked to a heterologous gene (e.g., so that the promoter is upstream of the gene and the terminator is downstream). In some embodiments, such vectors include, for example, one or more replication origins, and one or more detectable or selectable markers. The present invention therefore provides, among other things, vectors comprising a *Thraustochytrium* promoter operatively linked to a heterologous gene. In some embodiments, such vectors include, for example, a terminator, one or more replication origins, and one or more detectable or selectable markers. In light of the description provided herein of a plurality of such vectors, and sequence information with regard to certain elements such as promoters and/or terminators sufficient to permit linkage of elements (e.g., promoters, terminators) having such sequences to other elements, those of ordinary skill in the art, reading the present disclosure, would be well enabled to make and use a wide range of different individual vector constructs, for example by combining provided sequences with any of a variety of known other elements, often according to known techniques.

6. Generation of the Recombinant Plasmid Vector p701PZ40T (SEQ ID NO:52; FIG. 8).

To construct the vector p701PZ40T (SEQ ID NO:52; FIG. 8) which contains the ble gene from *S. hidustanus*, flanked by the tubulin gene promoter #701 of ONC-T18 and SV40 terminator, the DNA fragment of tubulin gene promoter #701 was amplified with PCR using the primer pair #87 (SEQ ID NO:53) and #88 (SEQ ID NO:54), and the template plasmid DNA of the clone JZ2-17-10 described in Example 1. The 5'-end sequence of primer #87 (SEQ ID NO: 48) is complementary to a small region of vector p341PZ40T and its 3'-end complements to the minus-strand of the 5'-end sequence of the tubulin gene promoter #701. The 5'-end sequence of primer #88 (SEQ ID NO: 54), is complementary to the plus-strand of the 5'-end sequence of the ble gene ORF and its 3'-end matches the plus-strand of the 3'-end of the tubulin gene terminator #701. The PCR product was gel purified and cloned into the vector of p341PZ40T to replace the tubulin gene promoter #341 using extension PCR (Higuchi et al., 1988; Zhang et al., 2001). TaKaRa PrimeStar Taq™ DNA polymerase, 200 ηg DNA of the gel purified PCR products and 600 ng BglII-linearized plasmid DNA of vector p341PZ40T, were used in the extension PCR. One microliter (~100 ηg) extension PCR product DNAs were used to transform Top10 E. coli competent cells (Invitrogen, California, USA) with electroporation. Positive colonies were initially screened with colony PCR method using primer pair #52 (SEQ ID NO: 51) and #53 (SEQ ID NO: 52). The insert of the positive clone was completely sequenced using forward and reverse primers as well as internal primers #52 (SEQ ID NO: 1) and #53 (SEQ ID NO: 2), #15 (SEQ ID NO:23), #16 (SEQ ID NO:42), #63 (SEQ ID NO:4), #64 (SEQ ID NO:40), #65 (SEQ ID NO:41), and #85 (SEQ ID NO:43). Resulting sequences were assembled and analyzed using bioinformatics software package Kodon (Applied Maths) and the integrity of the cloned insert was confirmed. The resulting ble gene expression vector was named to p701PZ40T (SEQ ID NO:52; FIG. 7), in which the ble gene is flanked by the tubulin gene promoter #701 of ONC-T18 and SV40 terminator.

7. Generation of the recombinant plasmid vector p341PRsGP40T (SEQ ID NO:55; FIG. 9).

To construct the vector p341PRsGFP40T (SEQ ID NO:55; FIG. 9) which contains the GFP gene from *Aequorea victoria*, flanked by the tubulin gene promoter #341 of ONC-T18 and SV40 terminator, the DNA fragment of the tubulin gene promoter #341 was amplified with PCR using primer pair #66 (SEQ ID NO:36) and #78 (SEQ ID NO:56), and the template plasmid DNA of the clone JZ2-17-14 described in Example 1. The 5'-end sequence of primer #78 (SEQ ID NO:56) is complementary to the plus-strand of the 5'-end sequence of the GFP gene ORF and its 3'-end matches the plus-strand of the 3'-end of the tubulin gene promoter #341 of ONC-T18.

The DNA fragment of the GFP gene ORF was also amplified with PCR using primer pair #79 (SEQ ID NO: 57) and #80 (SEQ ID NO:58), and the template plasmid DNA of vector pCD3-327. The 5'-end sequence of the primer #79 (SEQ ID NO:57) is complementary to the plus-strand of the 3'-end sequence of the tubulin gene promoter #341 of ONC-T18 and its 3'-end sequence matches the minus-strand of the 5'-end of the GFP gene ORF. The 5'-end sequence of the primer #80 (SEQ ID NO: 58) is complementary to the plus-strand of the 5'-end sequence of the SV40 terminator, and its 3'-end matches the plus-strand of the 3'-end sequence of the GFP gene ORF.

The DNA fragment of the SV40 terminator was also amplified with PCR using primer pair #81 (SEQ ID NO:59) and #71 (SEQ ID NO:39), and the template plasmid DNA of vector pSV40/Zeo2 (Invitrogen, California). The 5'-end sequence of the primer #81 (SEQ ID NO:59) is complementary to the minus-strand of the 3'-end sequence of the GFP gene ORF, and its 3'-end sequence matches the 5'-end of SV40 terminator.

The above three PCR products were gel purified, mixed in similar molar ratios, and used as the DNA template for the extension PCR using primer pair #66 (SEQ ID NO:36) and #71 (SEQ ID NO:39) to fuse the tubulin gene promoter #341, GFP gene ORF and SV40 terminator together (Higuchi, Krummel, and Saiki, 1988). The extension PCR product containing the ONC-T18-specific GFP gene expression cassette was gel purified, and cloned into vector p341PZ40T linearized with restriction enzyme HindIII in a second round extension PCR. The second round PCR products were cleaned, desalted, and transformed into Top10 E. coli competent cells with electroporation. The positive colonies were screened using direct colony PCR and the primer pair #54 (SEQ ID NO:7) and #86 (SEQ ID NO:60). The insert of the positive clone JZ2-53-20 was completely sequenced using forward and reverse primers as well as internal primers #15 (SEQ ID NO:23), #16 (SEQ ID NO:42), #54 (SEQ ID NO:7), #63 (SEQ ID NO:4), #64 (SEQ ID NO:40), #65 (SEQ ID NO:41), #85 (SEQ ID NO:43), and #86 (SEQ ID NO:60). The resulting sequences were assembled and analyzed using bioinformatics software package Kodon (Applied Maths) and the integrity of the cloned insert was confirmed. The resulting GFP gene expression vector was named to p341PRsGFP40T (SEQ ID NO:55; FIG. 8) in which the GFP gene is flanked by the tubulin gene promoter #341 of ONC-T18 and SV40 terminator.

8. Generation of the Recombinant Plasmid Vector pD4DPZ118S (SEQ ID NO:61; FIG. 10).

To construct pD4DPZ18S (SEQ ID NO:61; FIG. 10) vector, the plasmid DNA of vector pD4DPZ 1 was digested with restriction enzymes SalI and SphI to linearize the vector and then gel purified with QIAquick Gel Extraction Kit (Qiagen, Valencia, Calif.) as per manufacturer's protocol. The 18S rDNA fragment (SEQ ID NO: 29) that was amplified from the genomic DNA of ONC-T18 with PCR using primer pair 18SrRNAf (SEQ ID NO: 27) and 18SrRNAr (SEQ ID NO: 28) and cloned into vector pT7Blue-3, was released from the plasmid DNA of the clone JZ2-3-1 by restriction digestion with enzymes XhoI and SphI, then gel purified and ligated into the restriction sites SalI and SphI of the linearized vector of pD4DPZ1, to yield the pD4DPZ18S (SEQ ID NO: 61; FIG. 10) which bears a DNA fragment of the 18S ribosome RNA gene.

9. Generation of the Recombinant Plasmid Vector p341PZ5pEx (SEQ ID NO:62; FIG. 11).

To construct p341PZ5pEx for the over-expression of homologous and heterogonous genes, for knocking down or knocking out the homologous gene in the Thraustochytrid protist microbes, the zeocin resistance gene expression vector pd5EPPZ1 was modified with PCR using primers LinkerF (SEQ ID NO:63) and LinkerR (SEQ ID NO:64) to replace the zeocin resistance gene ORF with multiple cloning sites including enodonuclease restriction sites (NcoI, SpeI, KpnI, MluI, NdeI, SphI, NruI, BstBI and BamHI). After PCR, the template plasmid DNA was destroyed using the enodonuclease restriction enzyme DpnI. The PCR product was precipitated and digested with enodonuclease restriction enzyme MluI, gel-purified, re-ligated together with T4 DNA ligase (Invitrogen, California) and then transformed into Top10 E. coli cells. The preliminary screening of the positive clones was carried out using restriction digestions. The integrity of positive clones was confirmed with DNA sequencing and named as the plasmid p5eEP40T (SEQ ID NO: 65). The plasmid DNA of the positive clone was digested with the enodonuclease restriction enzymes HindIII and EcoRI and the backbone plasmid DNA was gel purified. The zeocin resistance gene expression cassette in which the zeocin gene ORF is flanked by the tubulin gene promoter #341P and SV40 terminator, was also isolated and gel-purified from vector p18S341PZ40t digested with the same enodonuclease restriction enzymes HindIII and EcoRI. The zeocin resistance gene expression cassette was then ligated into the corresponding enodonuclease restriction sites HindIII and EcoRI of the plasmid p5eEP40T, resulting in the gene expression vector p341PZ5pEx.

Example 3

Identification of an Antibiotic that can be Used for Genetic Manipulation of *Thraustochytrium* sp. ONC-T18

The present Example describes experiments identifying an antibiotic for which resistance can be used as a selectable marker for genetic manipulation of ONC-T18.

*Thraustochytrium* sp. ONC-T18 was grown on agar plates (20 g agar per liter ONC-T18-GM0). One loop of inoculum of ONC-T18 was inoculated into 50 mL of liquid ONC-T18-GM0, and the culture was incubated in a shaker incubator at 25° C. at 250 rpm for 36 hours. Half a milliliter of the culture was transferred into a 1.5 mL tube and vortexed at full speed for 30 seconds to break down cell clusters, then diluted in 50 mL sterilized water. One hundred microliters of the resulting solution was spread onto each ONC-T18-GM0 medium plate. Each plate contained one of various antibiotics at one of various concentrations. Plates were incubated at 25° C. and emergence and development of colonies were observed daily. As can be seen in Table 1, growth of ONC-T18 was insensitive to most of the antibiotics tested. However, zeocin significantly inhibited the growth of ONC-T18 in ONC-T18-GM0 agar plates.

Thus, the present Example identifies zeocin as an antibiotic that can be used for selection in genetic manipulation experiments.

TABLE 1

Effects of different antibiotics on the growth of *Thraustochytrium* sp. ONC-T18

| Antibiotics | Concentration (µg/mL medium) | | | | |
| --- | --- | --- | --- | --- | --- |
| | 0 | 1 | 10 | 50 | 100 |
| Nourseothricin | ++++ | ++++ | ++++ | ++++ | ++++ |
| Bialophos | ++++ | ++++ | ++++ | ++++ | ++++ |

| | Concentration (µg/mL medium) | | | |
| --- | --- | --- | --- | --- |
| | 0 | 100 | 200 | 500 |
| Kanamycin | ++++ | ++++ | ++++ | ++++ |

| | Concentration (µg/mL medium) | | | | |
| --- | --- | --- | --- | --- | --- |
| | 0 | 10 | 30 | 50 | 100 |
| Zeocin | ++++ | +++ | ++ | + | --- |

Example 4

Optimization of Salinity in ONC-T18-GM0 Medium for Effective Selection of *Thraustochytrium* sp. ONC-T18 Transformants As is known in the art, zeocin is unstable at high salt concentrations (Invitrogen, CA, USA). It has also been shown that ONC-T18 prefers to grow under conditions of relatively high salinity because of its natural inhabiting environments (PCT/IB2006/003977). The present Example describes the determination of optimal zeocin concentrations and salinities for efficient selection of ONC-T18 transformants using a zeocin resistance gene as the selectable marker.

One hundred µL of ONC-T18 cell suspension diluted at 1:500 from a 2-day culture were spread onto ONC-T18-GM0 plates containing various concentrations of antibiotic zeocin and sea salt. Inoculated plates were incubated in a 25° C. incubator for 10 days. The numbers of the colonies on each plate were counted. Means of colony numbers from two duplicate plates are presented in Table 2. After 10 days post-inoculation, no colonies were observed in ONC-T18-GM0 agar plates containing 5 g/L sea salt and various concentrations of zeocin. In plates containing 8.5 g/L sea salt without zeocin, only one colony was observed. In plates containing 18 g/L sea salt without zeocin, colony numbers were similar to that of plates containing 35 g/L sea salt without zeocin. However, zeocin at a concentration of 30 µg/mL completely inhibited growth of ONC-T18 in ONC-T18-GM0 agar plates containing 18 g/L sea salt, whereas 100 µg/mL zeocin was needed for complete inhibition of ONC-T18 in ONC-T18-GM0 agar plates containing 35 g/L sea salt. The diameters of single colonies in two duplicate plates were measured and their means are shown in Table 3. Salinities between 18 g/L and 35 g/L did not affect the sizes of the colonies significantly (FIG. 12). The present Example therefore demonstrates, among other things, that better growth is observed in the presence of sea salt at a concentration above about 8.5 g/L. According to the present invention, concentrations in the range of 8.5 g/L to more than 35 g/L (e.g., to about 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L or more, even possibly as much as 55 g/L, 60 g/L, 65 g/L, 70 g/L, 75 g/L, 80 g/L, 85 g/L, 90 g/L, 95 g/L, 100 g/L or more may be suitable for growth. For selection of transformants using zeocin, of course, it is desirable to achieve robust growth with maintained sensitivity to zeocin. Therefore, for this work, 18 g/L sea salt was used to make ONC-T18-GM0 for selection of ONC-T18 transformants transformed with constructs bearing a zeocin-resistant gene expression cassette.

TABLE 2

Effects of zeocin and salinity on the colony numbers of *Thraustochytrium* sp. ONC-T18

| Salt concentration (g/L) | Zeocin concentration (µg/mL) | | | | |
| --- | --- | --- | --- | --- | --- |
| | 0 | 10 | 30 | 50 | 100 |
| 5 | 0 | 0 | 0 | 0 | 0 |
| 8.5 | 1 | 0 | 0 | 0 | 0 |
| 18 | 33 | 11 | 0 | 0 | 0 |
| 35 | 39 | 22.5 | 11 | 5 | 0 |

TABLE 3

Effects of zeocin and salinity on the colony growth rates (diameter in mm) of *Thraustochytrium* sp. ONC-T18

| Salt concentration (g/L) | Zeocin concentration (µg/mL) | | | | |
| --- | --- | --- | --- | --- | --- |
| | 0 | 10 | 30 | 50 | 100 |
| 5 | 0 | 0 | 0 | 0 | 0 |
| 8.5 | 3 | 0 | 0 | 0 | 0 |
| 18 | 4.3 | 4.1 | 0 | 0 | 0 |
| 35 | 5.2 | 4.1 | 1.9 | 0.6 | 0 |

Transformation efficiencies were tested at various pressure conditions. In the present Example, it was found that a pressure condition of about 1100 psi resulted in a better transformation efficiency than did other pressure conditions tested.

Example 5

Transformation of *Thraustochytrium* sp. ONC-T18

This Example describes a biolistic transformation method of ONC-T18.

Materials and Methods.

Generating Competent Cells.

ONC-T18 was maintained on ONC-T18-GM0 agar plates in a 25° C. incubator and transferred to fresh plates every 3-4 weeks. One loop of inoculum of ONC-T18, taken from vigorously growing cells, was inoculated in 50 mL ONC-T18-GM0 in a 250 mL Erlenmeyer flask, then cultured in a shaker incubator at 25° C. at 150 rpm for about 46 hours. Half a milliliter of the culture was transferred into a sterilized 1.5 mL centrifuge tube in a laminar flow hood under sterile conditions, then centrifuged in a desktop centrifuge at 3,000 rpm for 1 minute. The supernatant was discarded, the cell pellent was re-suspended in 0.5 mL sterilized water, and 100 µL of the cell suspension was spread onto the central area (approximately 28 cm$^2$) of an ONC-T18-GM0 agar plate. Petri dishes were left opened in a laminar flow hood under sterile conditions for 10 to 15 minutes to let cells settle down and to evaporate liquid water.

Biolistic Transformation.

Plasmids pd5EPZ1, p341PZ40T, p341PZ347T, p341PZ713T, and pD4DPZ18S (constructed as described in Example 2; see also FIGS. 3, 5, 6, 7, and 10) were isolated from bacterial cultures of strains containing the respective plasmids using the ZYPPY™ Plasmid Maxiprep Kit (Zymo Research Corp., Orange, Calif.) per manufacturer's protocol. As discussed in Example 2, each of these plasmids contains a ble transgene, which confers resistance to zeocin, phleomycin, and bleomycin. (See, e.g., Gatignol et al. (1988) and Dumas et al. (1994), the entire contents of each of which are incorporated by reference herein.) In the present Example, a Sh ble (*Streptoalloteichus hindustanus*) transgene was employed. Other ble transgenes are also suitable, such as the Tn5 ble and Sa ble (*Staphylococcus aureus*) transgenes.

For each plasmid, five µL (~1 µg/µL) of plasmid DNA was mixed with 25 µL of gold particle suspension (60 mg/mL in 50% glycerol) by vortexing for 3 minutes and incubating on ice for 10 minutes. Ten µL of 0.1 M spermidine and 25 µL of 2.5 M CaCl$_2$ were added into the mixture and immediately vortexed for 4 minutes, then centrifuged for 10 seconds at full speed in a desktop centrifuge. The supernatant was discarded. Plasmid DNA-coated gold particles were washed twice with 70% ethanol and re-suspended in 36 µL 98% ethanol. Six µL of the gold particle suspension was spread on each macrocarrier disc and discs were air-dried (Zhang et al. 2001).

The PSD-1000/He particle delivery system (Bio-Rad Laboratories, Inc., California) was used for delivery of plasmid DNAs bearing zeocin resistant gene expression cassettes into ONC-T18 competent cells under sterilized conditions in a laminar flow hood according to the manufacturer's protocol. Parts of the particle delivery system, including macrocarrier holders, macrocarriers, stopping screens, were autoclaved. The chamber of the particle delivery system was disinfected by wiping with 70% ethanol. After bombardment, petri dishes containing transformed cells were incubated at 25° C. incubator in darkness for 6 hours. Transformed cells were then washed out of the dishes using 1 mL sterilized water, transferred into a 1.5 mL autoclaved micro-centrifuge tube, and centrifuged at 3,000 rpm for 2 minutes. The supernatant was discarded and the pellet was re-suspended in 0.5 mL autoclaved water. One-hundred fifty μL of the cell suspension was spread on agar ONC-T18-GM0 plates containing ~150-200 μg/mL zeocin. After the liquid in the plates had been evaporated, plates were sealed with PARAFILM® M and incubated at 25° C. incubator for 6-10 days. Zeocin-resistant colonies were picked using 10 μL pipette tips and suspended in 50 μL sterilized water in a 200 μL PCR tube. One μL of the cell suspension was spotted onto ONC-T18-GM0 agar plates containing 150-200 μg/mL zeocin. After 3-5 day incubation at 25° C., vigorously growing colonies were chosen for further analysis.

Zeocin-resistant colonies were grown on ONC-T18-GM0 agar plates containing 150-200 μg/mL zeocin 4-6 days after biolistic transformation. Zeocin-resistant strains were generated with various constructs derived from combinations of various promoters and terminators isolated from ONC-T18. The numbers of the transformants generated per transformation using different constructs were variable. (See Table 4.)

TABLE 4

Number of transformants per transformation

| Constructs | Number of transformants/5 μg plasmid DNAs |
|---|---|
| pd5EPZ1 | 11 |
| p341PZ40T | 9 |
| p341PZ347T | 4 |
| p341PZ713T | 7 |
| pD4DPZ18S | 5 |

Example 6

PCR Analysis of Transformants of *Thraustochytrium* sp. ONC-T18

This Example describes confirmation of the presence of transgene in transformed ONC-T18. A PCR assay was used to assess presence of the ble transgene, which is present in each of the plasmid constructs used to transform ONC-T18.

One loop of inoculum of each potentially transformed strain growing on zeocin-ONC-T18-GM0 agar plates was inoculated in 10 mL liquid ONC-T18-GM0 medium in a 50 mL flask and grown in a shaker incubator at 25° C. and at 250 rpm for 2 days. Two-mL cultures were used for isolation of the genomic DNA of each strain using an Ultraclean Microbial Mini-prep DNA Isolation kit (MO BIO Laboratories, Inc, Solana Beach, Calif.) following the manufacturer's protocol. Genomic DNA concentrations were measured using spectrum photometer Spectro 2000RSP (Lebomed, Inc., Culver City, Calif., U.S.A). A half μL of genomic DNA was used for a 20 μL PCR reaction containing the following components: Taq DNA polymerase (Sigma), 1×PRC buffer, 2.5 mM $MgCl_2$, dNTPs mixture (0.20 mM each), 0.25 μM primer #64 (SEQ ID NO:66), and 0.25 μM primer #65 (SEQ ID NO:67) in a 200 μL PCR tube. PCR reactions were carried out using the following thermal cycle program: 94° C. for 3 minutes, 94° C. for 1 minute, 55° C. for 2 minutes, and 72° C. for 2 minutes for 30 cycles. Primer #64 anneals to the 5'-end and primer #65 anneals to the 3'-end of the ble gene of each plasmid used for transforming ONC-T18. A ~350 base pair DNA fragment was amplified from the genomic DNAs of positive transformants and from plasmid DNA of the positive control, but not from genomic DNA of the negative control isolated from the cells of the wild type ONC-T18. These results confirm that most zeocin-resistant strains are true transformants (FIG. 13).

Example 7

Growth Rates of Transformants

This Example describes the dermination of growth rates of transformed single cell-derived strains. Inocula of zeocin-resistant strains that had been transferred three times on zeocin ONC-T18-GM0 agar plates was picked from each colony using a 10 μL pipette tip and re-suspended in 50 μL sterilized water in a 200 μL PCR tube. One μL of the cell suspension was spotted on ONC-T18-GM0 agar plates (15 g/L agar) containing either 18 g/L or 35 g/L sea salt. The diameters of the spotted colonies were measured on day 1, day 3, day 5, day 7, and day 8 post-inoculation.

Most tested strains grew faster than the wild type strain ONC-T18 on ONC-T18-GM0 agar plates, whether they were grown on plates containing 18 g/L or 35 g/L sea salt. Among the tested strains, most grew faster on plates containing 18 g/L than on plates containing 35 g/L sea salt. Some strains that grew fastest on ONC-T18-GM0 agar plates containing 18 g/L sea salt (such as strain 5-3) grew slower than other strains on plates containing 35 g/L sea salt. It appears that most transformed strains prefer to grow on media containing lower salinity, for example 18 g/L sea salt (FIG. 14).

Example 8

Zeocin Sensitivity of Transformed Strains

This Example describes assays of the zeocin sensitivity of single-cell derived transformed strains.

A very small amount of inoculum of zeocin-resistant strains that had been transferred three times via colony passages on zeocin/ONC-T18-GM0 agar plates (as well as their parental strain or the wild type strain) was picked from colonies using a 10 μL pipette tip and re-suspended in 50 μL sterilized water in a 200 μL PCR tube. One μL of the cell suspension was spotted on ONC-T18-GM0 agar plates containing 18 g/L sea salt (15 g/L agar) and zeocin at a concentration ranging from 0 to 5000 μg/mL (Invitrogen, CA, USA). The diameters of the spotted colonies were measured on day 1, day 3, day 5, day 7, and day 8.

All strains tested grew well on ONC-T18-GM0 agar plates in the absence of zeocin, but their growth rates differed. The parental strain (the wild type strain) ONC-T18 only grew on ONC-T18-GM0 agar plates that had 30 μg/mL or less zeocin. For all of the five different plasmid constructs, all transformed strains bearing the zeocin-resistance gene (from *S. hidustanus*) expression cassette grew well on ONC-T18-GM0 agar plates having zeocin at concentrations ranging from 30 to 1000 μg/mL (FIG. 15). However, at a concentration of 5000

μg/mL zeocin, most strains grew remarkably slower than that they did on media with 1000 μg/mL or less zeocin, and some of the strains could not grow at all on 5000 μg/mL zeocin (FIG. 15). Several strains, especially those transformed with a plasmid construct bearing zeocin-resistance gene expression cassette driven by the 45 elongase gene promoter, however grew very well (FIG. 15), demonstrating that the 45 elongase gene promoter is a very strong gene expression promoter.

These results are consistent with DHA being the major energy storage fatty acid in the group of Thraustochytrid microalgae (Jain et al. 2007) and with the 45 elongase elongation step being the rate-limiting step during DHA biosynthesis in DHA omega-3 fatty acid producing microbes (Leonard et al. 2004). Growth rate variability among strains transformed with the same plasmid construct either reflects variability in copy number of the ble transgene or variability in insertion location of the ble transgene in the chromosomes of the host strain ONC-T18.

These results indicate that various promoter and terminator sequences isolated from ONC-T18 can effectively drive transgene expression in PUFA-producing microorganisms. In addition, these results indicate that the ble transgene from *S. hidustanus* is a very effective selection marker gene for industrial strain improvement programs and genetic manipulation of *Thraustochytrium* sp. strains.

Example 9

Comparisons of Biomass Productivities Between Transformed Strains and Wild Type Strain *Thraustochytrium* sp. ONC-T18

The present Example describes comparisons of biomass productivities of transformants to that of the wild type strain *Thraustochytrium* sp., and demonstrates, among other things, that certain transformed strains produce elevated biomass levels (e.g., elevated at least 5%, 10%, 15%, 20%, 25%, or more as compared with wild type).

ONC-T18, 10 mL ONC-T18-GM0 (18 g/L sea salt) cultures were each inoculated with a transformed strain or with the wild type strain ONC-T18. Cultures inoculated with a transformed strain contained 200 μg/mL zeocin in the medium. Cultures were grown at 25° C. in a shaker incubator set at 250 rpm for 3 days until the $OD_{600}$ reached about 1.979~2.369. Then 50 mL ONC-T18-GM0 cultures containing either 18 g/L or 35 g/L sea salt in 250 mL flasks were inoculated with 6 $OD_{600}$ of the inocula of each strain, including the wild type strain ($OD_{600}$ was measured for 1 mL of culture and then the volume of culture was scaled up to correspond to an $OD_{600}$ value of 6; e.g., if the $OD_{600}$ measurement were 2, then (1 mL×(6/2.0))=3 mL was used as inoculate). Cultures were grown in a shaker incubator set at 250 rpm at 25° C. for 2 days. Five mL of autoclaved 50% glucose were then added into each culture flask. Cultures were continually grown in a shaker incubator set at 150 rpm and at 20° C. for another 2 days. Six mL of autoclaved 50% glucose were then added into each culture flask and the cultures were constantly grown in a shaker incubator set at 150 rpm and at 20° C. for 3 more days. The biomasses of cultures of each strain in the two types of ONC-T18-GM0 media (with 18 g/L or with 35 g/L sea salt) were harvested by transferring cell cultures into a 50 mL falcon tube and centrifuging at 4000 rpm using the SORVALL LEGEND RT+ centrifuge (Thermo Fisher Scientific Inc., MA, USA). Biomass floated on the surface of the liquid medium as a compacted layer. Liquid medium was released by punching a very small hole at the bottom of the falcon tube using an 18G 1½ syringe needle. The pellet of the biomass in the tube was frozen in a −80° C. freezer overnight and then freeze-dried using a freeze dryer for three days. The biomass of each sample was weighed. Nine strains including the wild type were tested.

Most transformants produced similar amounts of dry cell biomass to that of the wild type strain ONC-T18 when grown in ONC-T18-GM0 containing 35 g/L artificial sea salt. One out of 8 transformed strains produced about 22% more dry cell biomass than that of the wild type strain ONC-T18 (FIG. 16) when grown under the same conditions. In the ONC-T18-GM0 containing 18 g/L sea salt, 7 out of 8 transformed strains produced similar amounts or more biomass than that of the wild type strain ONC-T18. One out of 8 tested strains produced 19.5% more biomass than that of the wild type strain ONC-T18 (FIG. 16).

Example 10

Comparisons of DHA Productivity Between Transformed Strains and the Wild Type Strain of *Thraustochytrium* sp. ONC-T18

The present Example describes DHA productivity in the various transformed strains, and demonstrates elevated levels as compared to the wild type. The present Example demonstrates, among other things, that levels within the range of at least 1%-36% higher than wild type (e.g., 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, etc) have been achieved. Based on these findings, one of ordinary skill in the art will appreciate that further elevation can be achieved (e.g., to levels within the range of 1%-1000% higher than wild type, e.g., about 1%, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 550%, 600%, 650%, 700%, 750%, 800%, 850%, 900%, 950, 1000% or more higher than wild type). The present Example further demonstrates achievement of DHA:biomass ratios within the range of about 1:4 to about 1:2, at least about 40% higher than those typically observed with wild type strains. (See, e.g., Table 2 in Raghukumar (2008), the entire contents of which are incorporated by reference herein.) Based on these findings, those of ordinary skill in the art would appreciate that at least ratios of about 1:5 can be achieved. We have achieved DHA to biomass ratios (DHA:biomass) of about 1:8 to 1:4; and expect to achieve ratios of about 1:3. Examples in literature (such as the review published by Raghukumar, 2008) indicate achievements that have not reduced this ratio below 1:5.

Cultures of 8 transformed strains and their parental strain (wild type) were grown, and the biomass was harvested and freeze-dried under the same conditions as described in Example 9. Fatty acid methyl ester (FAME) extraction was via the direct transesterification method. Approximately 20 mg of freeze dried cell biomass and 3 mL of transesterification reaction buffer (methanol:hydrochloric acid:chloroform) were mixed by vortexing for 10 seconds and then incubated in a 90° C. water bath for two hours. After completion of transesterification, the samples were removed and cooled down to ambient temperature. One mL of water was added and mixed by vortexing for 10 seconds. FAMEs were then extracted by adding 3×2 mL of a hexane: chloroform (v/v, 4:1) solvent and vortexing for 10 seconds; samples were then allowed to sit until phase separations were completed.

Gas chromatographic (GC) analysis of the FAMEs was carried out using two internal standards (200 µL). One hexacosaenoic acid (C23:0) was added before transesterification and the other one, nonadecaenoic acid (C19:0) was added directly before analysis. Analyses were performed in an Agilent 6890 GC (Agilent Technologies, Palo Alto, Calif., USA) installed with a 30 m×0.32 mm internal diameter (0.25 µm film thickness) OMEGAWAX 320 fused-silica capillary column (Sigma-Aldrich, St. Louis, Mo., USA) and flame ionization detector set at 250° C., split ratio 50:1 to FID detector at 275° C. The injection volume was 1 µL. The carrier gas was $H_2$ with a constant flow of 5.0 mL per minute. Confirmation of FAME identity was carried out using a Trace GC-DSQ mass spectrometer (Thermo Electron, Boston, USA) and comparison of the retention times for laboratory standards.

Figure 17A:
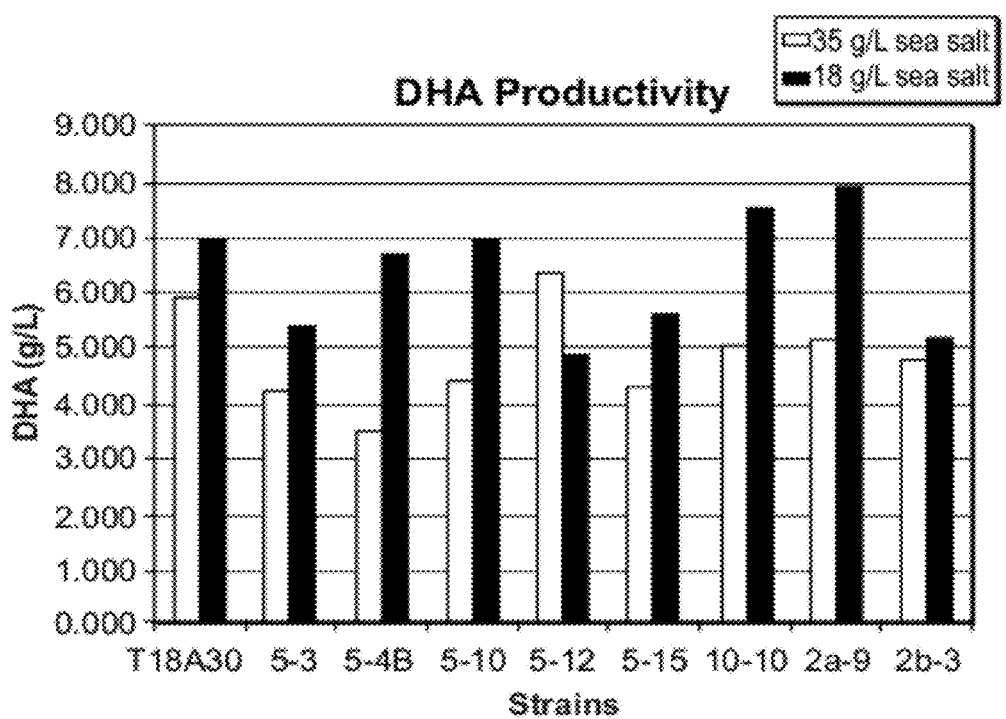

One out of eight transformed strains produced about 6.337 g/L DHA. This yield is about 16% more than that of the wild type strain ONC-T18 when grown in ONC-T18-GM0 containing 35 g/L artificial sea salt. Three out of the eight transformed strains produced more DHA, ranging from 1 to 13% more, than that of the wild type strain ONC-T18 when grown in ONC-T18-GM0 containing 18 g/L artificial sea salt under the same conditions (FIGS. 17A and B).

Figure 17B:
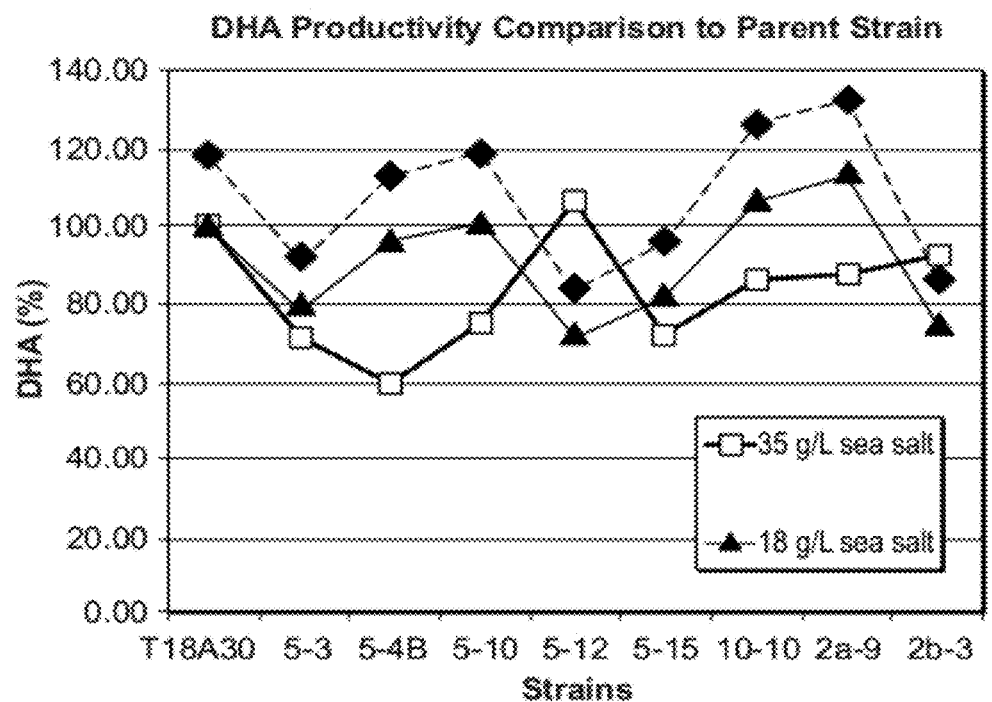

Two out of eight transformed strains produced 7.445 g/L and 7.871 g/L DHA, which represent 25% and 36%, respectively, more than their parental strain (5.935 g/L) grew in ONC-T18-GM0 containing 35 g/L artificial sea salt (FIG. 17B). Use of lower salinity ONC-T18-GM0 not only directly reduces DHA production costs, but also slows down the erosion of the fermentors caused by high concentrations of sodium chloride salt in growth medium for culturing Thraustochytrid microbes.

Figure 17C:
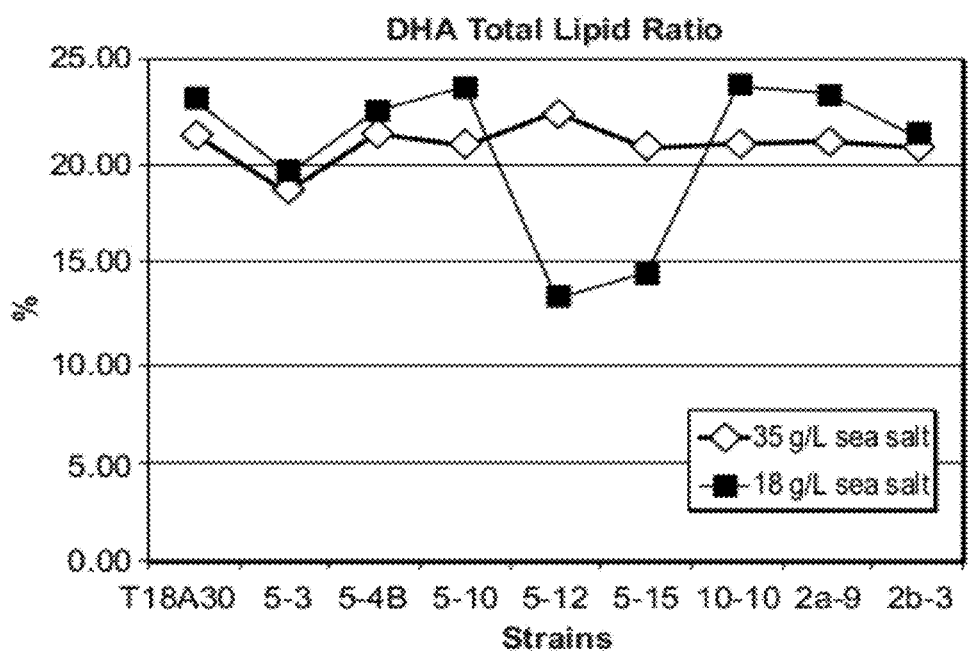
Figure 17D:
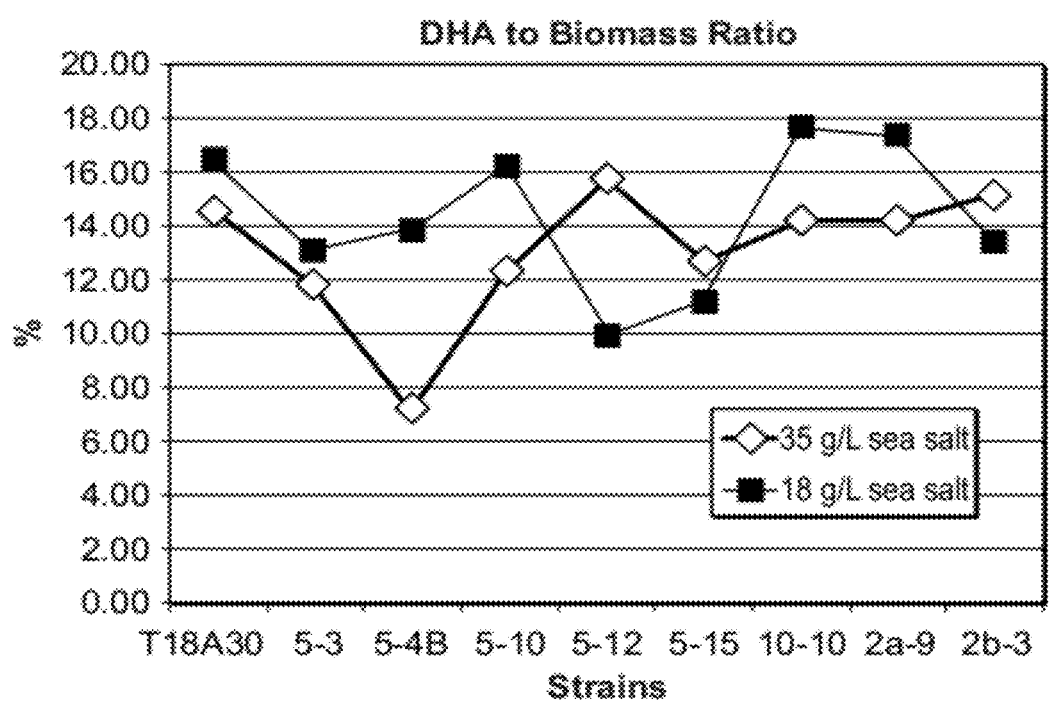

The ratio of DHA to total lipids from high level DHA-producing transformed strains is higher than that of their parental strain (FIG. 17C). The DHA to total lipids factor can influence downstream processing of DHA extracted from the cells of transformed strains. DHA:total lipid ratios achieved with strains and methods of the invention may vary according to fermentation conditions. For example, for cultures grown in flasks, a DHA percentage of about 15% to about 25% of total lipids (corresponding to DHA:total lipids ratios of about 0.15:1 to about 0.25:1) can typically be achieved with transformed strains. For cultures grown in a fermentor, a DHA percentage of about 30% to about 60% of total lipids (corresponding to DHA:total lipids ratios of about 0.3:1 to about 0.6:1) can typically be achieved with transformed strains. Much greater DHA yields are obtained from transformed strains disclosed herein than can be obtained with wild type strains. For example, DHA yields from transformed strains typically range from about 10 to about 40 g/L (grams DHA per liter of media), whereas DHA yields from wild type strains typically range from about 0.5 to about 1.6 g/L. (See, e.g., Table 2 in Raghukumar (2008)). The ratio of DHA to biomass from high level DHA production transformed strains is also higher than that of their parental strain. This higher ratio of DHA to biomass benefits the downstream extraction of DHA from the cell biomass of the transformed strains (FIG. 17D).

All of the cultures in this Example were grown under the same conditions. The higher level of DHA production by the transformed strains indicate that those strains have a higher efficiency of converting carbon sources into DHA, which can reduce the cost of DHA production from those transformed strains.

Example 11

Comparison of Total Lipid Productivity Between Transformed Strains and the Wild Type Strain *Thraustochytrium* sp. ONC-T18

As amply described and demonstrated herein, ONC-T18 has great potential for use as an efficient biofactory not only for PUFA and its derivatives of pharmaceutical and nutraceutical biomolecule productions, but also for biofuel production. In order to assess and characterize the ability of ONC-T18 to be employed for biofuel production in accordance with the present invention, total lipid productivities and fatty acid profiles of transformed strains of ONC-T 18 were analyzed for potential use in methods for changing fatty acid profiles for specialty product applications.

Cultures of 8 transformed strains and their parental strain (wild type) were grown, and the biomass was harvested and freeze-dried under the same conditions as described in Example 9. FAME extraction and GC analysis were carried out as described as in Example 10.

Figure 18A:
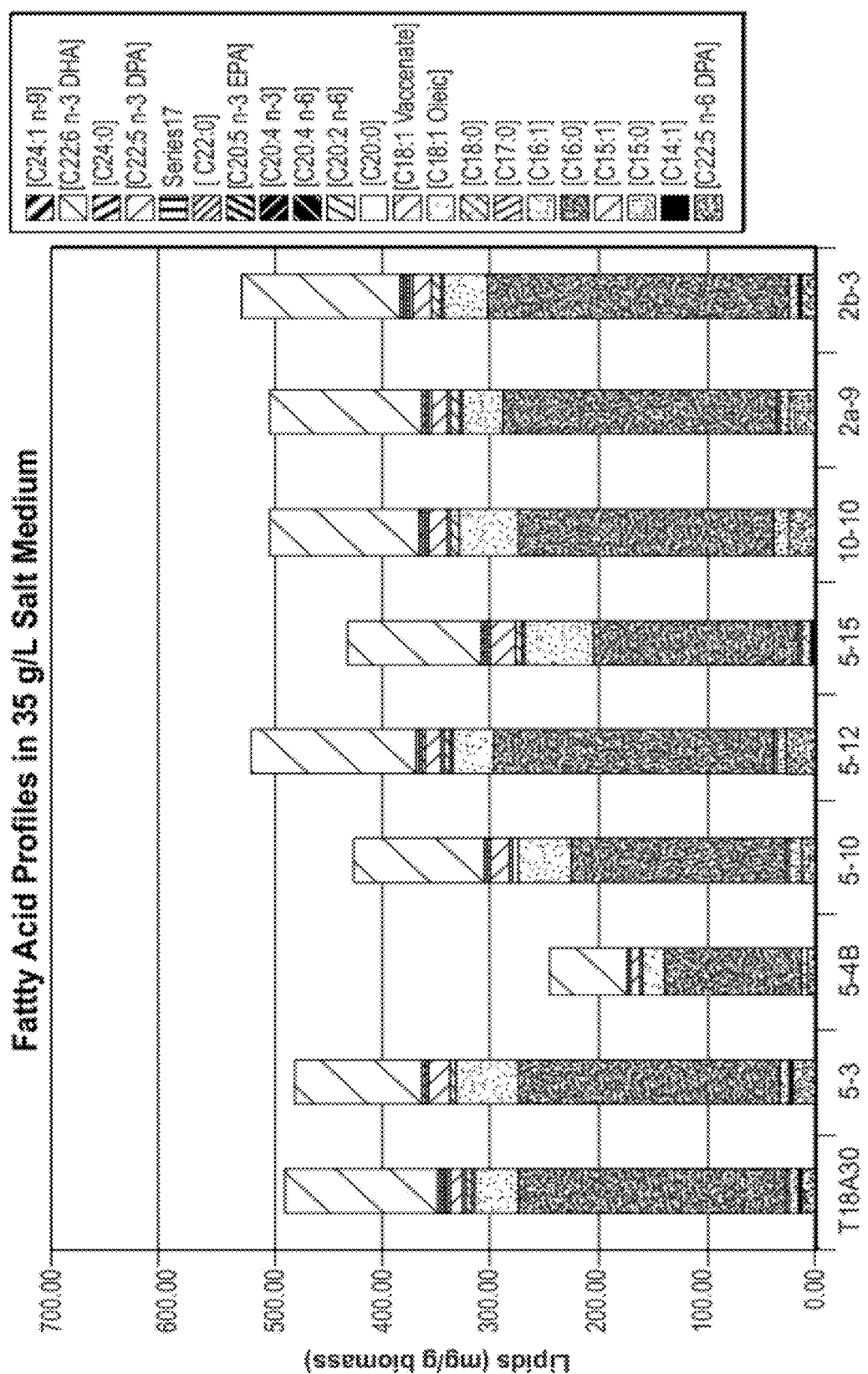

We found that fatty acid profiles of the transformed strains were very similar to that of their parental strain when grown in ONC-T18-GM0 containing 35 g/L artificial sea salt. Four out of eight transformed strains produced more total lipids than that of their parental strain, further demonstrating that the transformation process itself and the presence and/or expression of the transgene did not significantly affect fatty acid profiles, nor it did interrupt genes potentially involved in lipid metabolic pathways of most derivative strains. Thus, it appears that strains retain the genetic integrity of the parental strains after the transformation process (FIG. 18A).

Figure 18B:
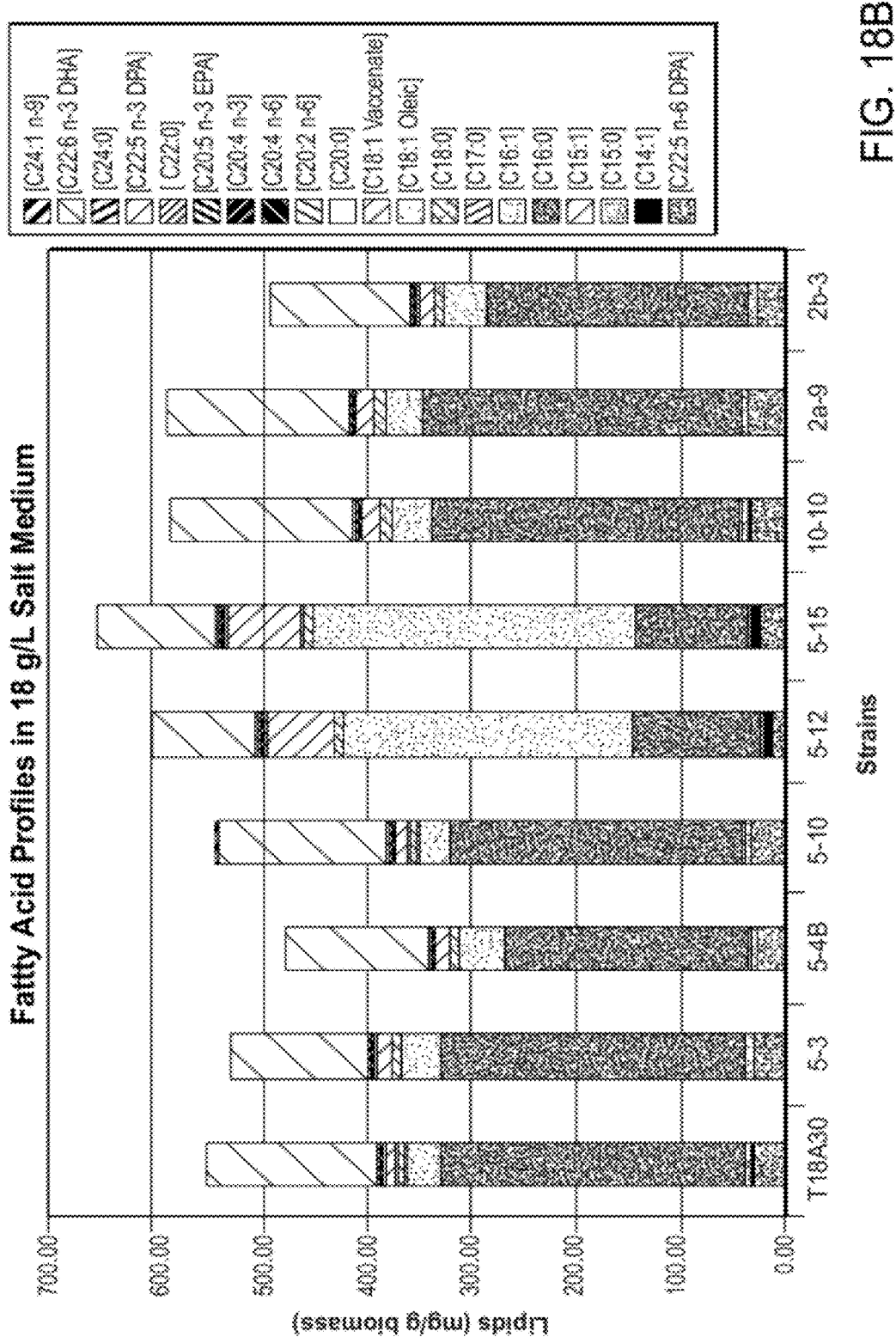
Figure 18C:
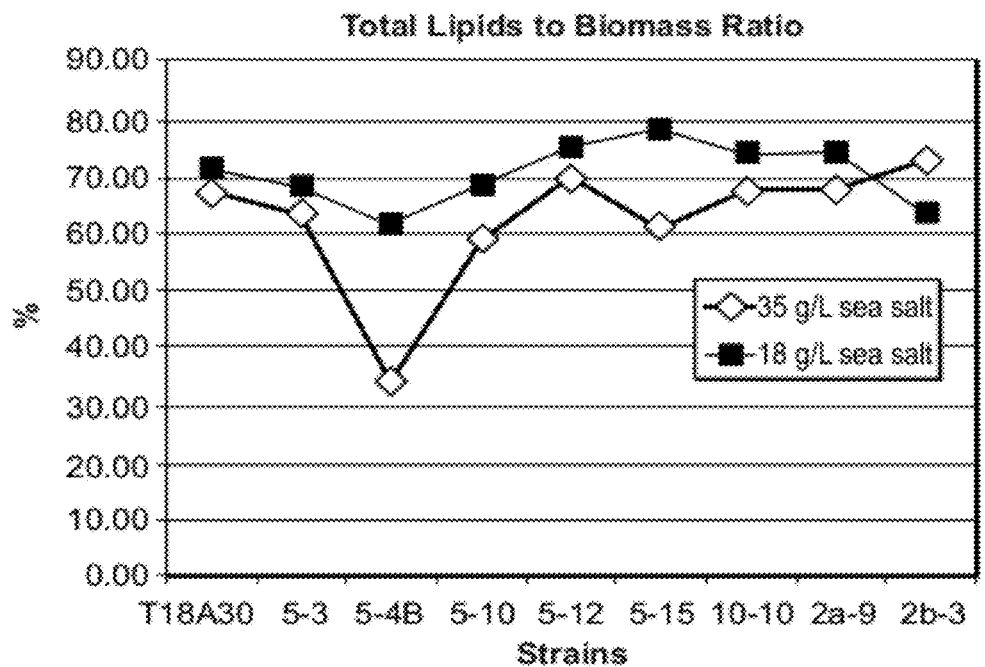

The ability to transform *Thraustochytrium* strains provides enormous opportunity to genetically modify these microbes and to channel metabolic pathways. Remarkably, when the transformed strains were grown in ONC-T18-GM0 containing 18 g/L sea salt, two strains showed significantly higher level of C16 fatty acid production than that of their parental strain. These results are useful in the development of this strain ONC-T18 into a platform for short chain fatty acid biofuel production. These results demonstrate that during the selection process of zeocin-resistant transformants, mutagenesis occurred in the cells with relatively high frequency. This high frequency of mutagenesis can be used in strain improvement programs (FIG. 18B).

Ratios of total lipid to biomass were higher in strains that produce high levels of short chain fatty acids than in low-level production strains (FIG. 18C); such higher rations may be beneficial to downstream oil extraction and the reduction of processing costs.

Figure 18D:
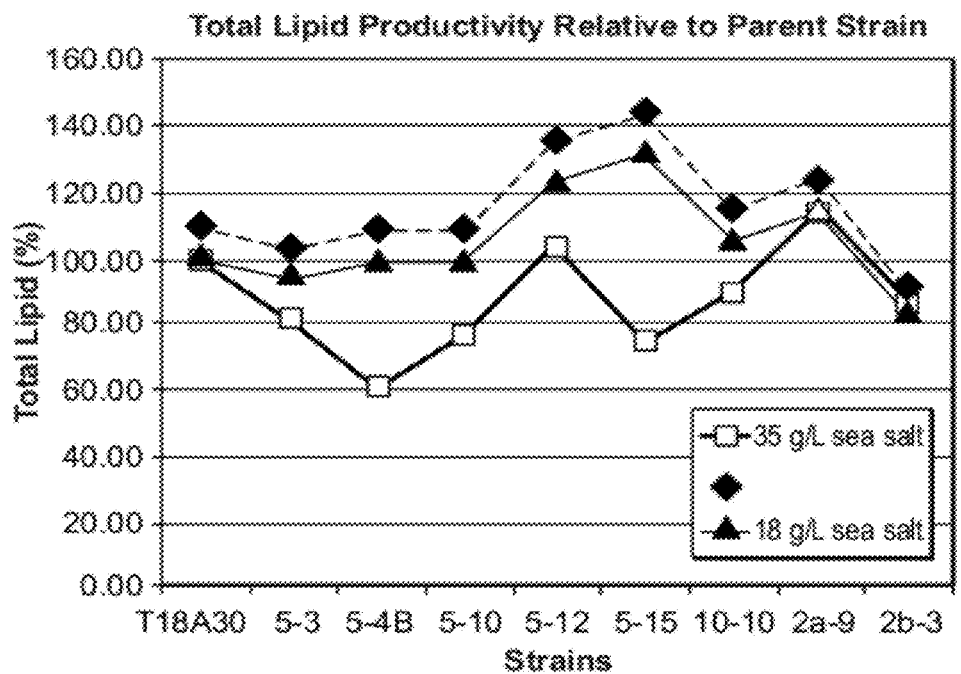

Growing in low sea salt ONC-T18-GM0 (18 g/L) enhanced overall total lipid productivity for most strains tested (FIG. 18D).

For example, it may be desirable to increase production of short chain fatty acids (i.e. fatty acids with less than 16 carbons) or of particular PUFA, as mentioned herein in the discussion of the PUFA biosynthetic pathway. It may, for example, be desirable to increase production of EPA (e.g., by mutating or knocking out the PKS genes and 45 elongase genes) or of ARA (e.g., by downregulating any of the PKS genes and/or upregulation of the 412 elongase gene).

Example 12

Stability of the ble Transgene in the Transformed Strains of *Thraustochytrium* sp. ONC-T18

The present Example confirms transgene stability in transformed *Thraustochytrium* sp. strains as described herein.

Transgene stability is important for certain applications of genetic engineering in industrial microbial strain improvement programs where microorganisms are used in pharmaceutical or industrial processes, and where product quantity and quality are paramount. We therefore carried out transgene stability estimate assays of transformed ONC-T18 strains. As for the growth rate assays described in Example 7, inocula of four strains of each transformation as well as their ancestor wild type strains were spotted on ONC-T18-GM0 agar plates in the absence of zeocin and incubated at 25° C. for seven days. (Each transformation had been performed using one of the five different plasmid constructs, each of which bears various zeocin-resistant gene expression cassettes driven by a combination of different promoters and terminators). Then, using the same method, strains were transferred on a new fresh ONC-T18-GM0 agar plate and incubated at 25° C. for 7 days; colony passages were carried out 6 times. Finally, strains were transferred back onto ONC-T18-GM0 agar plates either without or with zeocin at a concentration of 200 μg/mL media.

Results indicate that after six colony passages, all strains can grow well on ONC-T18-GM0 agar plates either with or without zeocin (FIG. 19A). However, on ONC-T18-GM0 agar plates having zeocin at a concentration at 200 μg/mL media, only the transformed strains grew well, whereas none of the wild type strains were able to grow (FIG. 19B).

These results demonstrate that there were no observed losses of the transgene in the strains examined. Furthermore, no resistance was observed in wild type strains, indicating that there was no spontaneous mutation for these traits and there was no detectable contamination. Presence of the ble transgene in the transformed strains after six time colony-passages was further confirmed using the PCR as described in Example 6. All transformed strains retained the ble transgene even after 6 colony passages. Thus, the ble transgene showed stability in transformed ONC-T18 strains.

Example 13

Mutagenic Agent

This Example describes, among other things, the discovery of an effective mutagenic agent. This agent is particularly useful for mutagenesis in Thraustochytrids.

Zeocin is an antibiotic that breaks chromosomal DNA in cells. It was hypothesized that antibiotic zeocin would be a useful mutagenic agent for thaustochytrid strains for strain improvement. At certain concentrations, zeocin can kill most treated cells, but some cells still survived. Treatment of cells at high concentration increases the mutation frequency, which can facilitate selection and isolation of mutated strains.

The marine protist wild type strain of ONC-T18 was chosen as a model system to test if zeocin would be effective to induce mutagenesis in this strain. One full loop of the inocula of ONC-T18, growing in the agar plates containing ONC-T18-GM0 medium [5 g/L yeast extract, 5 g/L peptone, 10 g/L D(+)-glucose, 35 g/L artificial sea salt, 1.25 mg/L trace elements (5 g/L $NaH_2PO_4.H_2O$, 3.15 g/L $FeCl_3.6H_2O$, 4.36 g/L $Na_2EDTA.2\ H_2O$, 0.6125 mg/L $CuSO_4.5H_2O$, 0.0597 g/L $Na_2MoO_4.2H_2O$, 0.022 g/L $ZnSO_4.7H_2O$, 0.01 g/L $CoCl_2.6H_2O$, 0.18 g/L $MnCl_2.4H_2O$, 13 μg/L $H_2SeO_3$, 2.7 mg/L $NiSO_4.6H_2O$, 1.84 mg/L $Na_3VO_4$ and 1.94 mg/L $K_2CrO_4$), 1.25 mg/L vitamins (1 mg/L vitamin B12, 1 mg/L biotin, 0.20 g/L thiamine HCl) and 20 g agar per liter], was inoculated into 50 mL liquid ONC-T18-GM0 medium, and incubated in a shaker incubator at 25° C. at 250 rpm for 36 hours. Half a milliliter of culture was transferred into a 1.5 mL tube and vortexed at full speed for 30 seconds, and then diluted in 50 mL sterilized water. One hundred microliters of the diluted inocula were respectively spread on the agar plates containing zeocin at various concentrations (0, 10, 30, 50, and 100 μg/mL). Plates were incubated at 25° C. incubator. The emergence and development of the colonies were observed daily. Six days post inoculation, the sizes of the colonies growing at 10 μg/mL zeocin were similar to that at 0 μg/mL zeocin, and gradually decreased at 30 to 50 μg/mL zeocin. The colony numbers per plate also were gradually reduced at 10, 30, and 50 μg/mL zeocin. Only a few of colonies were seen at 50 μg/mL zeocin. Remarkably, colony sectors with various visible colony-morphology changes were observed in some of the colonies growing at 50 μg/mL zeocin, but were not observed in the colonies growing at lower concentration or without zeocin, indicating that zeocin indeed is an effective mutagen agent for Thraustochytrid stains. Under these conditions, zeocin was effective within the range of at least 10-200 μg/mL; higher concentrations may well also be effective. For example, concentrations in the range of 200-500 μg/mL or higher could work. In some cases, higher concentrations of zeocin are used when salt concentrations are also increased to counteract possible degradation of zeocin from salt. Under the particular conditions utilized in the present Example, zeocin worked best at 50 μg/mL.

Example 14

A Novel Fermentation Procedure

This Example describes a two-stage fermentation method for obtaining high biomass, total lipids and PUFA production in Thraustochytrid strains.

The life cycle of the strain ONC-T18 was studied in detail through microscopic observations of the cells from cultures growing under various conditions such as ratios of C:N sources, dissolved oxygen level and temperatures. It was discovered that at low oxygen concentration with a high carbon to nitrogen ratio (C:N) (e.g., within the range of 40:1 to 1:~0, and specifically at 1:1 to 1:~0 and ambient temperature, the strain ONC-T18 grew vigorously and propagated mainly through production of zoospores, resulting in large numbers of small vegetative cells that contains relative small and less subcellular oil bodies. In contrast, at high C:N ratio, low oxygen level and relative low temperature (e.g., within the range of 10-30° C., and specifically at 20-25° C.), the strain ONC-T18 mainly propagated through directly vegetative cell dividing, resulting in a large population of giant cells that contain remarkably bulky subcellular oil bodies. Hence, a two-stage fermentation method was developed to maximize biomass, total lipid and PUFA productivity. This is one optimal method for growing and screening high lipid and PUFA thraustochytrid strains. The following three assays were conducted:

Assay I:

The wild type strain ONC-T18 was inoculated in 10 mL liquid ONC-T18-GM0 medium. Cultures were grown at 25° C. in a shaker incubator set at 250 rpm for 2 days. Then the inocula ($OD_{660}$=12) was inoculated in 100 mL ONC-T18-GM0 medium in 250 mL flasks. Three cultures were inoculated for each strain. Cultures were grown in a shaker incubator set at 250 rpm at 25° C. for 2 days, then switched to 150 rpm and 20° C., and grown for another 4 days. Biomasses of the cultures were harvested by transferring the cell cultures into a 50 mL falcon tube and centrifuging at 4000 rpm using a SORVALL LEGEND RT+ centrifuge (Thermo Fisher Scientific Inc., MA, USA). The biomass floated on the surface of the liquid medium as a compacted layer. The liquid medium was released by punching a very small hole at the bottom of the falcon tube using an 18G 1½ syringe needle. The pellet of the biomass in the tube was frozen in a −80° C. freezer overnight and then freeze dried using a freeze dryer for three days. The biomass of each sample was weighed.

Assay II:

The inocula was prepared as described in the Assay I. Next, the inocula ($OD_{660}=6$) was inoculated in 50 mL ONC-T18-GM0 medium in 250 mL flasks. Three cultures were inoculated for each strain. Cultures were grown in a shaker incubator set at 250 rpm at 25° C. for 2 days, then switched to 150 rpm and 20° C. At 2 days post inoculation, 5 mL of autoclaved 50% glucose was added into each culture flask, then at 4 days post inoculation, 6 mL of glucose were added. After 6 days post inoculation, biomasses of the cultures were harvested as described in Assay I.

Assay III:

The inocula were prepared as described in Assay I. Then the inocula ($OD_{660}=6$) was inoculated in 50 mL ONC-T18-GM0 medium in 250 mL baffled flasks. Cultures were grown in a shaker incubator set at 250 rpm at 25° C. At 2 and 4 days post inoculation, 5 and 6 mL of autoclaved 50% glucose were added into each culture flasks, respectively, as was done in Assay III. At day 6 post inoculation, biomasses of cultures were harvested as described in Assay II.

Total lipid and DHA contents of each sample were analyzed using direct transesterification method. Approximately 20 mg of freeze dried cell biomass and 3 mL of transesterification reaction buffer (methanol:hydrochloric acid:chloroform) were mixed by vortexing for 10 seconds and then incubated in a 90° C. water bath for two hours. After the completion of transesterification, the samples were removed and cooled down to ambient temperature. One mL of water was added and mixed via vortexing for 10 seconds. Fatty acid methyl esters (FAME) were then extracted by adding 3×2 mL of the solvent of hexane: chloroform (v/v, 4:1) and vortexing for 10 seconds, and allowed to sit until phase separations were completed.

Gas chromatographic (GC) analysis of the FAMEs was carried out using two internal standards (200 μL). One hexacosaenoic acid (C23:0) was added before transesterification and the other one, nonadecaenoic acid (C19:0) was added directly before analysis. Analyses were performed in an Agilent 6890 GC (Agilent Technologies, Palo Alto, Calif., USA) installed with a 30 m×0.32 mm internal diameter (0.25 μm film thickness) OMEGAWAX 320 fused-silica capillary column (Sigma-Aldrich, St. Louis, Mo., USA) and flame ionization detector set at 250° C., split ratio 50:1 to FID detector at 275° C. The injection volume was 1 μL. The carrier gas was $H_2$ with a constant flow of 5.0 mL per minute. Confirmation of the FAME identity was carried out using a Trace GC-DSQ mass spectrometer (Thermo Electron, Boston, USA) and comparison of the retention times for laboratory standards.

Results (Table 5) indicated that the fermentation conditions used in Assay II were the best for high lipid and DHA production in ONC-T18; levels within the range of about 50 to about 70% of dry biomass were observed; levels as high as about 70% to about 90% can be expected based on these findings. Observed DHA yields were within the range of about 5 to about 7.5 g/L culture. Based on these findings, DHA yields as high as about 45 to about 95 g/L can be expected.

Increasing dissolved oxygen for example by using baffled flask and high shaking speed in Assay III can significantly enhance the biomass productivity, but DHA productivity was considerable lower than that in Assay II. Therefore, optimization of fermentation parameters such as C:N ratio, glucose concentration, dissolved oxygen and temperature as well as the dynamics of these parameters during fermentation processes, impact cost effective production of lipids and PUFA in thraustochytrid strains. Without wishing to be bound by any particular theory, the inventors propose that the increased yields observed in Assay II as compared to Assay I may be attributed at least in part to the higher glucose concentration and/or lower levels of dissolved oxygen in Assay II.

TABLE 5

Biomass, total lipids and DHA productivities of *Thraustochytrium* sp. ONC-T18 under various fermentation conditions

| Assay | Biomass (g/L) | Total Lipid (mg/g) | DHA (g/L) |
| --- | --- | --- | --- |
| I | 7.10 | 211.20 | 0.45 |
| II | 41.32 | 671.09 | 5.94 |
| III | 46.50 | 661.07 | 3.06 |

Example 15

Application of a Mutagenic Agent

This Example describes the application of a mutagenic agent, zeocin, for strain improvement of Thraustochytrids.

Inocula from colony sectors were transferred into new fresh plates and developed into new strains. Four new strains, 1a, 1b, 3a and 3b were chosen for further study (results are shown in table 2). These four strains and their wild type parent strain ONC-T18 were inoculated in 10 mL liquid medium of ONC-T18-GM0. The cultures were grown at 25° C. in a shaker incubator set at 250 rpm for 3 days till the $OD_{660}$ was greater than 2. Then the inocula ($OD_{660}=6$) of each strain, including the wild type strain, were respectively inoculated in 50 mL ONC-T18-GM0 medium in 250 mL flasks. The following experimental conditions and procedures used were the same as in Example 14, assay II.

TABLE 6

Biomass, total lipids and DHA productivities of four selected strains and their wild type parent strain *Thraustochytrium* sp. ONC-T18

| Strains | Biomass (g/L) | Total Lipid (mg/g) | DHA (g/L) |
| --- | --- | --- | --- |
| ONC-T18 (parent strain) | 37.78 | 648.03 | 4.904 |
| 1a | 36.29 | 592.06 | 3.774 |
| 1b | 36.33 | 574.74 | 3.330 |
| 3a | 43.91 | 670.38 | 5.135 |
| 3b | 32.58 | 612.60 | 3.988 |

Experimental results indicated that three out of four selected strains produced significantly less biomass, total lipids and DHA compared to that of their wild type parent strain (Table 6). However, strain 3a produced more biomass, more lipids and DHA than that of its wild type strain. The high DHA productivity of strain 3a is due to not only its high biomass productivity, but high ratio of DHA to biomass. This result indicated that the mutagenic agent discovered can be used to improve a microbial strain's fitness (such as, e.g., capability of using cheaper carbon sources such as waste stream, glycerol, starch, cellulose, and hemicellulose), product quality and quantity such as ARA, DHA, and/or EPA productivity of PUFA, and fatty acid and/or lipid profiles favourable for biofuel applications.

Produced materials may be separated from production strains and/or media components by any of a variety of means. In some embodiments, extraction of produced materials is facilitated, for example, by taking one or more steps that alter fatty acid secretion and/or that weaken the cell wall.

Example 16

A Novel Strain of *Thraustochytrium* Sp

This Example describes the discovery of a novel strain of *Thraustochytrium* sp. with high productivity levels of lipids and DHA.

Single cells of ONC-T18 were spread on the agar plates containing ONC-T18-GM0 medium and 50 μg/mL zeocin. Ten to 15 days post inoculation, the colonies were screened visually. Large colonies without visible morphology changes were randomly isolated and developed into new strains. The biomass, total lipid and DHA productivity of new strains were compared. One strain ONC-T18/35/Z50 was initially found to be able to produce significantly more biomass, total lipids and DHA, which have been confirmed repeatedly with optimized fermentation conditions, methods and procedures described in Example 14, Assay II. In the two stage fermentation assays using ONC-T18-GM0 medium containing 35 g/L sea salt, the new strain ONC-T18/35/Z50 produced 5% more biomass, 7% more total lipids and 14% more DHA than that of its parent strain ONC-T18. Using the same medium, but containing 18 g/L sea salt, the new strain ONC-T18/35/Z50 produced about 10% more biomass, 20% more total lipids and 36% more DHA than that of its parent strain ONC-T18 (FIG. 19). Moreover, the ratios of DHA and total lipid to biomass, in high level DHA producing new strain ONC-T18/35/Z50, are higher than that of its parent strain, demonstrating that the new strain has a more robust capacity in converting carbon resources such as glucose to lipids and DHA. This novel strain is useful not only in improvement of yields, but also in reducing fermentation and downstream processing costs for biological lipid and PUFA production such as DHA from microalgae.

REFERENCES

Altschul, S. F., Gish, W., Miller, W., Myers, E. W., and Lipman, D. J. (1990). Basic local alignment search tool. *J Mol Biol* 215(3), 403-10.

Davis, S. J., and Vierstra, R. D. (1998). Soluble, highly fluorescent variants of green fluorescent protein (GFP) for use in higher plants. *Plant Mol Biol* 36(4), 521-8.

Dumas et al. (1994) The three-dimensional structure of a bleomycin resistance protein. *EMBO J.* 242(5), 595-601.

Gatignol et al. (1988) Bleomycin resistance conferred by a drug-binding protein. *FEBS Letters,* 230:171-175.

Higuchi, R., Krummel, B., and Saiki, R. K. (1988). A general method of in vitro preparation and specific mutagenesis of DNA fragments: study of protein and DNA interactions. *Nucleic Acids Res* 16(15), 7351-67.

Huang, J., Jiang, X., Zhang, X., Chen, W., Tian, B., Shu, Z., and Hu, S. (2008). Expressed sequence tag analysis of marine fungus *Schizochytrium* producing docosahexaenoic acid. *J Biotechnol* 138(1-2), 9-16.

Jain, R., Raghukumar, S., Sambaiah, K., Kumon, Y., and Nakahara, T. (2007). Docosahexaenoic acid accumulation in thraustochytrids: search for the rationale. *Mar Biol* 151, 1657-1664.

Jepson et al. (1998) *Pesticide Science,* 54(4), 360-367.

Leonard, A., Pereira, S., Sprecher, H., and Huang, Y.-S. (2004). Elongation of long-chain fatty acids. *Progress in Lipid Research* 43, 36-54.

Li et al. (2005) *Plant Sciences,* 169(3), 463-469.

Park and Morschhäuser (2005) *Eukaryotic cell* 4(8), 1328-1342.

Raghukumar S. (2008) Thraustochytrid Marine Protists: Production of PUFAs and Other Emerging Technologies. *Mar. Biotech.* 10:631-640.

Zhang, S. C., Wege, C., and Jeske, H. (2001). Movement proteins (BC1 and BV1) of Abutilon mosaic geminivirus are cotransported in and between cells of sink but not of source leaves as detected by green fluorescent protein tagging. *Virology* 290(2), 249-60.

EQUIVALENTS

Those skilled in the art will recognize, or be able to ascertain using no more than routine experimentation, many equivalents to the specific embodiments of the invention described herein. The scope of the present invention is not intended to be limited to the above Description. Alternative methods and materials and additional applications will be apparent to one of skill in the art, and are intended to be included within the following claims:

What is claimed is:

1. A method for transforming a *Thraustochytrium* cell comprising the steps of:
   (a) providing a competent *Thraustochytrium* cell;
   (b) delivering a recombinant nucleic acid into the competent *Thraustochytrium* cell, wherein the recombinant nucleic acid comprises a selectable marker and a tubulin promoter that is at least 80% identical to SEQ ID NO:10; and
   (c) culturing the competent *Thraustochytrium* cell in a culturing medium containing a selection agent that reduces growth of cells without the selectable marker.

2. The method of claim 1, wherein selectable marker is an antibiotic resistance gene.

3. The method of claim 2, wherein selection agent is an antibiotic.

4. The method of claim 3, wherein antibiotic is zeocin.

5. The method of claim 4, wherein the zeocin is present at a concentration greater than 50 µg/mL.

6. The method of claim 4, wherein the zeocin is present at a concentration of about 100 µg/mL.

7. The method of claim 2, wherein the antibiotic resistance gene is a zeocin resistance gene.

8. The method of claim 1, wherein the recombinant nucleic acid further comprises a gene expression cassette distinct from the selectable marker.

9. The method of claim 1, further comprising: (d) isolating a competent *Thraustochytrium* cell containing the selectable marker.

10. The method of claim 1, wherein the step of delivering comprises biolistic delivery of particles coated with the recombinant nucleic acid.

11. The method of claim 10, wherein the particles comprise gold particles.

12. The method of claim 1, wherein the culturing medium contains between about 10 g/L and about 40 g/L of salt.

13. The method of claim 1, wherein the recombinant nucleic acid comprises a tubulin terminator.

14. The method of claim 13, wherein the nucleotide sequence of the terminator is at least 80% identical to SEQ ID NO:14.

15. The method of claim 1, wherein the recombinant nucleic acid comprises a tubulin promoter operably linked to the selectable marker.

16. The method of claim 15, wherein the selectable marker is a zeocin resistance gene.

17. The method of claim 15, wherein the selectable marker comprises able gene.

18. The method of claim 17, wherein the ble gene is a Sh ble gene, a Tn5 ble gene or a Sa ble gene.

19. The method of claim 1, wherein the cell is ONC-T18.

20. The method of claim 1, wherein the culturing medium contains between about 15 g/L and about 35 g/L salt.

21. The method of claim 1, wherein the culturing medium contains between about 18 g/L and about 35 g/L salt.

22. A method for transforming a *Thraustochytrium* cell comprising the steps of:

(a) providing a competent *Thraustochytrium* cell;
(b) delivering a recombinant nucleic acid into the competent *Thraustochytrium* cell, wherein the recombinant nucleic acid comprises a selectable marker and a tubulin terminator that is at least 80% identical to SEQ ID NO:14; and
(c) culturing the competent *Thraustochytrium* cell in a culturing medium containing a selection agent that reduces growth of cells without the selectable marker.

23. The method of claim 22, wherein selectable marker is an antibiotic resistance gene.

24. The method of claim 23, wherein the selection agent is an antibiotic.

25. The method of claim 24, wherein the antibiotic is zeocin.

26. The method of claim 25, wherein the zeocin is contained in the culture medium at a concentration greater than 50 μg/mL.

27. The method of claim 25, wherein the zeocin is contained in the culture medium at a concentration of about 100 μg/mL.

28. The method of claim 22, wherein the recombinant nucleic acid further comprises a gene expression cassette distinct from the selectable marker.

29. The method of claim 22, further comprising: (d) isolating a competent *Thraustochytrium* cell containing the selectable marker.

30. The method of claim 22, wherein the step of delivering comprises biolistic delivery of particles coated with the recombinant nucleic acid.

31. The method of claim 30, wherein the particles comprise gold particles.

32. The method of claim 22, wherein the culturing medium contains between about 10 g/L and about 40 g/L of salt.

33. The method of claim 22, wherein the culturing medium contains between about 15 g/L and about 35 g/L salt.

34. The method of claim 22, wherein the culturing medium contains between about 18 g/L and about 35 g/L salt.

35. The method of claim 22, wherein the recombinant nucleic acid comprises a tubulin promoter.

36. The method of claim 35, wherein the nucleic acid sequence of the tubulin promoter is at least 80% identical to SEQ ID NO:10.

37. The method of claim 22, wherein the selectable marker is a zeocin resistance gene.

38. The method of claim 22, wherein the selectable marker comprises a ble gene.

39. The method of claim 38, wherein the ble gene is a Sh ble gene, a Tn5 ble gene or a Sa ble gene.

40. The method of claim 22, wherein the cell is ONC-T18.

* * * * *

UNITED STATES PATENT AND TRADEMARK OFFICE
CERTIFICATE OF CORRECTION

| | |
|---|---|
| PATENT NO. | : 9,133,463 B2 |
| APPLICATION NO. | : 13/414353 |
| DATED | : September 15, 2015 |
| INVENTOR(S) | : ShuoCheng Zhang et al. |

It is certified that error appears in the above-identified patent and that said Letters Patent is hereby corrected as shown below:

In The Specification

Column 10, line 58, "comprises able gene" should read:

-- comprises a *ble* gene --

Signed and Sealed this
Ninth Day of February, 2016

Michelle K. Lee
*Director of the United States Patent and Trademark Office*